US009441039B2

(12) United States Patent
Mytych et al.

(10) Patent No.: US 9,441,039 B2
(45) Date of Patent: Sep. 13, 2016

(54) ANTI-ERYTHROPOIETIN ANTIBODIES

(71) Applicant: AMGEN INC., Thousand Oaks, CA (US)

(72) Inventors: Daniel T. Mytych, Thousand Oaks, CA (US); Narendra Chirmule, Newbury Park, CA (US); Dohan K. Weeraratne, Ventura, CA (US)

(73) Assignee: Amgen Inc., Thousand Oaks, CA (US)

( * ) Notice: Subject to any disclaimer, the term of this patent is extended or adjusted under 35 U.S.C. 154(b) by 163 days.

(21) Appl. No.: 13/888,777

(22) Filed: May 7, 2013

(65) Prior Publication Data

US 2013/0295113 A1 Nov. 7, 2013

Related U.S. Application Data

(60) Provisional application No. 61/643,742, filed on May 7, 2012, provisional application No. 61/664,687, filed on Jun. 26, 2012.

(51) Int. Cl.
| | |
|---|---|
| *C07K 16/22* | (2006.01) |
| *C07K 16/26* | (2006.01) |
| *C07K 14/505* | (2006.01) |
| *G01N 33/68* | (2006.01) |

(52) U.S. Cl.
CPC .............. *C07K 16/26* (2013.01); *C07K 16/22* (2013.01); *G01N 33/6854* (2013.01); *C07K 2317/21* (2013.01); *C07K 2317/34* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 3,720,760 A | 3/1973 | Bennich et al. | |
| 4,179,337 A | 12/1979 | Davis et al. | |
| 4,301,144 A | 11/1981 | Iwashita et al. | |
| 4,331,647 A | 5/1982 | Goldenberg | |
| 4,464,456 A | 8/1984 | Fujikawa et al. | |
| 4,496,689 A | 1/1985 | Mitra | |
| 4,518,584 A | 5/1985 | Mark et al. | |
| 4,640,835 A | 2/1987 | Shimizu et al. | |
| 4,667,016 A | 5/1987 | Lai et al. | |
| 4,670,417 A | 6/1987 | Iwasaki et al. | |
| 4,703,008 A | 10/1987 | Lin | |
| 4,737,462 A | 4/1988 | Mark et al. | |
| 4,751,180 A | 6/1988 | Cousens et al. | |
| 4,791,192 A | 12/1988 | Nakagawa et al. | |
| 4,935,233 A | 6/1990 | Bell et al. | |
| 4,946,778 A | 8/1990 | Ladner et al. | |
| 5,011,912 A | 4/1991 | Hopp et al. | |
| 5,223,409 A | 6/1993 | Ladner et al. | |
| 5,225,539 A | 7/1993 | Winter | |
| 5,457,035 A | 10/1995 | Baum et al. | |
| 5,474,981 A | 12/1995 | Leder et al. | |
| 5,545,806 A | 8/1996 | Lonberg et al. | |
| 5,569,825 A | 10/1996 | Lonberg et al. | |
| 5,627,052 A | 5/1997 | Schrader | |
| 5,698,426 A | 12/1997 | Huse | |
| 5,814,318 A | 9/1998 | Lonberg et al. | |
| 5,821,337 A | 10/1998 | Carter et al. | |
| 5,859,205 A | 1/1999 | Adair et al. | |
| 5,869,619 A | 2/1999 | Studnicka | |
| 5,877,293 A | 3/1999 | Adair et al. | |
| 5,877,397 A | 3/1999 | Lonberg et al. | |
| 5,886,152 A | 3/1999 | Nakatani et al. | |
| 6,054,297 A | 4/2000 | Carter et al. | |
| 6,133,426 A | 10/2000 | Gonzalez et al. | |
| 6,210,924 B1 | 4/2001 | Hu et al. | |
| 6,696,245 B2 | 2/2004 | Winter et al. | |
| 6,703,199 B1 | 3/2004 | Koide | |
| 6,846,634 B1 | 1/2005 | Tomlinson et al. | |
| 6,881,557 B2 | 4/2005 | Foote | |
| 7,064,244 B2 | 6/2006 | Jakobovits et al. | |
| 7,754,433 B2 | 7/2010 | Babcook | |
| 2003/0039958 A1 | 2/2003 | Holt | |
| 2004/0009507 A1 | 1/2004 | Winter | |
| 2004/0038291 A2 | 2/2004 | Tomlinson | |
| 2004/0096447 A1 | 5/2004 | Yasuda et al. | |
| 2004/0202995 A1 | 10/2004 | de Wildt | |
| 2005/0118643 A1 | 6/2005 | Burgess et al. | |
| 2005/0202512 A1 | 9/2005 | Tomlinson | |
| 2005/0238646 A1 | 10/2005 | Ledbetter | |

FOREIGN PATENT DOCUMENTS

| | | |
|---|---|---|
| EP | 439095 B2 | 12/2004 |
| WO | 8705330 A1 | 9/1987 |
| WO | 9008822 A1 | 8/1990 |
| WO | 9202551 A1 | 2/1992 |
| WO | 9310151 A1 | 5/1993 |
| WO | 9321232 A1 | 10/1993 |

(Continued)

OTHER PUBLICATIONS

Paul, W.E. Fundamental Immunology, Third Edition (textbook), "Fv Structure and Diversity in Three Dimensions" pp. 292-295; Raven Press, New York (1993).*
Casset et al. A peptide mimetic of an anti-CD4 monoclonal antibody by rational design. Biochem Biophys Res Comm. vol. 307:198-205 (2003).*
MacCallum et al. Antibody-antigen interactions: Contact analysis and binding site topography. J Mol Biol. vol. 262:732-745 (1996).*
Rudikoff et al. Single amino acid substitution altering antigen-binding specificity. Proc. Natl. Acad. Sci. USA, 79(6):1979-1983 (Mar. 1982).*

(Continued)

*Primary Examiner* — Elizabeth C Kemmerer
*Assistant Examiner* — Regina M Deberry
(74) *Attorney, Agent, or Firm* — Lisa E. Alexander

(57) ABSTRACT

The present disclosure provides compositions and methods relating to antibodies that specifically bind to human erythropoietin. The disclosure provides nucleic acids encoding such antibodies and methods of making and using such antibodies.

6 Claims, 8 Drawing Sheets

(56) References Cited

FOREIGN PATENT DOCUMENTS

| WO | 9410308 A1 | 5/1994 |
|---|---|---|
| WO | 9824838 A1 | 6/1998 |
| WO | 0076310 A9 | 12/2000 |
| WO | 2005094879 A2 | 10/2005 |

OTHER PUBLICATIONS

Aalberse RC, van der Gaag R, van Leeuwen J. Serologic aspects of IgG4 antibodies. I. Prolonged immunization results in an IgG4-restricted response. J Immunol 1983;130(2):722-726.

Aplin and Wriston, "Preparation, Properties, and Applications of Carboydrate Conugates of Proteins and Lipids," CRC Crit. Rev. Biochem., pp. 259-306 (1981).

Arbones et al., 1994, "Lymphocyte homing and leukocyte rolling and migration are impaired in L-selectin-deficient mice," Immunity. 1:247-60.

Ashkenazi et al., "Protection against endotoxic shock by a tumor necrosis factor receptor immunoadhesin," 1991, PNAS USA 88:10535.

Babcook et al., "A novel strategy for generating monoclonal antibodies from single, isolated lymphocytes producing antibodies of defined specificities," Proc. Natl. Acad. Sci. USA 93:7843 48 (1996).

Barger TE, Kuck AJ, Chirmule N, et al. Detection of anti-ESA antibodies in human samples from PRCA and non-PRCA patients: an immunoassay platform comparison. Nephrology Dialysis Transplant 27(2):688-693 (2011).

Barger, T et al., "A detailed examination of the antibody prevalence and characteristics of anti-ESA antibodies," Nephrol, Dialysis, Transplant 27(10):3892-3899 (2012).

Baron et al., 1995, "Co-regulation of two gene activities by tetracycline via a bidirectional promoter." Nucleic Acids Res. 23:3605-06.

Bauer et al. 1985, "A genetic enrichment for mutations constructed by oligodeoxynucleotide-directed mutage," Gene 37:73.

Baum et al., 1994, "Molecular characterization of murine and human OX40/OX40 ligand systems: identification of a human OX40 ligand as the HTLV-1-regulated protein gp34," EMBO J. 13:3992-4001.

Bird et al., "Single-Chain Antigen-Binding Proteins," Science 242:423 426, 1988.

Bloom et al., 1997, "Intrachain disulfide bond in the core hinge region of human IgG4," Protein Science 6:407.

Boerner et al., 1991 "Production of antigen-specific human monoclonal antibodies from in vitro-primed human splenocytes," J. Immunol. 147:86 95.

Bowie et al., "A method to identify protein sequences that fold into a known three-dimensional structure," Science, 253:164-170 (1991).

Brenner et al., "Population statistics of protein structures: lessons from structural classifications," Curr. Op. Struct. Biol., 7(3):369-376 (1997).

Bruggemann et al., "Production of human antibody repertoires in transgenic mice" Curr. Opin. Biotechnol. 8:455 58 (1997).

Burton et al., "Human antibodies from Combinatorial libraries," 1994 Adv. Immunol. 57:191 280.

Byrn et al., 1990, "Biological properties of a CD4 immunoadhesin," Nature 344:677.

Casadevall N, Nataf J, Viron B, et al. Pure Red-Cell Aplasia and Antierythropoietin Antibodies in Patients Treated with Recombinant Erythropoietin. New England Journal of Medicine 2002;346(7):469-475.

Chen, J., M. Trounstine, F. W. Alt, F. Young, C. Kurahara, J. Loring, D. Huszar "Immunoglobulin gene rearrangement in B-cell deficient mice generated by targeted deletion of the JH locus." International Immunology 5 (1993): 647-656.

Cheung, et al. (1990) "Epitope-specific antibody response to the surface antigen of duck hepatitis B virus in infected ducks," Virology 176:546-552.

Choi et al., 1993, "Transgenic Mice containing a human heavy chain immunoglobulin gene fragment cloned in a yeast artificial chromosome," Nature Genetics 4: 117-23.

Chou et al., "Prediction of protein conformation," Biochemistry, 13(2):222-245 (1974).

Chou et al., "Conformation parameters for amino acids in Helical Beta-sheet and random coil regions calculated from proteins," Biochemistry, 13(2):211-222 (1974).

Chou et al., "Prediction of the secondary structure of proteins from their amino acid sequence," Adv. Enzymol. Relat. Areas Mol. Biol., 47:45-148 (1978).

Chou et al., "Prediction of Beta-turns," Biophys. J., 26:367-384 (1979).

Chou et al., "Empirical predictions of protein conformation," Ann. Rev. Biochem., 47:251-276.

Clark, M., "Antibody humanization: a case of 'Emperor's new clothes'?" Immunology Today. 21(8):397-402, 2000.

Cockett et al., "High level expression of tissue inhibitor of metalloproteinases in Chinese hamster ovary cells using glutamine synthetase gene amplification," Bio/Technology 8:2 (1990).

Colberre-Garapin et al., "A new dominant hybrid selective marker for higher eukaryotic cells," J. Mol. Biol. 150:1 (1981).

Craik, "Use of oligonucleotides fro site-specific mutagenesis," BioTechniques, Jan. 1985, 12-19.

Crameri, et al., "DNA shuffling of a family of genes from diverse species accelerates directed evolution," Nature, 391, 288 291, 1998.

Crouse et al., "Expression and amplification of engineered mouse dihydrofolate reductase minigenes," Mol. Cell. Biol. 3:257 (1983).

Dall'Acqua WF, et al., "Antibody humanization by framework shuffling," Methods 36(1):43-60, 2005.

Davis et al., 1999, "Transgenic mice as a source of fully human antibodies for the treatment of cancer," Cancer Metastasis Rev. 18:421-25.

Davis et al., Production of human antibodies from transgenic mice in Lo, ed. Antibody Engineering: Methods and Protocols, Humana Press, NJ:191-200 (2003).

de Graaf et al., 2002, "Expression of scFvs and scFv fusion proteins in eukaryotic cells," Methods Mol Biol. 178:379-87.

Elliott et al. "Isolation and characterization of conformation sensitive antierythropoietin monoclonal antibodies: effect of disulfide bonds and carbohydrate on recombinant human erythropoietin structure," Blood 87(7):2714-22 Apr. 1996.

Elliott et al. "Fine-structure epitope mapping of antierythropoietin monoclonal antibodies reveals a model of recombinant human erythropoietin structure," Blood 87(7):2702-13, Apr. 1996.

Evens AM, Bennett CL, Luminari S. Epoetin-induced pure red-cell aplasia (PRCA): preliminary results from the research on adverse drug events and reports (RADAR) group. Best Pract Res Clin Haematol 2005;18(3):481-489.

Fanslow et al., 1994, "Structural characteristics of CD40 ligand that determine biological function," Semin. Immunol. 6:267-78.

Fell et al., "Genetic construction and characterization of a fusion protein consisting of a chimeric F(ab') with specificity for carcinomas and human IL-2," J. Immunol. 146:2446-2452 (1991).

Fishwild et al., 1996, "High-avidity human IgGk monoclonal antibodies from a novel strain of minilocus transgenic mice," Nature Biotechnology 14: 845-51.

Foecking et al., "Powerful and versatile enhancer-promoter unit for mammalian expression vectors," Gene 45:101 (1986).

French MM., "Serum IgG subclasses in normal adults," Monogr Allergy 1986;19:100-107.

Gallo et al., 2000, "The human immunoglobulin loci introduced into mice: V (D) and J gene segment usage similar to that of adult humans," Eur J Immun 30:534-40.

Gentz et al., "Bioassay for trans-activation using purified human immunodeficiency virus tat-encoded protein: trans-activation requires mRNA synthesis," Proc. Natl. Acad. Sci. USA 86:821-824 (1989).

Gillies et al., "Antibody-targeted interleukin 2 stimulates T-cell killing of autologous tumor cells," Proc. Natl. Acad. Sci. 89:1428-1432 (1992).

(56) References Cited

OTHER PUBLICATIONS

Glasky et al., "Stability of specific immunoglobulin secretion by EBV-transformed lymphoblastoid cells and human-murine heterohybridomas," Hybridoma 8:377 89 (1989).
Gluzman et al., 1981, "SV40-transformed simian cells support the replication of early SV40 mutant," Cell 23:175.
Goeddel, 1990, "Gene Expression Technology: Methods in Enzymology 185," Academic Press, San Diego, CA.
Green et al., 1994, "Antigen-specific human monoclonal antibodies from mice engineered with human Ig heavy and light chain YACs," Nature Genet. 7:13-21.
Green et al., 1998, "Regulation of B cell development by variable gene complexity in mice reconstituted with human immunoglobulin yeast artificial chromosomes," J Exp Med. 188:483-95.
Green, 1999, "Antibody engineering via genetic engineering of the mouse: XenoMouse strains are a vehicle for the facile generation of therapeutic human monoclonal antibodies," J Immunol Methods. 231:11-23.
Gribskov et al., "Profile analysis: Detection of distantly related proteins," Proc. Nat. Acad. Sci., 84(13):4355-4358 (1987).
Gribskov et al., "Profile analysis," Meth. Enzym., 183:146-159 (1990).
Harding et al., 1995, "Class switching in human immunoglobulin transgenic mice," Annals of the New York Academy of Sciences pp. 536-546.
Harris, R.J. "Processing of C-terminal lysine and arginine residues of proteins isolated from mammalian cell culture," Journal of Chromatography 705:129-134, 1995.
Holliger et al., 1993, "Diabodies: Small bivalent and bispecific antibody fragments," Proc. Natl. Acad. Sci. USA 90:6444-48 (1993).
Holliger and Hudson, 2005, "Engineered antibody fragments and the rise of single domains," Nature Biotechnology, 23, 9, 1126-1136.
Holm et al., "Protein folds and families: sequence and structure alignments," Nucl. Acid. Res., 27(1):244-247 (1999).
Hoogenboom et al., 1992 "By-passing immunization: Human antibodies from synthetic repertoires of germline $V_H$ gene segments rearranged in vitro," J. Molec. Biol. 227:381 388.
Hopp et al., "A short polypeptide marker sequence useful for recombinant protein identification and purification," Bio/Technology 6:1204, 1988.
Hoppe et al., 1994, "A parallel three stranded alpha-helical bundle at the nucleation site of collagen triple-helix formation," FEBS Letters 344:191.
Huse et al., "Generation of a large combinatorial library of the immunoglobulin repertoire in phage lambda," 1989 Science 246:1275 81.
Huston et al., 1988, "Protein engineering of antibody binding sites: Recovery of specific activity in an anti-digoxin single-chain Fv analogue produced in *Escherichia coli*," Proc. Natl. Acad. Sci. USA 85:5879.
Hwang W. et al., "Use of human germline genes in a CDR homology-based approach to antibody humanization," Methods. 36(1):35-42, 2005.
Ito K, Futamura M, Moverare R, et al. The usefulness of casein-specific IgE and IgG4 antibodies in cow's milk allergic children. Clin Mol Allergy 2012;10(1):1-1.
Jakobovits et al., 1993, "Germ-line transmission and expression of a human-derived yeast artificial chromosome," Nature. 362:255-58.
Jakobovits et al., 1993, "Analysis of homozygous mutant chimeric mice: Deletion of the immunoglobulin heavy-chain joining region blocks B-cell development and antibody production," Proc Natl Acad Sci U S A. 90:2551-55.
Jakobovits, 1994, "YAC vectors. Humanizing the mouse genome," Curr Biol. 4:761-63.
Jakobovits et al., 1995 "Production of antigen-specific human antibodies from mice engineered with human heavy and light chain YACsa," Ann. N. Y. Acad. Sci. 764:525 35.
Jakobovits A, 1998, "The long-awaited magic bullets: therapeutic human monoclonal antibodies from transgenic mice," Exp. Opin. Invest. Drugs. 7:607-14.
Jakobovits, 1998, "Production and selection of antigen-specific fully human monoclonal antibodies from mice engineered with human Ig loci," Advanced Drug Delivery Reviews 31:33-42.
Jalkanen et al., 1985, "Heparan sulfate proteoglycans from mouse mammary epithelial cells: localization on the cell surface with a monoclonal antibody," J. Cell. Biol. 101:976-985.
Jalkanen et al., 1987, "Cell surface proteoglycan of mouse mammary epithelial cells is shed by cleavage of its matrix-binding ectodomain from its membrane-associated domain," J. Cell. Biol. 105:3087-3096.
Jones, D., "Progress in protein structure prediction," Curr. Opin. Struct. Biol., 7(3):377-87 (1997).
Kang et al., 1991 "Linkage of recognition and replication functions by assembling combinatorial antibody Fab libraries along phage surfaces," Proc. Natl. Acad. Sci. USA 88:4363 66.
Kellermann et al., 2002, "Antibody discovery: the use of transgenic mice to generate human monoclonal antibodies for therapeutics," Curr. Opin .Biotechnol. 13:593-97.
Kirkland et al., (1986) "Analysis of the fine specificity and cross-reactivity of monoclonal anti-lipid A antibodies," J. Immunol. 137:3614-3619.
Kohler, "Immunoglobulin chain loss in hybridoma lines," Proc. Natl. Acad. Sci. USA 77:2197 (1980).
Koren E, Zuckerman LA, Mire-Sluis AR. Immune responses to therapeutic proteins in humans—clinical significance, assessment and prediction. Curr Pharm Biotechnol 2002;3(4):349-360.
Kortt et al., 1997, "Single-chain Fv fragments of anti-neuraminidase antibody NC10 containing five-and ten-residue linkers form dimers and with zero-residue linker a trimer," Prot. Eng. 10:423.
Kortt et al., 2001, "Dimeric and trimeric antibodies: high avidity scFvs for cancer targeting," Biomol. Eng. 18:95-108.
Kriangkum et al., "Bispecific and bifunctional signle chain recombinant antibodies," 2001, Biomol. Eng. 18:31-40.
Landschulz et al., 1988, "The leucine zipper: a hypothetical structure common to a new class of DNA binding proteins," Science 240:1759.
Lantto et al., "Chain shuffling to modify properties of recombinant immunoglobulins," Methods Mol. Biol. 178:303-16 (2002).
Larrick et al., 1989, "Polymemse Chain Reaction Using Mixed Primers: Cloning of Human Monoclonal Antibody Variable Region Genes from Single Hybridoma Cells," Bio/Technology 7:934.
Larrick et al., "PCR amplification of antibody genes," Methods: A Companion to Methods in Enzymology 2:106, 1991.
Liu et al., 1987, "Chimeric mouse-human IgG1 antibody that can mediate lysis of cancer cells," Proc. Nat. Acad. Sci. USA 84:3439.
Lonberg et al., 1994, "Antigen-specific human antibodies from mice comprising four distinct genetic modifications," Nature 368: 856-59.
Lonberg, 1994, Transgenic Approaches to Human Monoclonal Antibodies in Handbook of Experimental Pharmacology 113: 49-101.
Lonberg et al., 1995, "Human antibodies from transgenic mice," Internal Review of Immunology 13: 65-93.
Lowy et al., "Isolation of transforming DNA: cloning the hamster aprt gene," Cell 22:817 (1980).
Lunde et al., "Troybodies and pepbodies," 2002, Biochem. Soc. Trans. 30:500-06.
Maloney JM, Rudengren M, Ahlstedt S, et al. "The use of serum-specific IgE measurements for the diagnosis of peanut, tree nut, and seed allergy," J Allergy Clin Immunol 2008;122(1):145-151.
Maniatis et al., 1987, "Regulation of inducible and tissue-specific gene expression," Science 236:1237.
Marks et al., "By-passing immunization: building high affinity human antibodies by chain shuffling," Bio/Technology, 10, 779 783, 1992.
McMahan et al., 1991, "A novel IL-1 receptor, cloned from B cells by mammalian expression, is expressed in many cell types," EMBO J. 10:2821.

(56) References Cited

OTHER PUBLICATIONS

Mendez et al., 1997, "Functional transplant of megabase human immunoglobulin loci recapitulates human antibody response in mice," Nat Genet. 15:146-56.
Mire-Sluis AR, Barrett YC, Devanarayan V, et al. "Recommendations for the design and optimization of immunoassays used in the detection of host antibodies against biotechnology products," J Immunol Methods 2004;289(1-2):1-16.
Miura Y, Kami M, Yotsuya R, et al. Pure red-cell aplasia associated with pegylated interferon-alpha-2b plus ribavirin. Am J Hematology 2008; 83(9):758-759.
Miyake, T. et al. "Purification of human erythropoietin," J. Biol. Chem. 252, 5558 (1977).
Moldenhauer et al. (1990) "Identity of HML-1 antigen on intestinal intraepithelial T cells and of B-ly7 antigen on hairy cell leukaemiam" Scand. J. Immunol. 32:77-82.
Morel et al. (1988) "Monoclonal antibodies to bovine serum albumin: affinity and specificity determinations," Molec. Immunol 25:7-15.
Moult J., "The current state of the art in protein structure prediction," Curr. Op. In Biotech., 7(4):422-427 (1996).
Mulligan & Berg, "Selection for animal cells that express the *Escherichia coli* gene coding for xanthine-guanine phosphoribosyltransferase," Proc. Natl. Acad. Sci. USA 78:2072 (1981).
Mytych DT, La S, Barger T, et al. "The development and validation of a sensitive, dual-flow cell, SPR-based biosensor immunoassay for the detection, semi-quantitation, and characterization of antibodies to darbepoetin alfa and epoetin alfa in human serum." J Pharm Biomed Anal 2009;49(2):415-426.
Mytych DT, Barger TE, King C, et al. "Development and characterization of a human antibody reference panel against erythropoietin suitable for the standardization of ESA immunogenicity testing," J ImmunoMeth 382(1):129-141 (2012).
Naramura et al., "Mechanisms of cellular cytotoxicity mediated by a recombinant antibody-IL2 fusion protein against human melanoma cells," Immunol. Lett. 39:91-99 (1994).
Neuberger, 1996, "Generating high-avidity human Mabs in mice," Nature Biotechnology 14: 826.
Nisonoff et al., "Separation of univalent fragments from the bivalent rabbit antibody molecule by reduction of disulfide bonds," Arch. Biochem. Biophys. 89:230, 1960.
Nygren and Uhlen, 1997, "Scaffolds for engineering novel binding sites in proteins," Current Opinion in Structural Biology, 7, 463-469.
O'Hare et al., "Transformation of mouse fibroblasts to methotrexate resistance by a recombinant plasmid expressing a prokaryotic dihydrofolate reductase," Proc. Natl. Acad. Sci. USA 78:1527 (1981).
Padlan et al., 1995, "Identification of specificity-determining residues in antibodies," FASEB J. 9:133-39.
Patten et al., "Applications of DNA shuffling to pharmaceuticals and vaccines," Curr. Opin. Biotechnol., 8, 724 733, 1997.
Poljak et al., "Production and structure of diabodies," Structure 2:1121-23 (1994).
Pollock C, Johnson DW, Hörl WH, et al. Pure red cell aplasia induced by erythropoiesis-stimulating agents. Clin J Am Soc Nephrol 2008;3(1):193-199.
Porter, R.R., "The hydrolysis of rabbit y-globulin and antibodies with crystalline papain," Biochem. J. 73:119, 1959.
Rasmussen et al., 1998, "Isolation, characterization and recombinant protein expression in Veggie-CHO: A serum-free CHO host cell line," Cytotechnology 28:31.
Riechmann et al., 1988, "Reshaping human antibodies for therapy," Nature 332:323.
Russel et al., 2000, "Production of protective human antipneumococcal antibodies by transgenic mice with human immunoglobulin loci," Infect Immun 68:1820-26.

Santerre et al., "of prokaryotic genes for hygromycin B and G418 resistance as dominant-selection markers in mouse L cells," Gene 30:147 (1984).
Sastry et al., "Cloning of the immunological repertoire in *Escherichia coli* for generation of monoclonal catalytic antibodies: construction of a heavy chain variable region-specific cDNA library," Proc. Natl. Acad. Sci. USA 86:5728 32 (1989).
Schellekens H, Jiskoot W. Eprex-associated pure red cell aplasia and leachates. Nat Biotechnol 2006;24(6):613-614.
Schier et al., 1996, "Isolation of picomolar affinity anti-c-erbB-2 single-chain Fv by molecular evolution of the complementarity determining regions in the center of the antibody binding site." J. Mol. Biol. 263:551.
Schlebusch et al., 1997 "Production of a single-chain fragment of the murine anti-idiotypic antibody ACA125 as phage-displayed and soluble antibody by recombinant phage antibody technique," Hybridoma 16:47 52.
Shakib FF. "The IgG4 subclass," Monogr Allergy 1986;19:223-226.
Sippl et al., "Threading thrills and threats," Structure, 4(1):15-19 (1996).
Stahli et al. (1983) "Distinction of epitopes by monoclonal antibodies," Methods in Enzymology 9:242-253.
Stavnezer JJ. Molecular processes that regulate class switching. Curr Top Microbiol Immunol 2000;245(2):127-168.
Swanson SJ, Ferbas J, Mayeux P, et al. Evaluation of methods to detect and characterize antibodies against recombinant human erythropoietin. Nephron Clin Pract 2004;96(3):c88-c95.
Syed et al., "Efficiency of signaling through cytokine receptors depends critically on receptor orientation," Nature, 395(6701):511-6 (1998).
Szybalska & Szybalski, "Genetics of human cell lines, IV. DNA-mediated heritable transformation of a biochemical trait," Proc. Natl. Acad. Sci. USA 48:2026 (1962).
Tamura et al., 2000, "Structural correlates of an anticarcinoma antibody: identification of specificity-determining residues (SDRs) and development of a minimally immunogenic antibody variant by retention of DSRs only," J. Immunol. 164:1432-41.
Taylor et al., 1992, "A transgenic mouse that expresses a diversity of human sequence heavy and light chain immunoglobulins," Nucleic Acids Research 20: 6287-95.
Taylor et al., 1994, "Human immunoglobulin transgenes undergo rearrangement, somatic mutation and class switching in mice that lack endogenous IgM," International Immunology 6: 579-91.
Thompson et al., "Affinity Maturation of a High-affinity Human Monoclonal Antibody Against the Third Hypervariable Loop of Human Immunodeficiency Virus: Use of Phage Display to Improve Affinity and Broaden Strain Reactivity," J. Mol. Biol., 256, 7 88, 1996.
Thornton et al. "Prediction of progress at last," Nature 354:105 (1991).
Thorpe R, Swanson SJ. Current methods for detecting antibodies against erythropoietin and other recombinant proteins. Clin Diagn Lab Immunol 2005;12(1):28-39.
Tomizuka et al., 1997, "Functional expression and germline atransmission of a human chromosome fragment in chimaeric mice," Nature Genetics 16: 133-43.
Tomizuka et al., 2000, "Double trans-chromosomic mice: maintenance of two individual human chromosome fragments containing Ig heavy and kappa loci and expression of fully human antibodies," Proceedings of the National Academy of Sciences USA 97: 722-27.
Tsuda et al., 1997, Inactivation of the MouseHPRTLocus by a 203-bp retroposon insertion and a 55-kb gene-targeted deletion: establishment of new HPRT-deficient mouse embryonic stem cell lines, Genomics. 42:413-21.
Tuaillon et al., 1993, "Human immunoglobulin heavy-chain minilocus recombination in transgenic mice: gene-segment use in mu and gamma transcripts," Proceedings of the National Academy of Sciences USA 90: 3720-24.
Tuaillon et al., 1994, "Biased utilization of $D_{HQ52}$ and $J_H4$ gene segments in a human Ig transgenic minilocus Is independent of antigenic selection," Journal of Immunology 152: 2912-20.

(56) References Cited

OTHER PUBLICATIONS

Urlaub et al., 1980, "Isolation of Chinese hamster cell mutants deficient in dihydrofolate reductase activity," Proc. Natl. Acad. Sci. USA 77:4216-20.

van Helden PM, van den Berg HM, Gouw SC, et al. "IgG subclasses of anti-FVIII antibodies during immune tolerance induction in patients with hemophilia A," British J Haematology 2008;142(4):644-652.

van Schouwenburg PA, Krieckaert CL, Nurmohamed M, et al. IgG4 Production Against Adalimumab During Long Term Treatment of RA Patients. J Clin Immunol 2012], IFN-β 1b in multiple sclerosis patients [Deisenhammer F, Reindl M, Berger T. Immunoglobulin subclasses in patients with neutralizing and nonneutralizing antibodies against IFN-beta1b. J Interferon Cytokine Res 2001;21(3):167-171.

Vaughan et al. "Human antibodies by design," Nature Biotechnology, 16, 535 539, 1998.

Voss et al., 1986, "The role of enhancers in the regulation of cell-type-specific transcriptional control," Trends Biochem. Sci. 11:287.

Walder et al., 1986, "Oligodeoxynucleotide-directed mutagenesis using the yeast transformation system," Gene 42:133.

Ward et al., 1989, "Binding activities of a repertoire of single immunoglobulin variable domains secreted from *Escherichia coli*," Nature 334:544.

Ward et al., "Genetic Manipulation and Expression of Antibodies," in Monoclonal Antibodies: Principles and Applications, Birch et al., (eds.), p. 137 (Wiley Liss, Inc. 1995).

Weeraratne et al., "Measurement of anti-erythropoietin-stimulating agent IgG4 antibody as an indicator of antibody-mediated pure cell aplasia," Clinical Vaccine Immunol. 20(1): 46-51 (2013).

Wigler et al., "Transfer of purified herpes virus thymidine kinase gene to cultured mouse cells," Cell 11:223 (1977).

Wilson et al., "The structure of an antigenic determinant in a protein," Cell 37:767 (1984).

Winter et al., 1993, "Humanized Antibodies," TIPS 14:139.

Winter et al., 1994, "Making antibodies by phage display technology," Annu. Rev. Immunol. 12:433 55.

Wu and Wu, "Delivery systems for gene therapy," Biotherapy 3:87-95 (1991).

Yang et al., "CDR Walking Mutagenesis for the Affinity Maturation of a Potent Human Anti-HIV-1 Antibody into the Picomolar Range," J. Mol. Biol., 254, 392 403, 1995.

Zhang, W., et al., "Humanization of an anti-human TNF-alphaA antibody by variable region resurfacing with the aid of molecular modeling," Molecular Immunology. 42(12):1445-1451, 2005.

* cited by examiner

Dose Response Curves of Anti-EPO Antibodies

Neutralizing Activity of five anti-EPO Antibodies in a Cell-based Assay

Fig. 4

Topographical map illustrating human anti-EPO neutralizing antibody 8C10 and 3F5 binding to site 1 and 3A4 binding to site 2 on EPO; Non-neutralizing 9F7

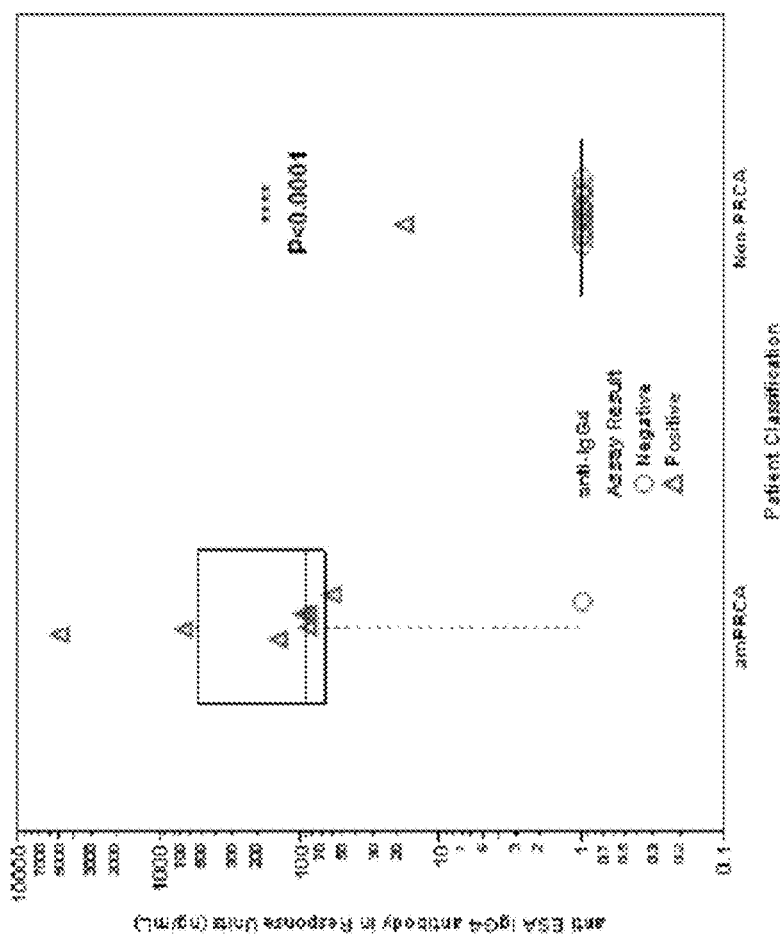

SEQUENCE LISTING

<160> NUMBER OF SEQ ID NOS: 114

<210> SEQ ID NO 1
<211> LENGTH: 744
<212> TYPE: DNA
<213> ORGANISM: Homo sapiens

<400> SEQUENCE: 1

```
agcttcccgg gatgagggcc cccggtgtgg tcacccggcg cgccccaggt cgctgaggga      60
ccccggccag gcgcggagat gggggtgcac gaatgtcctg cctggctgtg gcttctcctg     120
tccctgctgt cgctccctct gggcctccca gtcctgggcg ccccaccacg cctcatctgt     180
gacagccgag tcctggagag gtacctcttg gaggccaagg aggccgagaa tatcacgacg     240
ggctgtgctg aacactgcag cttgaatgag aatatcactg tcccagacac caaagttaat     300
ttctatgcct ggaagaggat ggaggtcggg cagcaggccg tagaagtctg gcagggcctg     360
gccctgctgt cggaagctgt cctgcggggc caggccctgt tggtcaactc ttcccagccg     420
tgggagcccc tgcagctgca tgtggataaa gccgtcagtg gccttcgcag cctcaccact     480
ctgcttcggg ctctgggagc ccaggaagcc atctcccctc cagatgcggc ctcagctgct     540
ccactccgaa caatcactgc tgacactttc cgcaaactct tccgagtcta ctccaatttc     600
ctccggggaa agctgaagct gtacacaggg gaggcctgca ggacagggga cagatgacca     660
ggtgtgtcca cctgggcata tccaccacct ccctcaccaa cattgcttgt gccacaccct     720
cccccgccac tcctgaaccc cgtc                                            744
```

<210> SEQ ID NO 2
<211> LENGTH: 166
<212> TYPE: PRT

<213> ORGANISM: Homo sapiens

<400> SEQUENCE: 2

```
Ala Pro Pro Arg Leu Ile Cys Asp Ser Arg Val Leu Glu Arg Tyr Leu
1               5                   10                  15
Leu Glu Ala Lys Glu Ala Glu Asn Ile Thr Thr Gly Cys Ala Glu His
            20                  25                  30
Cys Ser Leu Asn Glu Asn Ile Thr Val Pro Asp Thr Lys Val Asn Phe
        35                  40                  45
Tyr Ala Trp Lys Arg Met Glu Val Gly Gln Gln Ala Val Glu Val Trp
    50                  55                  60
Gln Gly Leu Ala Leu Leu Ser Glu Ala Val Leu Arg Gly Gln Ala Leu
65                  70                  75                  80
Leu Val Asn Ser Ser Gln Pro Trp Glu Pro Leu Gln Leu His Val Asp
                85                  90                  95
Lys Ala Val Ser Gly Leu Arg Ser Leu Thr Thr Leu Leu Arg Ala Leu
            100                 105                 110
Gly Ala Gln Lys Glu Ala Ile Ser Pro Pro Asp Ala Ala Ser Ala Ala
        115                 120                 125
Pro Leu Arg Thr Ile Thr Ala Asp Thr Phe Arg Lys Leu Phe Arg Val
    130                 135                 140
Tyr Ser Asn Phe Leu Arg Gly Lys Leu Lys Leu Tyr Thr Gly Glu Ala
145                 150                 155                 160
Cys Arg Thr Gly Asp Arg
                165
```

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 3
caggcgagtc aggacattag caacttttg aat          33

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 4
gatgcatcca atttggaaac a          21

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 5
caacagtatg ataatttccc gctcact          27

<210> SEQ ID NO 6
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Ala Ser Gln Asp Ile Ser Asn Phe Leu Asn
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asp Ala Ser Asn Leu Glu Thr
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Gln Tyr Asp Asn Phe Pro Leu Thr
1               5

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
caggcgagtc aggacattag caactattta aat                                33

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gatgcatcca atttggaaac a                                             21

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
caacagtatg atgatctccc gctcact                                       27
```

```
<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Ala Ser Gln Asp Ile Ser Asn Tyr Leu Asn
1               5                   10

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp Ala Ser Asn Leu Glu Thr
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gln Gln Tyr Asp Asp Leu Pro Leu Thr
1               5

<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gggggaaaca acattggaag taaaagtgtg cac                                   33

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gatgatagcg accggccctc a                                                21

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
caggtgtggg atagtagtgg tgatcatccg gta                                   33
```

```
<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Gly Asn Asn Ile Gly Ser Lys Ser Val His
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asp Asp Ser Asp Arg Pro Ser
1               5

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Val Trp Asp Ser Ser Gly Asp His Pro Val
1               5                   10

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
agggccagtc agagggtaa taacaactta gcc                                    33

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ggtgcatcca ccagggccac t                                                21

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
```
cagcagtata atatctggcc tcgcagt                                    27

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Ala Ser Gln Arg Gly Asn Asn Asn Leu Ala
1               5                   10

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Ala Ser Thr Arg Ala Thr
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gln Gln Tyr Asn Ile Trp Pro Arg Ser
1               5

<210> SEQ ID NO 27
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
accctgagca gcggctacag taattataaa gtggac                          36

<210> SEQ ID NO 28
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gtgggcactg gtgggattgt gggatccaag ggggat                          36

<210> SEQ ID NO 29
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ggggcagacc atggcagtgg gagcaacttc gtgtgggtg            39

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Thr Leu Ser Ser Gly Tyr Ser Asn Tyr Lys Val Asp
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Val Gly Thr Gly Gly Ile Val Gly Ser Lys Gly Asp
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Ala Asp His Gly Ser Gly Ser Asn Phe Val Trp Val
1               5                   10

<210> SEQ ID NO 33
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
acctatggta tcaac            15

<210> SEQ ID NO 34
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
tggctcagcg cttacagtgg taacacaaac tatgcacaga aactccaggg c            51

<210> SEQ ID NO 35
<211> LENGTH: 30
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 35
ggagtgggag cttccttta ctttgactac                                         30

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Thr Tyr Gly Ile Asn
1               5

<210> SEQ ID NO 37
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Trp Leu Ser Ala Tyr Ser Gly Asn Thr Asn Tyr Ala Gln Lys Leu Gln
1               5                   10                  15

Gly

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Val Gly Ala Ser Phe Tyr Phe Asp Tyr
1               5                   10

<210> SEQ ID NO 39
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
agctatggca tgaac                                                         15

<210> SEQ ID NO 40
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
tacattagta gtagtagtag taccatatac tacgcagact ctgtgaaggg c                 51

<210> SEQ ID NO 41

```
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gataggatca ccagctggta cgaggaggac tactattact acggtatgga cgtc            54

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ser Tyr Gly Met Asn
1               5

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Tyr Ile Ser Ser Ser Ser Ser Thr Ile Tyr Tyr Ala Asp Ser Val Lys
1               5                   10                  15

Gly

<210> SEQ ID NO 44
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Asp Arg Ile Thr Ser Trp Tyr Glu Glu Asp Tyr Tyr Tyr Tyr Gly Met
1               5                   10                  15

Asp Val

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
agcaacagtg ctgcttggaa c                                               21

<210> SEQ ID NO 46
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 46
aggacatact acaggtccaa gtggtataat gattatgaag tatctgtgaa aagt    54

<210> SEQ ID NO 47
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
gaggaggggt atatagaagc ccactcggtt ccttactttg actac    45

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ser Asn Ser Ala Ala Trp Asn
1               5

<210> SEQ ID NO 49
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Arg Thr Tyr Tyr Arg Ser Lys Trp Tyr Asn Asp Tyr Glu Val Ser Val
1               5                   10                  15
Lys Ser

<210> SEQ ID NO 50
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Glu Glu Gly Tyr Ile Glu Ala His Ser Val Pro Tyr Phe Asp Tyr
1               5                   10                  15

<210> SEQ ID NO 51
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
aactatgcca tgagc    15

<210> SEQ ID NO 52
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
gctgttagtg gtagtggtgg tagcacattc tacgcagact ccatgaaggg c         51

<210> SEQ ID NO 53
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
gaggggctgg agattctgta ctactttgac tac                              33

<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Asn Tyr Ala Met Ser
1               5

<210> SEQ ID NO 55
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ala Val Ser Gly Ser Gly Gly Ser Thr Phe Tyr Ala Asp Ser Met Lys
1               5                   10                  15

Gly

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Glu Gly Leu Glu Ile Leu Tyr Tyr Phe Asp Tyr
1               5                   10

<210> SEQ ID NO 57
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
ggttactact ggagc                                                  15

<210> SEQ ID NO 58
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
gaaatcaatc atagtggaag caccaactac aacccgtccc tcaagagt                    48

<210> SEQ ID NO 59
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
gcaaagttct atggttgggg gaattatccg tttgactcc                              39

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Tyr Tyr Trp Ser
1               5

<210> SEQ ID NO 61
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Glu Ile Asn His Ser Gly Ser Thr Asn Tyr Asn Pro Ser Leu Lys Ser
1               5                   10                  15

<210> SEQ ID NO 62
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ala Lys Phe Tyr Gly Trp Gly Asn Tyr Pro Phe Asp Ser
1               5                   10

<210> SEQ ID NO 63
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Cys Ser Tyr Val Leu Thr Gln Pro Pro Ser Val Ser Val Ala Pro Gly

Gln Thr Ala Arg Ile Thr Cys Gly Gly Asn Asn Ile Gly Ser Lys Ser
                20                  25                  30

Val His Trp Tyr Gln Gln Lys Pro Gly Gln Ala Pro Val Leu Val Val
            35                  40                  45

Tyr Asp Asp Ser Asp Arg Pro Ser Gly Ile Pro Glu Arg Phe Ser Gly
        50                  55                  60

Ser Asn Ser Gly Asn Thr Ala Thr Leu Thr Ile Ser Trp Val Glu Ala
65                  70                  75                  80

Gly Asp Glu Ala Asp Tyr Tyr Cys Gln Val Trp Asp Ser Ser Gly Asp
                85                  90                  95

His Pro Val Phe Gly Gly Gly Thr Lys Leu Thr Val Leu
                100                 105

<210> SEQ ID NO 64
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Thr Ser Tyr Val Leu Thr Gln Pro Pro Ser Val Ser Val Ala Pro Gly
1               5                   10                  15

Gln Thr Ala Arg Ile Thr Cys Gly Gly Asn Asn Ile Gly Ser Lys Ser
                20                  25                  30

Val His Trp Tyr Gln Gln Lys Pro Gly Gln Ala Pro Val Leu Val Val
            35                  40                  45

Tyr Asp Asp Ser Asp Arg Pro Ser Gly Ile Pro Glu Arg Phe Ser Gly
        50                  55                  60

Ser Asn Ser Gly Asn Thr Ala Thr Leu Thr Ile Ser Trp Val Glu Ala
65                  70                  75                  80

Gly Asp Glu Ala Asp Tyr Tyr Cys Gln Val Trp Asp Ser Ser Gly Asp
                85                  90                  95

His Pro Val Phe Gly Gly Gly Thr Lys Leu Thr Val Leu
                100                 105

<210> SEQ ID NO 65
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Arg Gly Asn Asn Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Ile Trp Pro Arg

```
                    85                  90                  95

Ser Phe Gly Gln Gly Thr Lys Leu Glu Ile Lys Arg
                100                 105

<210> SEQ ID NO 66
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Pro Val Leu Thr Gln Pro Pro Ser Ala Ser Ala Ser Leu Gly Ala
1               5                   10                  15

Ser Val Thr Leu Thr Cys Thr Leu Ser Ser Gly Tyr Ser Asn Tyr Lys
                20                  25                  30

Val Asp Trp Tyr Gln Gln Arg Pro Gly Lys Gly Pro Arg Phe Val Met
            35                  40                  45

Arg Val Gly Thr Gly Gly Ile Val Gly Ser Lys Gly Asp Gly Ile Pro
50                  55                  60

Asp Arg Phe Ser Val Leu Gly Ser Gly Leu Asn Arg Tyr Leu Thr Ile
65                  70                  75                  80

Lys Asn Ile Gln Glu Glu Asp Glu Ser Asp Tyr His Cys Gly Ala Asp
                85                  90                  95

His Gly Ser Gly Ser Asn Phe Val Trp Val Phe Gly Gly Thr Lys
                100                 105                 110

Leu Thr Val Leu
        115

<210> SEQ ID NO 67
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Cys Asp Ile Gln Met Thr Gln Ser Pro Ser Ser Leu Ser Ala Ser Val
1               5                   10                  15

Gly Asp Arg Val Thr Ile Thr Cys Gln Ala Ser Gln Asp Ile Ser Asn
                20                  25                  30

Phe Leu Asn Trp Tyr Gln Gln Lys Pro Gly Lys Ala Pro Lys Leu Leu
            35                  40                  45

Ile Tyr Asp Ala Ser Asn Leu Glu Thr Gly Val Pro Ser Arg Phe Ser
50                  55                  60

Gly Ser Gly Ser Gly Thr Asp Phe Thr Phe Thr Ile Ser Ser Leu Gln
65                  70                  75                  80

Pro Glu Asp Val Ala Thr Tyr Tyr Cys Gln Gln Tyr Asp Asn Phe Pro
                85                  90                  95

Leu Thr Phe Gly Gly Gly Thr Lys Val Glu Ile Lys Arg
                100                 105

<210> SEQ ID NO 68
<211> LENGTH: 109
<212> TYPE: PRT
<213> ORGANISM: Artificial Sequence
<220> FEATURE:
<223> OTHER INFORMATION: Description of Artificial Sequence: Synthetic
```

-continued polypeptide

<400> SEQUENCE: 68

Cys Asp Ile Gln Met Thr Gln Ser Pro Ser Ser Leu Ser Ala Ser Val
1               5                   10                  15

Gly Asp Arg Val Thr Ile Thr Cys Gln Ala Ser Gln Asp Ile Ser Asn
            20                  25                  30

Tyr Leu Asn Trp Phe Gln Gln Lys Pro Gly Lys Ala Pro Asn Leu Leu
        35                  40                  45

Ile Tyr Asp Ala Ser Asn Leu Glu Thr Gly Val Pro Ser Arg Phe Ser
    50                  55                  60

Gly Gly Gly Ser Gly Thr Asp Phe Thr Phe Thr Ile Ser Ser Leu Gln
65                  70                  75                  80

Pro Glu Asp Ile Ala Thr Tyr Tyr Cys Gln Gln Tyr Asp Asp Leu Pro
                85                  90                  95

Leu Thr Phe Gly Gly Gly Thr Lys Val Glu Ile Lys Arg
            100                 105

<210> SEQ ID NO 69
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Cys Gln Val Gln Leu Gln Gln Ser Gly Pro Gly Leu Val Lys Pro Ser
1               5                   10                  15

Gln Thr Leu Ser Leu Thr Cys Ala Ile Ser Gly Asp Ser Val Ser Ser
            20                  25                  30

Asn Ser Ala Ala Trp Asn Trp Ile Arg Gln Ser Pro Ser Arg Gly Leu
        35                  40                  45

Glu Trp Leu Gly Arg Thr Tyr Tyr Arg Ser Lys Trp Tyr Asn Asp Tyr
    50                  55                  60

Glu Val Ser Val Lys Ser Arg Ile Ile Ile Asn Pro Asp Thr Ser Lys
65                  70                  75                  80

Asn Gln Phe Ser Leu Gln Leu Asn Ser Val Thr Pro Glu Asp Thr Ala
                85                  90                  95

Val Tyr Tyr Cys Ala Arg Glu Glu Gly Tyr Ile Glu Ala His Ser Val
            100                 105                 110

Pro Tyr Phe Asp Tyr Trp Gly Gln Gly Thr Leu Val Thr Val Ser Ser
        115                 120                 125

<210> SEQ ID NO 70
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Ser Gln Val Gln Leu Gln Gln Ser Gly Pro Gly Leu Val Lys Pro Ser
1               5                   10                  15

Gln Thr Leu Ser Leu Thr Cys Ala Ile Ser Gly Asp Ser Val Ser Ser
            20                  25                  30

Asn Ser Ala Ala Trp Asn Trp Ile Arg Gln Ser Pro Ser Arg Gly Leu
        35                  40                  45

Glu Trp Leu Gly Arg Thr Tyr Tyr Arg Ser Lys Trp Tyr Asn Asp Tyr
                50                  55                  60

Glu Val Ser Val Lys Ser Arg Ile Ile Ile Asn Pro Asp Thr Ser Lys
65                  70                  75                  80

Asn Gln Phe Ser Leu Gln Leu Asn Ser Val Thr Pro Glu Asp Thr Ala
                85                  90                  95

Val Tyr Tyr Cys Ala Arg Glu Glu Gly Tyr Ile Glu Ala His Ser Val
            100                 105                 110

Pro Tyr Phe Asp Tyr Trp Gly Gln Gly Thr Leu Val Thr Val Ser Ser
        115                 120                 125

<210> SEQ ID NO 71
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
                20                  25                  30

Ala Met Ser Trp Val Arg Gln Ala Pro Gly Lys Gly Leu Glu Trp Val
            35                  40                  45

Ser Ala Val Ser Gly Ser Gly Gly Ser Thr Phe Tyr Ala Asp Ser Met
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Glu Gly Leu Glu Ile Leu Tyr Tyr Phe Asp Tyr Trp Gly Gln
            100                 105                 110

Gly Thr Leu Val Thr Val Ser Ser
        115                 120

<210> SEQ ID NO 72
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
                20                  25                  30

Ala Met Ser Trp Val Arg Gln Ala Pro Gly Lys Gly Leu Glu Trp Val
            35                  40                  45

Ser Ala Val Ser Gly Ser Gly Gly Ser Thr Phe Tyr Ala Asp Ser Met
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Glu Gly Leu Glu Ile Leu Tyr Tyr Phe Asp Tyr Trp Gly Gln
            100                 105                 110

Gly Thr Leu Val Thr Val Ser Ser
        115                 120

<210> SEQ ID NO 73
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Lys Phe Tyr Gly Trp Gly Asn Tyr Pro Phe Asp Ser Trp Gly
            100                 105                 110

Gln Gly Thr Leu Val Thr Val Ser Ser
        115                 120

<210> SEQ ID NO 74
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Lys Phe Tyr Gly Trp Gly Asn Tyr Pro Phe Asp Ser Trp Gly
            100                 105                 110

Gln Gly Thr Leu Val Thr Val Ser Ser
        115                 120

<210> SEQ ID NO 75

```
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Cys Gln Val Gln Leu Val Gln Ser Gly Ala Glu Val Lys Lys Pro Gly
1               5                   10                  15

Ala Ser Val Lys Val Ser Cys Lys Ala Ser Gly Tyr Thr Phe Thr Thr
            20                  25                  30

Tyr Gly Ile Asn Trp Val Arg Gln Ala Pro Gly Gln Gly Leu Glu Trp
        35                  40                  45

Met Gly Trp Leu Ser Ala Tyr Ser Gly Asn Thr Asn Tyr Ala Gln Lys
    50                  55                  60

Leu Gln Gly Arg Val Thr Met Thr Thr Asp Thr Ser Thr Ser Thr Ala
65                  70                  75                  80

Tyr Met Glu Leu Arg Ser Leu Arg Ser Asp Asp Thr Ala Val Tyr Tyr
                85                  90                  95

Cys Ala Arg Gly Val Gly Ala Ser Phe Tyr Phe Asp Tyr Trp Gly Gln
            100                 105                 110

Gly Thr Leu Val Thr Val Ser Ser
        115                 120

<210> SEQ ID NO 76
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Cys Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser Ser
            20                  25                  30

Tyr Gly Met Asn Trp Val Arg Gln Ala Pro Gly Lys Gly Leu Glu Trp
        35                  40                  45

Val Ser Tyr Ile Ser Ser Ser Ser Thr Ile Tyr Tyr Ala Asp Ser
    50                  55                  60

Val Lys Gly Arg Phe Thr Ile Ser Arg Asp Asn Ala Lys Asn Ser Leu
65                  70                  75                  80

Tyr Leu Gln Met Asn Ser Leu Arg Asp Glu Asp Thr Ala Val Tyr Tyr
                85                  90                  95

Cys Ala Arg Asp Arg Ile Thr Ser Trp Tyr Glu Glu Asp Tyr Tyr Tyr
            100                 105                 110

Tyr Gly Met Asp Val Trp Gly Gln Gly Thr Thr Val Thr Val Ser Ser
        115                 120                 125

<210> SEQ ID NO 77
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 77
```

His His His His His His
1               5

<210> SEQ ID NO 78
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Asp Tyr Lys Asp Asp Asp Asp Lys His His His His His His
1               5                   10

<210> SEQ ID NO 79
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Met Asp Met Arg Val Pro Ala Gln Leu Leu Gly Leu Leu Leu Leu Trp
1               5                   10                  15

Leu Arg Gly Ala Arg Cys Ser Tyr Val Leu Thr Gln Pro Pro Ser Val
                20                  25                  30

Ser Val Ala Pro Gly Gln Thr Ala Arg Ile Thr Cys Gly Gly Asn Asn
            35                  40                  45

Ile Gly Ser Lys Ser Val His Trp Tyr Gln Gln Lys Pro Gly Gln Ala
    50                  55                  60

Pro Val Leu Val Val Tyr Asp Asp Ser Asp Arg Pro Ser Gly Ile Pro
65                  70                  75                  80

Glu Arg Phe Ser Gly Ser Asn Ser Gly Asn Thr Ala Thr Leu Thr Ile
                85                  90                  95

Ser Trp Val Glu Ala Gly Asp Glu Ala Asp Tyr Tyr Cys Gln Val Trp
                100                 105                 110

Asp Ser Ser Gly Asp His Pro Val Phe Gly Gly Gly Thr Lys Leu Thr
            115                 120                 125

Val Leu Gly Gln Pro Lys Ala Asn Pro Thr Val Thr Leu Phe Pro Pro
    130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Gly
                165                 170                 175

Ser Pro Val Lys Ala Gly Val Glu Thr Thr Lys Pro Ser Lys Gln Ser
            180                 185                 190

Asn Asn Lys Tyr Ala Ala Ser Ser Tyr Leu Ser Leu Thr Pro Glu Gln
    195                 200                 205

Trp Lys Ser His Arg Ser Tyr Ser Cys Gln Val Thr His Glu Gly Ser
210                 215                 220

Thr Val Glu Lys Thr Val Ala Pro Thr Glu Cys Ser
225                 230                 235

<210> SEQ ID NO 80
<211> LENGTH: 711
<212> TYPE: DNA
<213> ORGANISM: Artificial Sequence
<220> FEATURE:

<223> OTHER INFORMATION: Description of Artificial Sequence: Synthetic
    polynucleotide

<400> SEQUENCE: 80

```
atggacatga gggtgcccgc tcagctcctg gggctcctgc tgctgtggct gagaggtgcg      60
cgctgttcct atgtgctgac tcagccaccc tcggtgtcag tggccccagg acagacggcc     120
aggattacct gtggggggaaa caacattgga agtaaaagtg tgcactggta ccagcagaag     180
ccaggccagg cccctgtgct ggtcgtctat gatgatagcg accggccctc agggatccct     240
gagcgattct ctggctccaa ctctgggaac acggccaccc tgaccatcag ctgggtcgaa     300
gccggggatg aggccgacta ttactgtcag gtgtgggata gtagtggtga tcatccggta     360
ttcggcggag ggaccaagct gaccgtccta ggtcagccca aggccaaccc cactgtcact     420
ctgttcccgc cctcctctga ggagctcaa gccaacaagg ccacactagt gtgtctgatc     480
agtgacttct acccgggagc tgtgacagtg gcctggaagg cagatggcag ccccgtcaag     540
gcgggagtgg agaccaccaa accctccaaa cagagcaaca caagtacgc ggccagcagc     600
tacctgagcc tgacgcccga gcagtggaag tcccacagaa gctacagctg ccaggtcacg     660
catgaaggga gcaccgtgga agacagtgtg cccctacag aatgttcatg a             711
```

<210> SEQ ID NO 81
<211> LENGTH: 479
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 81

Met Asp Met Arg Val Pro Ala Gln Leu Leu Gly Leu Leu Leu Leu Trp
1               5                  10                  15

Leu Arg Gly Ala Arg Cys Gln Val Gln Leu Gln Gln Ser Gly Pro Gly
            20                  25                  30

Leu Val Lys Pro Ser Gln Thr Leu Ser Leu Thr Cys Ala Ile Ser Gly
        35                  40                  45

Asp Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80

Trp Tyr Asn Asp Tyr Glu Val Ser Val Lys Ser Arg Ile Ile Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Arg Glu Glu Gly Tyr Ile
        115                 120                 125

Glu Ala His Ser Val Pro Tyr Phe Asp Tyr Trp Gly Gln Gly Thr Leu
    130                 135                 140

Val Thr Val Ser Ser Ala Ser Thr Lys Gly Pro Ser Val Phe Pro Leu
145                 150                 155                 160

Ala Pro Ser Ser Lys Ser Thr Ser Gly Gly Thr Ala Ala Leu Gly Cys
                165                 170                 175

Leu Val Lys Asp Tyr Phe Pro Glu Pro Val Thr Val Ser Trp Asn Ser
            180                 185                 190

Gly Ala Leu Thr Ser Gly Val His Thr Phe Pro Ala Val Leu Gln Ser
        195                 200                 205

Ser Gly Leu Tyr Ser Leu Ser Ser Val Val Thr Val Pro Ser Ser Ser
    210                 215                 220

Leu Gly Thr Gln Thr Tyr Ile Cys Asn Val Asn His Lys Pro Ser Asn
225                 230                 235                 240

Thr Lys Val Asp Lys Lys Val Glu Pro Lys Ser Cys Asp Lys Thr His
                245                 250                 255

Thr Cys Pro Pro Cys Pro Ala Pro Glu Leu Leu Gly Gly Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
    290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Lys Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Arg Glu Glu Met Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Lys
465                 470                 475

<210> SEQ ID NO 82
<211> LENGTH: 1440
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82
atggacatga gggtgcccgc tcagctcctg gggctcctgc tgctgtggct gagaggtgcg      60
cgctgtcagg tacagctgca gcagtcaggt ccaggactgg tgaagccctc gcagaccctc     120
tcactcacct gtgccatctc cggggacagt gtctctagca acagtgctgc ttggaactgg     180
atcaggcagt ccccatcgag aggccttgag tggctgggaa ggacatacta caggtccaag     240
tggtataatg attatgaagt atctgtgaaa agtcgaataa tcatcaaccc agacacatcc     300
aagaaccagt tctccctgca gctgaactct gtgactcccg aggacacggc tgtgtattac     360
tgtgcaaggg aggagggta tatagaagcc cactcggttc cttactttga ctactggggc     420
cagggaaccc tggtcaccgt ctctagtgcc tccaccaagg gcccatcggt cttccccctg     480
gcaccctcct ccaagagcac ctctgggggc acagcggccc tgggctgcct ggtcaaggac     540

-continued

```
tacttccccg aaccggtgac ggtgtcgtgg aactcaggcg ccctgaccag cggcgtgcac      600
accttcccgg ctgtcctaca gtcctcagga ctctactccc tcagcagcgt ggtgaccgtg      660
ccctccagca gcttgggcac ccagacctac atctgcaacg tgaatcacaa gcccagcaac      720
accaaggtgg acaagaaagt tgagcccaaa tcttgtgaca aaactcacac atgcccaccg      780
tgcccagcac ctgaactcct ggggggaccg tcagtcttcc tcttccccc  aaaacccaag      840 gacaccctca tgatctcccg gacccctgag gtcacatgcg tggtggtgga cgtgagccac      900
gaagaccctg aggtcaagtt caactggtac gtggacggcg tggaggtgca taatgccaag      960
acaaagccgc gggaggagca gtacaacagc acgtaccgtg tggtcagcgt cctcaccgtc     1020
ctgcaccagg actggctgaa tggcaaggag tacaagtgca aggtctccaa caaagccctc     1080
ccagccccca tcgagaaaac catctccaaa gccaaagggc agccccgaga accacaggtg     1140
tacaccctgc cccatcccg  ggaggagatg accaagaacc aggtcagcct gacctgcctg     1200
gtcaaaggct tctatcccag cgacatcgcc gtggagtggg agagcaatgg gcagccggag     1260
aacaactaca agaccacgcc tcccgtgctg gactccgacg gctccttctt cctctatagc     1320
aagctcaccg tggacaagag caggtggcag caggggaacg tcttctcatg ctccgtgatg     1380
catgaggctc tgcacaacca ctacacgcag aagagcctct ccctgtctcc gggtaaatga    1440
```

<210> SEQ ID NO 83
<211> LENGTH: 479
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Met Asp Met Arg Val Pro Ala Gln Leu Leu Gly Leu Leu Leu Leu Trp
1               5                   10                  15

Leu Arg Gly Ala Arg Cys Gln Val Gln Leu Gln Gln Ser Gly Pro Gly
            20                  25                  30

Leu Val Lys Pro Ser Gln Thr Leu Ser Leu Thr Cys Ala Ile Ser Gly
        35                  40                  45

Asp Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80

Trp Tyr Asn Asp Tyr Glu Val Ser Val Lys Ser Arg Ile Ile Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Arg Glu Glu Gly Tyr Ile
        115                 120                 125

Glu Ala His Ser Val Pro Tyr Phe Asp Tyr Trp Gly Gln Gly Thr Leu
    130                 135                 140

Val Thr Val Ser Ser Ala Ser Thr Lys Gly Pro Ser Val Phe Pro Leu
145                 150                 155                 160

Ala Pro Ser Ser Lys Ser Thr Ser Gly Gly Thr Ala Ala Leu Gly Cys
                165                 170                 175

Leu Val Lys Asp Tyr Phe Pro Glu Pro Val Thr Val Ser Trp Asn Ser
            180                 185                 190

Gly Ala Leu Thr Ser Gly Val His Thr Phe Pro Ala Val Leu Gln Ser

|   |   |   | 195 |   |   |   | 200 |   |   |   | 205 |   |
|---|---|---|---|---|---|---|---|---|---|---|---|---|

Ser Gly Leu Tyr Ser Leu Ser Ser Val Val Thr Val Pro Ser Ser
210                 215                 220

Leu Gly Thr Gln Thr Tyr Ile Cys Asn Val Asn His Lys Pro Ser Asn
225                 230                 235                 240

Thr Lys Val Asp Lys Lys Val Glu Pro Lys Ser Cys Asp Lys Thr His
                245                 250                 255

Thr Cys Pro Pro Cys Pro Ala Pro Glu Leu Leu Gly Gly Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
    290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Lys Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Arg Glu Glu Met Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Lys
465                 470                 475

<210> SEQ ID NO 84
<211> LENGTH: 1440
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 84
atggacatga gggtgcccgc tcagctcctg gggctcctgc tgctgtggct gagaggtgcg      60
cgctgtcagg tacagctgca gcagtcaggt ccaggactgg tgaagccctc gcagaccctc     120
tcactcacct gtgccatctc cggggacagt gtctctagca acagtgctgc ttggaactgg     180
atcaggcagt cccatcgag aggccttgag tggctgggaa ggacatacta caggtccaag     240
tggtataatg attatgaagt atctgtgaaa agtcgaataa tcatcaaccc agacacatcc     300
aagaaccagt tctccctgca gctgaactct gtgactcccg aggacacggc tgtgtattac     360
tgtgcaaggg aggagggta tatagaagcc cactcggttc cttactttga ctactggggc     420
cagggaaccc tggtcaccgt ctctagtgcc tccaccaagg gcccatcggt cttccccctg     480

```
gcaccctcct ccaagagcac ctctgggggc acagcggccc tgggctgcct ggtcaaggac      540
tacttccccg aaccggtgac ggtgtcgtgg aactcaggcg ccctgaccag cggcgtgcac      600
accttcccgg ctgtcctaca gtcctcagga ctctactccc tcagcagcgt ggtgaccgtg      660
ccctccagca gcttgggcac ccagacctac atctgcaacg tgaatcacaa gcccagcaac      720
accaaggtgg acaagaaagt tgagcccaaa tcttgtgaca aaactcacac atgcccaccg      780
tgcccagcac ctgaactcct ggggggaccg tcagtcttcc tcttccccccc aaaacccaag     840 gacaccctca tgatctcccg gacccctgag gtcacatgcg tggtggtgga cgtgagccac      900
gaagaccctg aggtcaagtt caactggtac gtggacggcg tggaggtgca taatgccaag      960
acaaagccgc gggaggagca gtacaacagc acgtaccgtg tggtcagcgt cctcaccgtc     1020
ctgcaccagg actggctgaa tggcaaggag tacaagtgca aggtctccaa caaagccctc     1080
ccagccccca tcgagaaaac catctccaaa gccaagggc agccccgaga ccacaggtg      1140 tacaccctgc ccccatcccg ggaggagatg accaagaacc aggtcagcct gacctgcctg     1200
gtcaaaggct tctatcccag cgacatcgcc gtggagtggg agagcaatgg gcagccggag     1260
aacaactaca agaccacgcc tcccgtgctg gactccgacg gctccttctt cctctatagc     1320
aagctcaccg tggacaagag caggtggcag caggggaacg tcttctcatg ctccgtgatg     1380
catgaggctc tgcacaacca ctacacgcag aagagcctct ccctgtctcc gggtaaatga     1440
```

<210> SEQ ID NO 85
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

```
Met Ala Trp Ile Thr Leu Leu Gly Leu Leu Ser His Cys Thr Asp
1               5                   10                  15

Ser Val Thr Ser Tyr Val Leu Thr Gln Pro Pro Ser Val Ser Val Ala
            20                  25                  30

Pro Gly Gln Thr Ala Arg Ile Thr Cys Gly Gly Asn Asn Ile Gly Ser
        35                  40                  45

Lys Ser Val His Trp Tyr Gln Gln Lys Pro Gly Gln Ala Pro Val Leu
    50                  55                  60

Val Val Tyr Asp Asp Ser Asp Arg Pro Ser Gly Ile Pro Glu Arg Phe
65                  70                  75                  80

Ser Gly Ser Asn Ser Gly Asn Thr Ala Thr Leu Thr Ile Ser Trp Val
                85                  90                  95

Glu Ala Gly Asp Glu Ala Asp Tyr Tyr Cys Gln Val Trp Asp Ser Ser
            100                 105                 110

Gly Asp His Pro Val Phe Gly Gly Gly Thr Lys Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190
```

```
Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
        210                 215                 220

Lys Thr Val Ala Pro Thr Glu Cys Ser
225                 230

<210> SEQ ID NO 86
<211> LENGTH: 702
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86
atggcatgga tcactctcct cctcggcctc ctctctcact gcacagactc tgtgacctcc     60
tatgtgctga ctcagccacc ctcggtgtca gtggccccag gacagacggc caggattacc    120
tgtgggggaa acaacattgg aagtaaaagt gtgcactggt accagcagaa gccaggccag    180
gcccctgtgc tggtcgtcta tgatgatagc accggccct cagggatccc tgagcgattc    240
tctggctcca actctgggaa cacggccacc ctgaccatca gctgggtcga agccggggat    300
gaggccgact attactgtca ggtgtgggat agtagtggtg atcatccggt attcggcgga    360
gggaccaagc tgaccgtcct aggtcagccc aaggctgccc cctcggtcac tctgttccct    420
ccctctagcg aggagcttca agccaacaag gccacactgg tgtgtctcat aagtgacttc    480
tacccgggag ccgtgacagt ggcctggaag gcagatagca gccccgtcaa ggcgggagtg    540
gagaccacca cccctccaa acaaagcaac aacaagtacg cggccagcag ctatctgagc    600
ctgacgcctg agcagtggaa gtcccacaga agctacagct gccaggtcac gcatgaaggg    660
agcaccgtgg agaagacagt ggcccctaca gaatgttcat ag                       702

<210> SEQ ID NO 87
<211> LENGTH: 474
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Met Ser Val Ser Phe Leu Ile Phe Leu Pro Val Leu Gly Leu Pro Trp
1               5                   10                  15

Gly Val Leu Ser Gln Val Gln Leu Gln Gln Ser Gly Pro Gly Leu Val
            20                  25                  30

Lys Pro Ser Gln Thr Leu Ser Leu Thr Cys Ala Ile Ser Gly Asp Ser
        35                  40                  45

Val Ser Ser Asn Ser Ala Ala Trp Asn Trp Ile Arg Gln Ser Pro Ser
    50                  55                  60

Arg Gly Leu Glu Trp Leu Gly Arg Thr Tyr Tyr Arg Ser Lys Trp Tyr
65                  70                  75                  80

Asn Asp Tyr Glu Val Ser Val Lys Ser Arg Ile Ile Ile Asn Pro Asp
                85                  90                  95

Thr Ser Lys Asn Gln Phe Ser Leu Gln Leu Asn Ser Val Thr Pro Glu
            100                 105                 110

Asp Thr Ala Val Tyr Tyr Cys Ala Arg Glu Gly Tyr Ile Glu Ala
        115                 120                 125
```

His Ser Val Pro Tyr Phe Asp Tyr Trp Gly Gln Gly Thr Leu Val Thr
    130                 135                 140

Val Ser Ser Ala Ser Thr Lys Gly Pro Ser Val Phe Pro Leu Ala Pro
145                 150                 155                 160

Cys Ser Arg Ser Thr Ser Glu Ser Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
        195                 200                 205

Leu Tyr Ser Leu Ser Ser Val Val Thr Val Pro Ser Ser Ser Leu Gly
    210                 215                 220

Thr Lys Thr Tyr Thr Cys Asn Val Asp His Lys Pro Ser Asn Thr Lys
225                 230                 235                 240

Val Asp Lys Arg Val Glu Ser Lys Tyr Gly Pro Pro Cys Pro Ser Cys
                245                 250                 255

Pro Ala Pro Glu Phe Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser Gln Glu Asp Pro Glu Val Gln Phe Asn Trp
    290                 295                 300

Tyr Val Asp Gly Val Glu Val His Asn Ala Lys Thr Lys Pro Arg Glu
305                 310                 315                 320

Glu Gln Phe Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Gly Leu Pro Ser Ser Ile Glu Lys Thr Ile Ser Lys Ala Lys Gly
        355                 360                 365

Gln Pro Arg Glu Pro Gln Val Tyr Thr Leu Pro Pro Ser Gln Glu Glu
    370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Arg Leu Thr Val Asp Lys Ser Arg Trp Gln Glu Gly Asn
        435                 440                 445

Val Phe Ser Cys Ser Val Met His Glu Ala Leu His Asn His Tyr Thr
    450                 455                 460

Gln Lys Ser Leu Ser Leu Ser Leu Gly Lys
465                 470

<210> SEQ ID NO 88
<211> LENGTH: 2033
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88
atgtctgtct ccttcctcat cttcctgccc gtgctgggcc tcccatgggg tgtcctgtca    60

```
caggtacagc tgcagcagtc aggtccagga ctggtgaagc cctcgcagac cctctcactc    120
acctgtgcca tctccgggga cagtgtctct agcaacagtg ctgcttggaa ctggatcagg    180
cagtccccat cgagaggcct tgagtggctg ggaaggacat actacaggtc aagtggtat     240
aatgattatg aagtatctgt gaaaagtcga ataatcatca acccagacac atccaagaac    300
cagttctccc tgcagctgaa ctctgtgact cccgaggaca cggctgtgta ttactgtgca    360
agggaggagg ggtatataga agcccactcg gttccttact ttgactactg gggccaggga    420
accctggtca ccgtctcctc agcttccacc aagggcccat ccgtcttccc cctggcgccc    480
tgctctagaa gcacctccga gagcacagcc gccctgggct gcctggtcaa ggactacttc    540
cccgaaccgg tgacggtgtc gtggaactca ggcgccctga ccagcggcgt gcacaccttc    600
ccggctgtcc tacagtcctc aggactctac tccctcagca gcgtggtgac cgtgccctcc    660
agcagcttgg gcacgaagac ctacacctgc aacgtagatc acaagcccag caacaccaag    720
gtggacaaga gagttggtga gaggccagca caggagggga gggtgtctgc tggaagccag    780
gctcagccct cctgcctgga cgcaccccgg ctgtgcagcc ccagcccagg cagcaaggc    840
atgccccatc tgtctcctca cccggaggcc tctgaccacc ccactcatgc tcagggagag    900
ggtcttctgg atttttccac caggctccgg gcagccacag gctggatgcc ctacccag    960
gccctgcgca tacaggggca ggtgctgcgc tcagacctgc caagagccat atccgggagg    1020
accctgcccc tgacctaagc ccaccccaaa ggccaaactc tccactccct cagctcagac    1080
accttctctc ctcccagatc tgagtaactc ccaatcttct ctctgcagag tccaaatatg    1140
gtcccccatg cccatcatgc ccaggtaagc caacccaggc ctcgccctcc agctcaaggc    1200
gggacaggtg ccctagagta gcctgcatcc agggacaggc cccagccggg gtgctgacgc    1260
atccacctcc atctcttcct cagcacctga gttcctgggg ggaccatcag tcttcctgtt    1320
cccccccaaaa cccaaggaca ctctcatgat ctcccggacc cctgaggtca cgtgcgtggt    1380
ggtggacgtg agccaggaag accccgaggt ccagttcaac tggtacgtgg atggcgtgga    1440
ggtgcataat gccaagacaa agccgcggga ggagcagttc aacagcacgt accgtgtggt    1500
cagcgtcctc accgtcctgc accaggactg gctgaacggc aaggagtaca agtgcaaggt    1560
ctccaacaaa ggcctcccgt cctccatcga gaaaaccatc tccaaagcca aggtgggac    1620
ccacggggtg cgagggccac acggacagag gccagctcgg cccaccctct gccctgggag    1680
tgaccgctgt gccaacctct gtccctacag ggcagccccg agagccacag gtgtacaccc    1740
tgcccccatc caggaggag atgaccaaga accaggtcag cctgacctgc ctggtcaaag    1800
gcttctaccc cagcgacatc gccgtggagt gggagagcaa tgggcagccg gagaacaact    1860
acaagaccac gcctcccgtg ctggactccg acggctcctt cttcctctac agcaggctaa    1920
ccgtggacaa gagcaggtgg caggagggga atgtcttctc atgctccgtg atgcatgagg    1980
ctctgcacaa ccactacaca cagaagagcc tctccctgtc tctgggtaaa tga            2033
```

<210> SEQ ID NO 89
<211> LENGTH: 233
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 89

Met Ala Trp Ile Thr Leu Leu Leu Gly Leu Leu Ser His Cys Thr Asp

```
1               5                   10                  15
Ser Val Thr Ser Tyr Val Leu Thr Gln Pro Pro Ser Val Ser Val Ala
            20                  25                  30
Pro Gly Gln Thr Ala Arg Ile Thr Cys Gly Gly Asn Asn Ile Gly Ser
        35                  40                  45
Lys Ser Val His Trp Tyr Gln Gln Lys Pro Gly Gln Ala Pro Val Leu
    50                  55                  60
Val Val Tyr Asp Asp Ser Asp Arg Pro Ser Gly Ile Pro Glu Arg Phe
65                  70                  75                  80
Ser Gly Ser Asn Ser Gly Asn Thr Ala Thr Leu Thr Ile Ser Trp Val
                85                  90                  95
Glu Ala Gly Asp Glu Ala Asp Tyr Tyr Cys Gln Val Trp Asp Ser Ser
            100                 105                 110
Gly Asp His Pro Val Phe Gly Gly Gly Thr Lys Leu Thr Val Leu Gly
        115                 120                 125
Gln Pro Lys Ala Ala Pro Ser Val Thr Leu Phe Pro Pro Ser Ser Glu
    130                 135                 140
Glu Leu Gln Ala Asn Lys Ala Thr Leu Val Cys Leu Ile Ser Asp Phe
145                 150                 155                 160
Tyr Pro Gly Ala Val Thr Val Ala Trp Lys Ala Asp Ser Ser Pro Val
                165                 170                 175
Lys Ala Gly Val Glu Thr Thr Thr Pro Ser Lys Gln Ser Asn Asn Lys
            180                 185                 190
Tyr Ala Ala Ser Ser Tyr Leu Ser Leu Thr Pro Glu Gln Trp Lys Ser
        195                 200                 205
His Arg Ser Tyr Ser Cys Gln Val Thr His Glu Gly Ser Thr Val Glu
    210                 215                 220
Lys Thr Val Ala Pro Thr Glu Cys Ser
225                 230
```

<210> SEQ ID NO 90
<211> LENGTH: 702
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90

```
atggcatgga tcactctcct cctcggcctc ctctctcact gcacagactc tgtgacctcc    60
tatgtgctga ctcagccacc ctcggtgtca gtggccccag acagacggc caggattacc   120
tgtgggggaa acaacattgg aagtaaaagt gtgcactggt accagcagaa gccaggccag   180
gcccctgtgc tggtcgtcta tgatgatagc accggccct cagggatccc tgagcgattc   240
tctggctcca actctgggaa cacggccacc ctgaccatca gctgggtcga gccggggat   300
gaggccgact attactgtca ggtgtgggat agtagtggtg atcatccggt attcggcgga   360
gggaccaagc tgaccgtcct aggtcagccc aaggctgccc cctcggtcac tctgttccct   420
ccctctagcg aggagcttca agccaacaag gccacactgg tgtgtctcat aagtgacttc   480
tacccgggag ccgtgacagt ggcctggaag gcagatagca gccccgtcaa ggcgggagtg   540
gagaccacca cacctccaa acaaagcaac aacaagtacg cggccagcag ctatctgagc   600
ctgacgcctg agcagtggaa gtcccacaga agctacagct gccaggtcac gcatgaaggg   660
agcaccgtgg agaagacagt ggcccctaca gaatgttcat ag                     702
```

<210> SEQ ID NO 91
<211> LENGTH: 474
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 91

```
Met Ser Val Ser Phe Leu Ile Phe Leu Pro Val Leu Gly Leu Pro Trp
1               5                   10                  15

Gly Val Leu Ser Gln Val Gln Leu Gln Gln Ser Gly Pro Gly Leu Val
            20                  25                  30

Lys Pro Ser Gln Thr Leu Ser Leu Thr Cys Ala Ile Ser Gly Asp Ser
        35                  40                  45

Val Ser Ser Asn Ser Ala Ala Trp Asn Trp Ile Arg Gln Ser Pro Ser
    50                  55                  60

Arg Gly Leu Glu Trp Leu Gly Arg Thr Tyr Tyr Arg Ser Lys Trp Tyr
65                  70                  75                  80

Asn Asp Tyr Glu Val Ser Val Lys Ser Arg Ile Ile Ile Asn Pro Asp
                85                  90                  95

Thr Ser Lys Asn Gln Phe Ser Leu Gln Leu Asn Ser Val Thr Pro Glu
            100                 105                 110

Asp Thr Ala Val Tyr Tyr Cys Ala Arg Glu Glu Gly Tyr Ile Glu Ala
        115                 120                 125

His Ser Val Pro Tyr Phe Asp Tyr Trp Gly Gln Gly Thr Leu Val Thr
    130                 135                 140

Val Ser Ser Ala Ser Thr Lys Gly Pro Ser Val Phe Pro Leu Ala Pro
145                 150                 155                 160

Cys Ser Arg Ser Thr Ser Glu Ser Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
        195                 200                 205

Leu Tyr Ser Leu Ser Ser Val Val Thr Val Pro Ser Ser Ser Leu Gly
    210                 215                 220

Thr Lys Thr Tyr Thr Cys Asn Val Asp His Lys Pro Ser Asn Thr Lys
225                 230                 235                 240

Val Asp Lys Arg Val Glu Ser Lys Tyr Gly Pro Pro Cys Pro Ser Cys
                245                 250                 255

Pro Ala Pro Glu Phe Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser Gln Glu Asp Pro Glu Val Gln Phe Asn Trp
    290                 295                 300

Tyr Val Asp Gly Val Glu Val His Asn Ala Lys Thr Lys Pro Arg Glu
305                 310                 315                 320

Glu Gln Phe Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Gly Leu Pro Ser Ser Ile Glu Lys Thr Ile Ser Lys Ala Lys Gly
        355                 360                 365
```

```
Gln Pro Arg Glu Pro Gln Val Tyr Thr Leu Pro Pro Ser Gln Glu Glu
    370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Arg Leu Thr Val Asp Lys Ser Arg Trp Gln Glu Gly Asn
        435                 440                 445

Val Phe Ser Cys Ser Val Met His Glu Ala Leu His Asn His Tyr Thr
    450                 455                 460

Gln Lys Ser Leu Ser Leu Ser Leu Gly Lys
465                 470

<210> SEQ ID NO 92
<211> LENGTH: 1425
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92
atgtctgtct ccttcctcat cttcctgccc gtgctgggcc tcccatgggg tgtcctgtca      60
caggtacagc tgcagcagtc aggtccagga ctggtgaagc cctcgcagac cctctcactc     120
acctgtgcca tctccgggga cagtgtctct agcaacagtg ctgcttggaa ctggatcagg     180
cagtccccat cgagaggcct tgagtggctg gaaggacat actacaggtc caagtggtat      240
aatgattatg aagtatctgt gaaaagtcga ataatcatca cccagacac atccaagaac      300 cagttctccc tgcagctgaa ctctgtgact cccgaggaca cggctgtgta ttactgtgca     360
agggaggagg gtatataga gcccactcg gttccttact ttgactactg gggccaggga      420
accctggtca ccgtctctag tgcttccacc aagggcccat ccgtcttccc cctggcgccc     480
tgctccagga gcacctccga gagcacagcc gccctgggct gcctggtcaa ggactacttc     540
cccgaaccgg tgacggtgtc gtggaactca ggcgccctga ccagcggcgt gcacaccttc     600
ccggctgtcc tacagtcctc aggactctac tccctcagca gcgtggtgac cgtgccctcc     660
agcagcttgg gcacgaagac ctacacctgc aacgtagatc acaagcccag caacaccaag     720
gtggacaaga gagttgagtc caaatatggt ccccccatgcc catcatgccc agcacctgag     780
ttcctggggg gaccatcagt cttcctgttc cccccaaaac ccaaggacac tctcatgatc     840
tcccggaccc ctgaggtcac gtgcgtggtg gtggacgtga gccaggaaga ccccgaggtc     900
cagttcaact ggtacgtgga tggcgtggag gtgcataatg ccaagacaaa gccgcgggag     960
gagcagttca acagcacgta ccgtgtggtc agcgtcctca ccgtcctgca ccaggactgg    1020
ctgaacggca aggagtacaa gtgcaaggtc tccaacaaag gcctcccgtc ctccatcgag    1080
aaaaccatct ccaaagccaa agggcagccc cgagagccac aggtgtacac cctgcccca     1140 tcccaggagg agatgaccaa gaaccaggtc agcctgacct gcctggtcaa aggcttctac    1200
cccagcgaca tcgccgtgga gtgggagagc aatgggcagc cggagaacaa ctacaagacc    1260
acgcctcccg tgctggactc cgacggctcc ttcttcctct acagcaggct aaccgtggac    1320
aagagcaggt ggcaggaggg gaatgtcttc tcatgctccg tgatgcatga ggctctgcac    1380
```
aaccactaca cacagaagag cctctccctg tctctgggta aatga        1425

<210> SEQ ID NO 93
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

```
Met Asp Met Arg Val Pro Ala Gln Leu Leu Gly Leu Leu Leu Leu Trp
1               5                   10                  15

Leu Arg Gly Ala Arg Cys Glu Ile Val Met Thr Gln Ser Pro Ala Thr
            20                  25                  30

Leu Ser Val Ser Pro Gly Glu Arg Ala Thr Leu Ser Cys Arg Ala Ser
        35                  40                  45

Gln Arg Gly Asn Asn Asn Leu Ala Trp Tyr Gln Gln Lys Pro Gly Gln
    50                  55                  60

Ala Pro Arg Leu Leu Ile Tyr Gly Ala Ser Thr Arg Ala Thr Gly Ile
65                  70                  75                  80

Pro Ala Arg Phe Ser Gly Ser Gly Ser Gly Thr Glu Phe Thr Leu Thr
                85                  90                  95

Ile Ser Ser Leu Gln Ser Glu Asp Phe Ala Val Tyr Tyr Cys Gln Gln
            100                 105                 110

Tyr Asn Ile Trp Pro Arg Ser Phe Gly Gln Gly Thr Lys Leu Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 94
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 94
atggacatga gggtgcccgc tcagctcctg gggctcctgc tgctgtggct gagaggtgcg        60
cgctgtgaaa tagtgatgac gcagtctcca gccaccctgt ctgtgtctcc agggaaaga       120 gccaccctct cctgcagggc cagtcagagg gtaataaca acttagcctg gtaccagcag       180
aaacctggcc aggctcccag gctcctcatc tatggtgcat ccaccagggc cactggtatc       240
ccagccaggt tcagtggcag tgggtctggg acagagttca ctctcaccat cagcagcctg       300

```
cagtctgaag attttgcagt ttattactgt cagcagtata atatctggcc tcgcagtttt   360
ggccagggga ccaagctgga gatcaaacgt acggtggctg caccatctgt cttcatcttc   420
ccgccatctg atgagcagtt gaaatctgga actgcctctg ttgtgtgcct gctgaataac   480
ttctatccca gagaggccaa agtacagtgg aaggtggata cgccctcca atcgggtaac    540 tcccaggaga gtgtcacaga gcaggacagc aaggacagca cctacagcct cagcagcacc   600
ctgacgctga gcaaagcaga ctacgagaaa cacaaagtct acgcctgcga agtcacccat   660
cagggcctga gctcgcccgt cacaaagagc ttcaacaggg gagagtgttg a            711
```

```
<210> SEQ ID NO 95
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95
```

```
Met Asp Met Arg Val Pro Ala Gln Leu Leu Gly Leu Leu Leu Leu Trp
1               5                   10                  15

Leu Arg Gly Ala Arg Cys Glu Val Gln Leu Leu Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Asn Tyr Ala Met Ser Trp Val Arg Gln Ala Pro Gly
    50                  55                  60

Lys Gly Leu Glu Trp Val Ser Ala Val Ser Ser Gly Gly Ser Thr
65                  70                  75                  80

Phe Tyr Ala Asp Ser Met Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Phe Cys Ala Lys Glu Gly Leu Glu Ile Leu Tyr Tyr
        115                 120                 125

Phe Asp Tyr Trp Gly Gln Gly Thr Leu Val Thr Val Ser Ser Ala Ser
    130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Asn Phe Gly Thr Gln Thr Tyr Thr
    210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
                245                 250                 255

Ala Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285
```

His Glu Asp Pro Glu Val Gln Phe Asn Trp Tyr Val Asp Gly Val Glu
    290                 295                 300

Val His Asn Ala Lys Thr Lys Pro Arg Glu Glu Gln Phe Asn Ser Thr
305                 310                 315                 320

Phe Arg Val Val Ser Val Leu Thr Val Val His Gln Asp Trp Leu Asn
                325                 330                 335

Gly Lys Glu Tyr Lys Cys Lys Val Ser Asn Lys Gly Leu Pro Ala Pro
            340                 345                 350

Ile Glu Lys Thr Ile Ser Lys Thr Lys Gly Gln Pro Arg Glu Pro Gln
        355                 360                 365

Val Tyr Thr Leu Pro Pro Ser Arg Glu Glu Met Thr Lys Asn Gln Val
370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Met Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
450                 455                 460

Ser Pro Gly Lys
465

<210> SEQ ID NO 96
<211> LENGTH: 1407
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96
atggacatga gggtgcccgc tcagctcctg gggctcctgc tgctgtggct gagaggtgcg     60
cgctgtgagg tgcagctgtt ggagtctggg ggaggcttgg tacagcctgg ggggtccctg    120
agactctcct gtgcagcctc tggattcacc tttagcaact atgccatgag ctgggtccgc    180
caggctccag ggaaggggct ggagtgggtc tcagctgtta gtggtagtgg tggtagcaca    240
ttctacgcag actccatgaa gggccggttc accatctcca gagacaattc caagaacacg    300
ctgtatctgc aaatgaacag cctgagagcc gaggacacgg ccgtgtattt ctgtgcgaaa    360
gaggggctgg agattctgta ctactttgac tactggggcc agggaaccct ggtcaccgtc    420
tctagtgcct ccaccaaggg cccatcggtc ttccccctgg cgccctgctc caggagcacc    480
tccgagagca cagcggccct gggctgcctg gtcaaggact acttccccga accggtgacg    540
gtgtcgtgga actcaggcgc tctgaccagc ggcgtgcaca ccttcccagc tgtcctacag    600
tcctcaggac tctactccct cagcagcgtg gtgaccgtgc cctccagcaa cttcggcacc    660
cagacctaca cctgcaacgt agatcacaag cccagcaaca ccaaggtgga caagacagtt    720
gagcgcaaat gttgtgtcga gtgcccaccg tgcccagcac cacctgtggc aggaccgtca    780
gtcttcctct tccccccaaa acccaaggac accctcatga tctcccggac ccctgaggtc    840
acgtgcgtgg tggtggacgt gagccacgaa gaccccgagg tccagttcaa ctggtacgtg    900
gacggcgtgg aggtgcataa tgccaagaca aagccacggg aggagcagtt caacagcacg    960

-continued

```
ttccgtgtgg tcagcgtcct caccgttgtg caccaggact ggctgaacgg caaggagtac    1020
aagtgcaagg tctccaacaa aggcctccca gcccccatcg agaaaaccat ctccaaaacc    1080
aaagggcagc cccgagaacc acaggtgtac accctgcccc catcccggga ggagatgacc    1140
aagaaccagg tcagcctgac ctgcctggtc aaaggcttct accccagcga catcgccgtg    1200
gagtgggaga gcaatgggca gccggagaac aactacaaga ccacacctcc catgctggac    1260
tccgacggct ccttcttcct ctacagcaag ctcaccgtgg acaagagcag gtggcagcag    1320
gggaacgtct tctcatgctc cgtgatgcat gaggctctgc acaaccacta cacgcagaag    1380
agcctctccc tgtctccggg taaatga                                        1407
```

<210> SEQ ID NO 97
<211> LENGTH: 611
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 97

```
Met Asp Met Arg Val Pro Ala Gln Leu Leu Gly Leu Leu Leu Leu Trp
1               5                   10                  15

Leu Arg Gly Ala Arg Cys Glu Val Gln Leu Leu Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Asn Tyr Ala Met Ser Trp Val Arg Gln Ala Pro Gly
    50                  55                  60

Lys Gly Leu Glu Trp Val Ser Ala Val Ser Gly Ser Gly Gly Ser Thr
65                  70                  75                  80

Phe Tyr Ala Asp Ser Met Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Phe Cys Ala Lys Glu Gly Leu Glu Ile Leu Tyr Tyr
        115                 120                 125

Phe Asp Tyr Trp Gly Gln Gly Thr Leu Val Thr Val Ser Ser Gly Ser
    130                 135                 140

Ala Ser Ala Pro Thr Leu Phe Pro Leu Val Ser Cys Glu Asn Ser Pro
145                 150                 155                 160

Ser Asp Thr Ser Ser Val Ala Val Gly Cys Leu Ala Gln Asp Phe Leu
                165                 170                 175

Pro Asp Ser Ile Thr Phe Ser Trp Lys Tyr Lys Asn Asn Ser Asp Ile
            180                 185                 190

Ser Ser Thr Arg Gly Phe Pro Ser Val Leu Arg Gly Gly Lys Tyr Ala
        195                 200                 205

Ala Thr Ser Gln Val Leu Leu Pro Ser Lys Asp Val Met Gln Gly Thr
    210                 215                 220

Asp Glu His Val Val Cys Lys Val Gln His Pro Asn Gly Asn Lys Glu
225                 230                 235                 240

Lys Asn Val Pro Leu Pro Val Ile Ala Glu Leu Pro Pro Lys Val Ser
                245                 250                 255

Val Phe Val Pro Pro Arg Asp Gly Phe Phe Gly Asn Pro Arg Lys Ser
            260                 265                 270

Lys Leu Ile Cys Gln Ala Thr Gly Phe Ser Pro Arg Gln Ile Gln Val
```

```
                    275                 280                 285
Ser Trp Leu Arg Glu Gly Lys Gln Val Gly Ser Gly Val Thr Thr Asp
    290                 295                 300

Gln Val Gln Ala Glu Ala Lys Glu Ser Gly Pro Thr Thr Tyr Lys Val
305                 310                 315                 320

Thr Ser Thr Leu Thr Ile Lys Glu Ser Asp Trp Leu Ser Gln Ser Met
                325                 330                 335

Phe Thr Cys Arg Val Asp His Arg Gly Leu Thr Phe Gln Gln Asn Ala
            340                 345                 350

Ser Ser Met Cys Val Pro Asp Gln Asp Thr Ala Ile Arg Val Phe Ala
        355                 360                 365

Ile Pro Pro Ser Phe Ala Ser Ile Phe Leu Thr Lys Ser Thr Lys Leu
    370                 375                 380

Thr Cys Leu Val Thr Asp Leu Thr Thr Tyr Asp Ser Val Thr Ile Ser
385                 390                 395                 400

Trp Thr Arg Gln Asn Gly Glu Ala Val Lys Thr His Thr Asn Ile Ser
                405                 410                 415

Glu Ser His Pro Asn Ala Thr Phe Ser Ala Val Gly Glu Ala Ser Ile
            420                 425                 430

Cys Glu Asp Asp Trp Asn Ser Gly Glu Arg Phe Thr Cys Thr Val Thr
        435                 440                 445

His Thr Asp Leu Pro Ser Pro Leu Lys Gln Thr Ile Ser Arg Pro Lys
    450                 455                 460

Gly Val Ala Leu His Arg Pro Asp Val Tyr Leu Leu Pro Pro Ala Arg
465                 470                 475                 480

Glu Gln Leu Asn Leu Arg Glu Ser Ala Thr Ile Thr Cys Leu Val Thr
                485                 490                 495

Gly Phe Ser Pro Ala Asp Val Phe Val Gln Trp Met Gln Arg Gly Gln
            500                 505                 510

Pro Leu Ser Pro Glu Lys Tyr Val Thr Ser Ala Pro Met Pro Glu Pro
        515                 520                 525

Gln Ala Pro Gly Arg Tyr Phe Ala His Ser Ile Leu Thr Val Ser Glu
    530                 535                 540

Glu Glu Trp Asn Thr Gly Glu Thr Tyr Thr Cys Val Val Ala His Glu
545                 550                 555                 560

Ala Leu Pro Asn Arg Val Thr Glu Arg Thr Val Asp Lys Ser Thr Gly
                565                 570                 575

Lys Pro Thr Leu Tyr Asn Val Ser Leu Val Met Ser Asp Thr Ala Gly
            580                 585                 590

Thr Cys Tyr Ala Ser Asp Tyr Lys Asp Asp Asp Asp Lys His His His
        595                 600                 605

His His His
    610

<210> SEQ ID NO 98
<211> LENGTH: 573
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Glu Val Gln Leu Leu Glu Ser Gly Gly Gly Leu Val Gln Pro Gly Gly
1               5                   10                  15
```

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
         35                  40                  45

Ser Ala Val Ser Gly Ser Gly Gly Ser Thr Phe Tyr Ala Asp Ser Met
     50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                 85                  90                  95

Ala Lys Glu Gly Leu Glu Ile Leu Tyr Tyr Phe Asp Tyr Trp Gly Gln
            100                 105                 110

Gly Thr Leu Val Thr Val Ser Ser Gly Ser Ala Ser Ala Pro Thr Leu
         115                 120                 125

Phe Pro Leu Val Ser Cys Glu Asn Ser Pro Ser Asp Thr Ser Ser Val
    130                 135                 140

Ala Val Gly Cys Leu Ala Gln Asp Phe Leu Pro Asp Ser Ile Thr Phe
145                 150                 155                 160

Ser Trp Lys Tyr Lys Asn Asn Ser Asp Ile Ser Ser Thr Arg Gly Phe
                165                 170                 175

Pro Ser Val Leu Arg Gly Gly Lys Tyr Ala Ala Thr Ser Gln Val Leu
            180                 185                 190

Leu Pro Ser Lys Asp Val Met Gln Gly Thr Asp Glu His Val Val Cys
        195                 200                 205

Lys Val Gln His Pro Asn Gly Asn Lys Glu Lys Asn Val Pro Leu Pro
210                 215                 220

Val Ile Ala Glu Leu Pro Pro Lys Val Ser Val Phe Val Pro Pro Arg
225                 230                 235                 240

Asp Gly Phe Phe Gly Asn Pro Arg Lys Ser Lys Leu Ile Cys Gln Ala
                245                 250                 255

Thr Gly Phe Ser Pro Arg Gln Ile Gln Val Ser Trp Leu Arg Glu Gly
            260                 265                 270

Lys Gln Val Gly Ser Gly Val Thr Thr Asp Gln Val Gln Ala Glu Ala
        275                 280                 285

Lys Glu Ser Gly Pro Thr Thr Tyr Lys Val Thr Ser Thr Leu Thr Ile
290                 295                 300

Lys Glu Ser Asp Trp Leu Ser Gln Ser Met Phe Thr Cys Arg Val Asp
305                 310                 315                 320

His Arg Gly Leu Thr Phe Gln Gln Asn Ala Ser Ser Met Cys Val Pro
                325                 330                 335

Asp Gln Asp Thr Ala Ile Arg Val Phe Ala Ile Pro Pro Ser Phe Ala
            340                 345                 350

Ser Ile Phe Leu Thr Lys Ser Thr Lys Leu Thr Cys Leu Val Thr Asp
        355                 360                 365

Leu Thr Thr Tyr Asp Ser Val Thr Ile Ser Trp Thr Arg Gln Asn Gly
370                 375                 380

Glu Ala Val Lys Thr His Thr Asn Ile Ser Glu Ser His Pro Asn Ala
385                 390                 395                 400

Thr Phe Ser Ala Val Gly Glu Ala Ser Ile Cys Glu Asp Asp Trp Asn
                405                 410                 415

Ser Gly Glu Arg Phe Thr Cys Thr Val Thr His Thr Asp Leu Pro Ser
            420                 425                 430

Pro Leu Lys Gln Thr Ile Ser Arg Pro Lys Gly Val Ala Leu His Arg

```
            435                 440                 445
Pro Asp Val Tyr Leu Leu Pro Pro Ala Arg Glu Gln Leu Asn Leu Arg
    450                 455                 460

Glu Ser Ala Thr Ile Thr Cys Leu Val Thr Gly Phe Ser Pro Ala Asp
465                 470                 475                 480

Val Phe Val Gln Trp Met Gln Arg Gly Gln Pro Leu Ser Pro Glu Lys
                485                 490                 495

Tyr Val Thr Ser Ala Pro Met Pro Glu Pro Gln Ala Pro Gly Arg Tyr
                500                 505                 510

Phe Ala His Ser Ile Leu Thr Val Ser Glu Glu Glu Trp Asn Thr Gly
                515                 520                 525

Glu Thr Tyr Thr Cys Val Val Ala His Glu Ala Leu Pro Asn Arg Val
    530                 535                 540

Thr Glu Arg Thr Val Asp Lys Ser Thr Gly Lys Pro Thr Leu Tyr Asn
545                 550                 555                 560

Val Ser Leu Val Met Ser Asp Thr Ala Gly Thr Cys Tyr
                565                 570
```

<210> SEQ ID NO 99
<211> LENGTH: 1836
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 99

```
atggacatga gggtgcccgc tcagctcctg gggctcctgc tgctgtggct gagaggtgcg    60
cgctgtgagg tgcagctgtt ggagtctggg ggaggcttgg tacagcctgg ggggtccctg   120
agactctcct gtgcagcctc tggattcacc tttagcaact atgccatgag ctgggtccgc   180
caggctccag ggaaggggct ggagtgggtc tcagctgtta gtggtagtgg tggtagcaca   240
ttctacgcag actccatgaa gggccggttc accatctcca gagacaattc caagaacacg   300
ctgtatctgc aaatgaacag cctgagagcc gaggacacgg ccgtgtattt ctgtgcgaaa   360
gaggggctgg agattctgta ctactttgac tactggggcc agggaaccct ggtcaccgtc   420
tctagtggga gtgcatccgc cccaacccct tccccctcg tatcctgtga gaattccccg   480
tcggatacga gcagcgtggc cgttggctgc tcgcacaggg acttccttcc gactccatc   540 actttctcct ggaaatacaa gaacaactct gacatcagca gcacccgggg cttcccatca   600
gtcctgagag gggcaagta cgcagccacc tcacaggtgc tgctgccttc aaggacgtc   660 atgcagggca cagacgaaca cgtggtgtgc aaagtccagc acccaacgg caacaaagaa   720 aagaacgtgc ctcttccagt gattgccgag ctgcctccaa agtgagcgt cttcgtccca   780 ccccgcgacg gcttcttcgg caacccccgc aagtccaagc tcatctgcca ggccacgggt   840
ttcagtcccc ggcagattca ggtgtcctgg ctgcgcgagg ggaagcaggt ggggtctggc   900
gtcaccacgg accaggtgca ggctgaggcc aaagagtctg gcccacgac ctacaaggtg   960 accagcacac tgaccatcaa agagagcgac tggctcagcc agagcatgtt cacctgccgc  1020
gtggatcaca gggcctgac cttccagcag atgcgtcct ccatgtgtgt ccccgatcaa  1080
gacacagcca tccgggtctt cgccatcccc ccatcctttg ccagcatctt cctcaccaag  1140
tccaccaagt tgacctgcct ggtcacagac ctgaccacct atgacagcgt gaccatctcc  1200
tggacccgcc agaatggcga agctgtgaaa acccacacca catctccga gagccacccc  1260
```

-continued

```
aatgccactt tcagcgccgt gggtgaggcc agcatctgcg aggatgactg gaattccggg      1320
gagaggttca cgtgcaccgt gacccacaca gacctgccct cgccactgaa gcagaccatc      1380
tcccggccca agggggtggc cctgcacagg cccgatgtct acttgctgcc accagcccgg      1440
gagcagctga acctgcggga gtcggccacc atcacgtgcc tggtgacggg cttctctccc      1500
gcggacgtct tcgtgcagtg gatgcagagg gggcagccct tgtccccgga gaagtatgtg      1560
accagcgccc caatgcctga gccccaggcc ccaggccggt acttcgccca cagcatcctg      1620
accgtgtccg aagaggaatg gaacacgggg gagacctaca cctgcgtggt ggcccatgag      1680
gccctgccca cagggtcac cgagaggacc gtggacaagt ccaccggtaa acccacctg       1740 tacaacgtgt ccctggtcat gtccgacaca gctggcacct gctacgctag cgattataaa      1800
gatgatgatg ataaacatca ccatcaccat cactga                                1836
```

<210> SEQ ID NO 100
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

```
Met Asp Met Arg Val Pro Ala Gln Leu Leu Gly Leu Leu Leu Leu Trp
1               5                   10                  15

Leu Arg Gly Ala Arg Cys Gln Pro Val Leu Thr Gln Pro Pro Ser Ala
            20                  25                  30

Ser Ala Ser Leu Gly Ala Ser Val Thr Leu Thr Cys Thr Leu Ser Ser
        35                  40                  45

Gly Tyr Ser Asn Tyr Lys Val Asp Trp Tyr Gln Gln Arg Pro Gly Lys
    50                  55                  60

Gly Pro Arg Phe Val Met Arg Val Gly Thr Gly Gly Ile Val Gly Ser
65                  70                  75                  80

Lys Gly Asp Gly Ile Pro Asp Arg Phe Ser Val Leu Gly Ser Gly Leu
                85                  90                  95

Asn Arg Tyr Leu Thr Ile Lys Asn Ile Gln Glu Glu Asp Glu Ser Asp
            100                 105                 110

Tyr His Cys Gly Ala Asp His Gly Ser Gly Ser Asn Phe Val Trp Val
        115                 120                 125

Phe Gly Gly Gly Thr Lys Leu Thr Val Leu Gly Gln Pro Lys Ala Asn
    130                 135                 140

Pro Thr Val Thr Leu Phe Pro Pro Ser Ser Glu Glu Leu Gln Ala Asn
145                 150                 155                 160

Lys Ala Thr Leu Val Cys Leu Ile Ser Asp Phe Tyr Pro Gly Ala Val
                165                 170                 175

Thr Val Ala Trp Lys Ala Asp Gly Ser Pro Val Lys Ala Gly Val Glu
            180                 185                 190

Thr Thr Lys Pro Ser Lys Gln Ser Asn Asn Lys Tyr Ala Ala Ser Ser
        195                 200                 205

Tyr Leu Ser Leu Thr Pro Glu Gln Trp Lys Ser His Arg Ser Tyr Ser
    210                 215                 220

Cys Gln Val Thr His Glu Gly Ser Thr Val Glu Lys Thr Val Ala Pro
225                 230                 235                 240

Thr Glu Cys Ser
```

<210> SEQ ID NO 101
<211> LENGTH: 735
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 101

```
atggacatga gggtgcccgc tcagctcctg gggctcctgc tgctgtggct gagaggtgcg      60
cgctgtcagc ctgtgctgac tcagccacct tctgcatcag cctccctggg agcctcggtc     120
acactcacct gcaccctgag cagcggctac agtaattata aagtggactg gtaccagcag     180
agaccaggga agggcccccg gtttgtgatg cgagtgggca ctggtgggat tgtgggatcc     240
aaggggatg gcatccctga tcgcttctca gtcttgggct caggcctgaa tcggtacctg      300
accatcaaga catccagga gaggatgag agtgactacc actgtggggc agaccatggc      360
agtgggagca acttcgtgtg ggtgttcggc ggagggacca agctgaccgt cctaggtcag    420
cccaaggcca accccactgt cactctgttc ccgccctcct ctgaggagct ccaagccaac    480
aaggccacac tagtgtgtct gatcagtgac ttctacccgg gagctgtgac agtggcctgg    540
aaggcagatg cagccccgt caaggcggga gtggagacca ccaaaccctc aaacagagc     600
aacaacaagt acgcggccag cagctacctg agcctgacgc ccgagcagtg gaagtcccac    660
agaagctaca gctgccaggt cacgcatgaa gggagcaccg tggagaagac agtggcccct    720
acagaatgtt catga                                                      735
```

<210> SEQ ID NO 102
<211> LENGTH: 469
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 102

```
Met Asp Met Arg Val Pro Ala Gln Leu Leu Gly Leu Leu Leu Leu Trp
1               5                   10                  15

Leu Arg Gly Ala Arg Cys Gln Val Gln Leu Gln Gln Trp Gly Ala Gly
            20                  25                  30

Leu Leu Lys Pro Ser Glu Thr Leu Ser Leu Thr Cys Ala Val Tyr Gly
        35                  40                  45

Gly Ser Phe Ser Gly Tyr Tyr Trp Ser Trp Ile Arg Gln Pro Pro Gly
    50                  55                  60

Lys Gly Leu Glu Trp Ile Gly Glu Ile Asn His Ser Gly Ser Thr Asn
65                  70                  75                  80

Tyr Asn Pro Ser Leu Lys Ser Arg Val Thr Ile Ser Val Asp Thr Ser
                85                  90                  95

Lys Asn Gln Phe Ser Leu Lys Leu Ser Ser Val Thr Ala Ala Asp Thr
            100                 105                 110

Ala Val Tyr Tyr Cys Ala Arg Ala Lys Phe Tyr Gly Trp Gly Asn Tyr
        115                 120                 125

Pro Phe Asp Ser Trp Gly Gln Gly Thr Leu Val Thr Val Ser Ser Ala
    130                 135                 140

Ser Thr Lys Gly Pro Ser Val Phe Pro Leu Ala Pro Cys Ser Arg Ser
145                 150                 155                 160

Thr Ser Glu Ser Thr Ala Ala Leu Gly Cys Leu Val Lys Asp Tyr Phe
                165                 170                 175
```

```
Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Asn Phe Gly Thr Gln Thr Tyr
    210                 215                 220

Thr Cys Asn Val Asp His Lys Pro Ser Asn Thr Lys Val Asp Lys Thr
225                 230                 235                 240

Val Glu Arg Lys Cys Cys Val Glu Cys Pro Cys Pro Ala Pro Pro
                245                 250                 255

Val Ala Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Gln Phe Asn Trp Tyr Val Asp Gly Val
    290                 295                 300

Glu Val His Asn Ala Lys Thr Lys Pro Arg Glu Glu Gln Phe Asn Ser
305                 310                 315                 320

Thr Phe Arg Val Val Ser Val Leu Thr Val Val His Gln Asp Trp Leu
                325                 330                 335

Asn Gly Lys Glu Tyr Lys Cys Lys Val Ser Asn Lys Gly Leu Pro Ala
            340                 345                 350

Pro Ile Glu Lys Thr Ile Ser Lys Thr Lys Gly Gln Pro Arg Glu Pro
        355                 360                 365

Gln Val Tyr Thr Leu Pro Pro Ser Arg Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Met Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465

<210> SEQ ID NO 103
<211> LENGTH: 1410
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103
atggacatga gggtgcccgc tcagctcctg gggctcctgc tgctgtggct gagaggtgcg      60
cgctgtcagg tgcagctaca gcagtggggc gcaggactgt tgaagccttc ggagaccctg     120
tccctcacct gcgctgtcta tggtgggtcc ttcagtggtt actactggag ctggatccgc     180
cagcccccag ggaaggggct ggagtggatt gggaaatca atcatagtgg aagcaccaac     240
tacaacccgt ccctcaagag tcgagtcacc atatcagtag acacgtccaa gaaccagttc     300
```

```
tccctgaagc tgagctctgt gaccgccgcg gacacggctg tgtattactg tgcgagagca      360
aagttctatg gttgggggaa ttatccgttt gactcctggg gccagggaac cctggtcacc      420
gtctctagtg cctccaccaa gggcccatcg gtcttccccc tggcgccctg ctccaggagc      480
acctccgaga gcacagcggc cctgggctgc ctggtcaagg actacttccc cgaaccggtg      540
acggtgtcgt ggaactcagg cgctctgacc agcggcgtgc acaccttccc agctgtccta      600
cagtcctcag gactctactc cctcagcagc gtggtgaccg tgccctccag caacttcggc      660
acccagacct acacctgcaa cgtagatcac aagcccagca caccaaggt ggacaagaca       720 gttgagcgca aatgttgtgt cgagtgccca ccgtgcccag caccacctgt ggcaggaccg      780
tcagtcttcc tcttcccccc aaaacccaag gacaccctca tgatctcccg gacccctgag      840
gtcacgtgcg tggtggtgga cgtgagccac gaagacccg aggtccagtt caactggtac       900
gtggacggcg tggaggtgca taatgccaag acaaagccac gggaggagca gttcaacagc      960
acgttccgtg tggtcagcgt cctcaccgtt gtgcaccagg actggctgaa cggcaaggag     1020
tacaagtgca aggtctccaa caaaggcctc ccagccccca tcgagaaaac catctccaaa     1080
accaaagggc agccccgaga accacaggtg tacaccctgc ccccatcccg ggaggagatg     1140
accaagaacc aggtcagcct gacctgcctg gtcaaaggct tctacccag cgacatcgcc      1200 gtggagtggg agagcaatgg gcagccggag aacaactaca agaccacacc tcccatgctg     1260
gactccgacg gctccttctt cctctacagc aagctcaccg tggacaagag caggtggcag     1320
caggggaacg tcttctcatg ctccgtgatg catgaggctc tgcacaacca ctacacgcag     1380
aagagcctct ccctgtctcc gggtaaatga                                      1410
```

<210> SEQ ID NO 104
<211> LENGTH: 612
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

```
Met Asp Met Arg Val Pro Ala Gln Leu Leu Gly Leu Leu Leu Leu Trp
1               5                   10                  15

Leu Arg Gly Ala Arg Cys Gln Val Gln Leu Gln Gln Trp Gly Ala Gly
            20                  25                  30

Leu Leu Lys Pro Ser Glu Thr Leu Ser Leu Thr Cys Ala Val Tyr Gly
        35                  40                  45

Gly Ser Phe Ser Gly Tyr Tyr Trp Ser Trp Ile Arg Gln Pro Pro Gly
    50                  55                  60

Lys Gly Leu Glu Trp Ile Gly Glu Ile Asn His Ser Gly Ser Thr Asn
65                  70                  75                  80

Tyr Asn Pro Ser Leu Lys Ser Arg Val Thr Ile Ser Val Asp Thr Ser
                85                  90                  95

Lys Asn Gln Phe Ser Leu Lys Leu Ser Ser Val Thr Ala Ala Asp Thr
            100                 105                 110

Ala Val Tyr Tyr Cys Ala Arg Ala Lys Phe Tyr Gly Trp Gly Asn Tyr
        115                 120                 125

Pro Phe Asp Ser Trp Gly Gln Gly Thr Leu Val Thr Val Ser Ser Gly
    130                 135                 140

Ser Ala Ser Ala Pro Thr Leu Phe Pro Leu Val Ser Cys Glu Asn Ser
145                 150                 155                 160
```

```
Pro Ser Asp Thr Ser Ser Val Ala Val Gly Cys Leu Ala Gln Asp Phe
            165                 170                 175

Leu Pro Asp Ser Ile Thr Phe Ser Trp Lys Tyr Lys Asn Asn Ser Asp
        180                 185                 190

Ile Ser Ser Thr Arg Gly Phe Pro Ser Val Leu Arg Gly Gly Lys Tyr
        195                 200                 205

Ala Ala Thr Ser Gln Val Leu Leu Pro Ser Lys Asp Val Met Gln Gly
        210                 215                 220

Thr Asp Glu His Val Val Cys Lys Val Gln His Pro Asn Gly Asn Lys
225                 230                 235                 240

Glu Lys Asn Val Pro Leu Pro Val Ile Ala Glu Leu Pro Pro Lys Val
            245                 250                 255

Ser Val Phe Val Pro Pro Arg Asp Gly Phe Phe Gly Asn Pro Arg Lys
            260                 265                 270

Ser Lys Leu Ile Cys Gln Ala Thr Gly Phe Ser Pro Arg Gln Ile Gln
            275                 280                 285

Val Ser Trp Leu Arg Glu Gly Lys Gln Val Gly Ser Gly Val Thr Thr
            290                 295                 300

Asp Gln Val Gln Ala Glu Ala Lys Glu Ser Gly Pro Thr Thr Tyr Lys
305                 310                 315                 320

Val Thr Ser Thr Leu Thr Ile Lys Glu Ser Asp Trp Leu Ser Gln Ser
            325                 330                 335

Met Phe Thr Cys Arg Val Asp His Arg Gly Leu Thr Phe Gln Gln Asn
            340                 345                 350

Ala Ser Ser Met Cys Val Pro Asp Gln Asp Thr Ala Ile Arg Val Phe
            355                 360                 365

Ala Ile Pro Pro Ser Phe Ala Ser Ile Phe Leu Thr Lys Ser Thr Lys
            370                 375                 380

Leu Thr Cys Leu Val Thr Asp Leu Thr Thr Tyr Asp Ser Val Thr Ile
385                 390                 395                 400

Ser Trp Thr Arg Gln Asn Gly Glu Ala Val Lys Thr His Thr Asn Ile
            405                 410                 415

Ser Glu Ser His Pro Asn Ala Thr Phe Ser Ala Val Gly Glu Ala Ser
            420                 425                 430

Ile Cys Glu Asp Asp Trp Asn Ser Gly Glu Arg Phe Thr Cys Thr Val
            435                 440                 445

Thr His Thr Asp Leu Pro Ser Pro Leu Lys Gln Thr Ile Ser Arg Pro
            450                 455                 460

Lys Gly Val Ala Leu His Arg Pro Asp Val Tyr Leu Leu Pro Pro Ala
465                 470                 475                 480

Arg Glu Gln Leu Asn Leu Arg Glu Ser Ala Thr Ile Thr Cys Leu Val
            485                 490                 495

Thr Gly Phe Ser Pro Ala Asp Val Phe Val Gln Trp Met Gln Arg Gly
            500                 505                 510

Gln Pro Leu Ser Pro Glu Lys Tyr Val Thr Ser Ala Pro Met Pro Glu
            515                 520                 525

Pro Gln Ala Pro Gly Arg Tyr Phe Ala His Ser Ile Leu Thr Val Ser
            530                 535                 540

Glu Glu Glu Trp Asn Thr Gly Glu Thr Tyr Thr Cys Val Val Ala His
545                 550                 555                 560

Glu Ala Leu Pro Asn Arg Val Thr Glu Arg Thr Val Asp Lys Ser Thr
            565                 570                 575

Gly Lys Pro Thr Leu Tyr Asn Val Ser Leu Val Met Ser Asp Thr Ala
```

```
                         580                 585                 590
Gly Thr Cys Tyr Ala Ser Asp Tyr Lys Asp Asp Asp Lys His His
                595                 600                 605

His His His His
        610

<210> SEQ ID NO 105
<211> LENGTH: 574
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Lys Phe Tyr Gly Trp Gly Asn Tyr Pro Phe Asp Ser Trp Gly
            100                 105                 110

Gln Gly Thr Leu Val Thr Val Ser Ser Gly Ser Ala Ser Ala Pro Thr
        115                 120                 125

Leu Phe Pro Leu Val Ser Cys Glu Asn Ser Pro Ser Asp Thr Ser Ser
    130                 135                 140

Val Ala Val Gly Cys Leu Ala Gln Asp Phe Leu Pro Asp Ser Ile Thr
145                 150                 155                 160

Phe Ser Trp Lys Tyr Lys Asn Asn Ser Asp Ile Ser Ser Thr Arg Gly
                165                 170                 175

Phe Pro Ser Val Leu Arg Gly Gly Lys Tyr Ala Ala Thr Ser Gln Val
            180                 185                 190

Leu Leu Pro Ser Lys Asp Val Met Gln Gly Thr Asp Glu His Val Val
        195                 200                 205

Cys Lys Val Gln His Pro Asn Gly Asn Lys Glu Lys Asn Val Pro Leu
    210                 215                 220

Pro Val Ile Ala Glu Leu Pro Pro Lys Val Ser Val Phe Val Pro Pro
225                 230                 235                 240

Arg Asp Gly Phe Phe Gly Asn Pro Arg Lys Ser Lys Leu Ile Cys Gln
                245                 250                 255

Ala Thr Gly Phe Ser Pro Arg Gln Ile Gln Val Ser Trp Leu Arg Glu
            260                 265                 270

Gly Lys Gln Val Gly Ser Gly Val Thr Thr Asp Gln Val Gln Ala Glu
        275                 280                 285

Ala Lys Glu Ser Gly Pro Thr Thr Tyr Lys Val Thr Ser Thr Leu Thr
    290                 295                 300

Ile Lys Glu Ser Asp Trp Leu Ser Gln Ser Met Phe Thr Cys Arg Val
305                 310                 315                 320
```

| | | | | | | | | | | | |
|---|---|---|---|---|---|---|---|---|---|---|---|
|Asp|His|Arg|Gly|Leu|Thr|Phe|Gln|Gln|Asn|Ala|Ser|Ser|Met|Cys|Val|
| | | |325| | | |330| | | |335|
|Pro|Asp|Gln|Asp|Thr|Ala|Ile|Arg|Val|Phe|Ala|Ile|Pro|Pro|Ser|Phe|
| |340| | | | |345| | | | |350| | | | |

Asp His Arg Gly Leu Thr Phe Gln Gln Asn Ala Ser Ser Met Cys Val
                325                 330                 335

Pro Asp Gln Asp Thr Ala Ile Arg Val Phe Ala Ile Pro Pro Ser Phe
        340                 345                 350

Ala Ser Ile Phe Leu Thr Lys Ser Thr Lys Leu Thr Cys Leu Val Thr
                355                 360                 365

Asp Leu Thr Thr Tyr Asp Ser Val Thr Ile Ser Trp Thr Arg Gln Asn
        370                 375                 380

Gly Glu Ala Val Lys Thr His Thr Asn Ile Ser Glu Ser His Pro Asn
385                 390                 395                 400

Ala Thr Phe Ser Ala Val Gly Glu Ala Ser Ile Cys Glu Asp Asp Trp
                405                 410                 415

Asn Ser Gly Glu Arg Phe Thr Cys Thr Val Thr His Thr Asp Leu Pro
        420                 425                 430

Ser Pro Leu Lys Gln Thr Ile Ser Arg Pro Lys Gly Val Ala Leu His
                435                 440                 445

Arg Pro Asp Val Tyr Leu Leu Pro Pro Ala Arg Glu Gln Leu Asn Leu
        450                 455                 460

Arg Glu Ser Ala Thr Ile Thr Cys Leu Val Thr Gly Phe Ser Pro Ala
465                 470                 475                 480

Asp Val Phe Val Gln Trp Met Gln Arg Gly Gln Pro Leu Ser Pro Glu
                485                 490                 495

Lys Tyr Val Thr Ser Ala Pro Met Pro Glu Pro Gln Ala Pro Gly Arg
                500                 505                 510

Tyr Phe Ala His Ser Ile Leu Thr Val Ser Glu Glu Trp Asn Thr
        515                 520                 525

Gly Glu Thr Tyr Thr Cys Val Val Ala His Glu Ala Leu Pro Asn Arg
530                 535                 540

Val Thr Glu Arg Thr Val Asp Lys Ser Thr Gly Lys Pro Thr Leu Tyr
545                 550                 555                 560

Asn Val Ser Leu Val Met Ser Asp Thr Ala Gly Thr Cys Tyr
                565                 570

<210> SEQ ID NO 106
<211> LENGTH: 1839
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 106

```
atggacatga gggtgcccgc tcagctcctg gggctcctgc tgctgtggct gagaggtgcg      60
cgctgtcagg tgcagctaca gcagtggggc gcaggactgt tgaagccttc ggagaccctg     120
tccctcacct gcgctgtcta tggtgggtcc ttcagtggtt actactggag ctggatccgc     180
cagcccccag gaagggggct ggagtggatt gggaaatca atcatagtgg aagcaccaac     240
tacaacccgt ccctcaagag tcgagtcacc atatcagtag acacgtccaa gaaccagttc     300
tccctgaagc tgagctctgt gaccgccgcg gacacggctg tgtattactg tgcgagagca     360
aagttctatg ttgggggaa ttatccgttt gactcctggg gccagggaac cctggtcacc     420
gtctctagtg ggagtgcatc cgccccaacc ctttttcccc tcgtatcctg tgagaattcc     480
ccgtcggata cgagcagcgt ggccgttggc tgcctcgcac aggacttcct tcccgactcc     540
atcactttct cctggaaata caagaacaac tctgacatca gcagcacccg gggcttccca     600
```

```
tcagtcctga gaggggggcaa gtacgcagcc acctcacagg tgctgctgcc ttccaaggac    660
gtcatgcagg gcacagacga acacgtggtg tgcaaagtcc agcaccccaa cggcaacaaa    720
gaaaagaacg tgcctcttcc agtgattgcc gagctgcctc ccaaagtgag cgtcttcgtc    780
ccaccccgcg acggcttctt cggcaacccc cgcaagtcca agctcatctg ccaggccacg    840
ggtttcagtc cccggcagat tcaggtgtcc tggctgcgcg aggggaagca ggtggggtct    900
ggcgtcacca cggaccaggt gcaggctgag gccaaagagt ctgggcccac gacctacaag    960
gtgaccagca cactgaccat caaagagagc gactggctca gccagagcat gttcacctgc   1020
cgcgtggatc acaggggcct gaccttccag cagaatgcgt cctccatgtg tgtccccgat   1080
caagacacag ccatccgggt cttcgccatc cccccatcct ttgccagcat cttcctcacc   1140
aagtccacca agttgacctg cctggtcaca gacctgacca cctatgacag cgtgaccatc   1200
tcctggaccc gccagaatgg cgaagctgtg aaaacccaca ccaacatctc cgagagccac   1260
cccaatgcca ctttcagcgc cgtgggtgag gccagcatct gcgaggatga ctggaattcc   1320
ggggagaggt tcacgtgcac cgtgacccac acagacctgc cctcgccact gaagcagacc   1380
atctcccggc caagggggt ggccctgcac aggcccgatg tctacttgct gccaccagcc   1440
cgggagcagc tgaacctgcg ggagtcggcc accatcacgt gcctggtgac gggcttctct   1500
cccgcggacg tcttcgtgca gtggatgcag aggggcagc ccttgtcccc ggagaagtat   1560
gtgaccagcg cccaatgcc tgagcccag gccccaggcc ggtacttcgc ccacagcatc   1620
ctgaccgtgt ccgaagagga atggaacacg ggggagacct acacctgcgt ggtggcccat   1680
gaggccctgc caacagggt caccgagagg accgtggaca agtccaccgg taaacccacc   1740
ctgtacaacg tgtccctggt catgtccgac acagctggca cctgctacgc tagcgattat   1800
aaagatgatg atgataaaca tcaccatcac catcactga                          1839
```

<210> SEQ ID NO 107
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Gln Ala Ser
        35                  40                  45

Gln Asp Ile Ser Asn Phe Leu Asn Trp Tyr Gln Gln Lys Pro Gly Lys
    50                  55                  60

Ala Pro Lys Leu Leu Ile Tyr Asp Ala Ser Asn Leu Glu Thr Gly Val
65                  70                  75                  80

Pro Ser Arg Phe Ser Gly Ser Gly Ser Gly Thr Asp Phe Thr Phe Thr
                85                  90                  95

Ile Ser Ser Leu Gln Pro Glu Asp Val Ala Thr Tyr Tyr Cys Gln Gln
            100                 105                 110

Tyr Asp Asn Phe Pro Leu Thr Phe Gly Gly Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 108
<211> LENGTH: 710
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 108
atggacatga gggtgcccgc tcagctcctg gggctcctgc tgctgtggct gagaggtgcg     60
cgctgtgaca tccagatgac ccagtctcca tcctccctgt ctgcatctgt aggagacaga    120
gtcaccatca cttgccaggc gagtcaggac attagcaact tttgaattg gtatcagcag    180 aaaccaggga aagcccctaa gctcctgatc tacgatgcat ccaatttgga aacaggggtc    240
ccatcaaggt tcagtggaag tggatctggg acagatttta ctttcaccat cagcagcctg    300
cagcctgaag atgttgcaac atattactgt caacagtatg ataatttccc gctcactttc    360
ggcggaggga ccaaggtgga gatcaaacgt acggtggctg caccatctgt cttcatcttc    420
ccgccatctg atgagcagtt gaaatctgga actgcctctg ttgtgtgcct gctgaataac    480
ttctatccca gagaggccaa agtacagtgg aaggtggata acgccctcca atcgggtaac    540
tcccaggaga gtgtcacaga gcaggacagc aaggacagca cctacagcct cagcagcacc    600
ctgacgctga gcaaagcaga ctacgagaaa cacaaagtct acgcctgcga agtcacccat    660
cagggcctga gctcgcccgt cacaaagagc ttcaacaggg gagagtgttg              710

<210> SEQ ID NO 109
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Met Asp Met Arg Val Pro Ala Gln Leu Leu Gly Leu Leu Leu Leu Trp
1               5                   10                  15

Leu Arg Gly Ala Arg Cys Gln Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Thr Thr Tyr Gly Ile Asn Trp Val Arg Gln Ala Pro Gly
    50                  55                  60

Gln Gly Leu Glu Trp Met Gly Trp Leu Ser Ala Tyr Ser Gly Asn Thr
65                  70                  75                  80

Asn Tyr Ala Gln Lys Leu Gln Gly Arg Val Thr Met Thr Thr Asp Thr
                85                  90                  95

Ser Thr Ser Thr Ala Tyr Met Glu Leu Arg Ser Leu Arg Ser Asp Asp
            100                 105                 110

Thr Ala Val Tyr Tyr Cys Ala Arg Gly Val Gly Ala Ser Phe Tyr Phe
        115                 120                 125

Asp Tyr Trp Gly Gln Gly Thr Leu Val Thr Val Ser Ser Ala Ser Thr
130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Lys Thr Tyr Thr Cys
    210                 215                 220

Asn Val Asp His Lys Pro Ser Asn Thr Lys Val Asp Lys Arg Val Glu
225                 230                 235                 240

Ser Lys Tyr Gly Pro Pro Cys Pro Ser Cys Pro Ala Pro Glu Phe Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

Gln Glu Asp Pro Glu Val Gln Phe Asn Trp Tyr Val Asp Gly Val Glu
290                 295                 300

Val His Asn Ala Lys Thr Lys Pro Arg Glu Glu Gln Phe Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Gly Leu Pro Ser Ser
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Gln Glu Glu Met Thr Lys Asn Gln Val
370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Arg Leu Thr
            420                 425                 430

Val Asp Lys Ser Arg Trp Gln Glu Gly Asn Val Phe Ser Cys Ser Val
        435                 440                 445

Met His Glu Ala Leu His Asn His Tyr Thr Gln Lys Ser Leu Ser Leu
450                 455                 460

Ser Leu Gly Lys
465

<210> SEQ ID NO 110
<211> LENGTH: 1407

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 110
atggacatga gggtgcccgc tcagctcctg gggctcctgc tgctgtggct gagaggtgcg      60
cgctgtcagg ttcagctggt gcagtctgga gctgaggtga agaagcctgg ggcctcagtg     120
aaggtctcct gcaaggcttc tggttacacc tttaccacct atggtatcaa ctgggtgcga     180
caggcccctg gacaagggct tgagtggatg ggatggctca cgcttacag tggtaacaca      240
aactatgcac agaaactcca gggcagagtc accatgacca cagacacatc cacgagcaca     300
gcctacatgg agctgaggag cctgagatct gacgacacgg ccgtgtatta ctgtgcgaga     360
ggagtgggag cttccttta ctttgactac tggggccagg gaaccctggt caccgtctct      420
agtgcttcca ccaagggccc atccgtcttc cccctggcgc cctgctccag gagcacctcc     480
gagagcacag ccgccctggg ctgcctggtc aaggactact ccccgaacc ggtgacggtg      540
tcgtggaact caggcgccct gaccagcggc gtgcacacct tcccggctgt cctacagtcc     600
tcaggactct actccctcag cagcgtggtg accgtgccct ccagcagctt gggcacgaag     660
acctacacct gcaacgtaga tcacaagccc agcaacacca aggtggacaa gagagttgag     720
tccaaatatg gtcccccatg cccatcatgc ccagcacctg agttcctggg gggaccatca     780
gtcttcctgt tccccccaaa acccaaggac actctcatga tctcccggac ccctgaggtc     840
acgtgcgtgt ggtggacgt gagccaggaa gaccccgagg tccagttcaa ctggtacgtg      900
gatggcgtgg aggtgcataa tgccaagaca aagccgcggg aggagcagtt caacagcacg     960
taccgtgtgg tcagcgtcct caccgtcctg caccaggact ggctgaacgg caaggagtac    1020
aagtgcaagg tctccaacaa aggcctcccg tcctccatcg agaaaaccat ctccaaagcc    1080
aaagggcagc cccgagagcc acaggtgtac accctgcccc catcccagga ggagatgacc    1140
aagaaccagg tcagcctgac ctgcctggtc aaaggcttct accccagcga catcgccgtg    1200
gagtgggaga gcaatgggca gccggagaac aactacaaga ccacgcctcc cgtgctggac    1260
tccgacggct ccttcttcct ctacagcagg ctaaccgtgg acaagagcag gtggcaggag    1320
gggaatgtct tctcatgctc cgtgatgcat gaggctctgc acaaccacta cacacagaag    1380
agcctctccc tgtctctggg taaatga                                        1407

<210> SEQ ID NO 111
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Gln Ala Ser
        35                  40                  45

Gln Asp Ile Ser Asn Tyr Leu Asn Trp Phe Gln Gln Lys Pro Gly Lys
    50                  55                  60
```

| | | | | | | | | | | | | | | |
|---|---|---|---|---|---|---|---|---|---|---|---|---|---|---|
|Ala|Pro|Asn|Leu|Leu|Ile|Tyr|Asp|Ala|Ser|Asn|Leu|Glu|Thr|Gly|Val|
|65| | | |70| | | |75| | | |80| | |

Pro Ser Arg Phe Ser Gly Gly Gly Ser Gly Thr Asp Phe Thr Phe Thr
           85              90                 95

Ile Ser Ser Leu Gln Pro Glu Asp Ile Ala Thr Tyr Tyr Cys Gln Gln
              100                105                110

Tyr Asp Asp Leu Pro Leu Thr Phe Gly Gly Gly Thr Lys Val Glu Ile
        115                120                125

Lys Arg Thr Val Ala Ala Pro Ser Val Phe Ile Phe Pro Pro Ser Asp
    130                135                140

Glu Gln Leu Lys Ser Gly Thr Ala Ser Val Val Cys Leu Leu Asn Asn
145                150                155                160

Phe Tyr Pro Arg Glu Ala Lys Val Gln Trp Lys Val Asp Asn Ala Leu
            165                170                175

Gln Ser Gly Asn Ser Gln Glu Ser Val Thr Glu Gln Asp Ser Lys Asp
        180                185                190

Ser Thr Tyr Ser Leu Ser Ser Thr Leu Thr Leu Ser Lys Ala Asp Tyr
    195                200                205

Glu Lys His Lys Val Tyr Ala Cys Glu Val Thr His Gln Gly Leu Ser
210                215                220

Ser Pro Val Thr Lys Ser Phe Asn Arg Gly Glu Cys
225                230                235

```
<210> SEQ ID NO 112
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 112
atggacatga gggtgcccgc tcagctcctg gggctcctgc tgctgtggct gagaggtgcg      60
cgctgtgaca tccagatgac ccagtctcca tcctccctgt ctgcatctgt aggagacaga     120
gtcaccatca cttgccaggc gagtcaggac attagcaact atttaaattg gtttcagcag     180
aaaccaggca aagcccctaa tctcctgatc tacgatgcat ccaatttgga aacaggggtc     240
ccatcaaggt tcagtggagg tggatctggg acagatttta cttttaccat cagcagcctg     300
cagcctgaag atattgcaac atattactgt caacagtatg atgatctccc gctcactttc     360
ggcggaggga ccaaggtgga gatcaaacgt acggtggctg caccatctgt cttcatcttc     420
ccgccatctg atgagcagtt gaaatctgga actgcctctg ttgtgtgcct gctgaataac     480
ttctatccca gagaggccaa agtacagtgg aaggtggata acgccctcca atcgggtaac     540
tcccaggaga gtgtcacaga gcaggacagc aaggacagca cctacagcct cagcagcacc     600
ctgacgctga gcaaagcaga ctacgagaaa cacaaagtct acgcctgcga agtcacccat     660
cagggcctga gctcgcccgt cacaaagagc ttcaacaggg gagagtgttg a              711

<210> SEQ ID NO 113
<211> LENGTH: 479
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113
```

```
Met Asp Met Arg Val Pro Ala Gln Leu Leu Gly Leu Leu Leu Leu Trp
1               5                   10                  15
Leu Arg Gly Ala Arg Cys Glu Val Gln Leu Val Glu Ser Gly Gly Gly
            20                  25                  30
Leu Val Gln Pro Gly Gly Ser Leu Arg Leu Ser Cys Ala Ala Ser Gly
        35                  40                  45
Phe Thr Phe Ser Ser Tyr Gly Met Asn Trp Val Arg Gln Ala Pro Gly
    50                  55                  60
Lys Gly Leu Glu Trp Val Ser Tyr Ile Ser Ser Ser Ser Thr Ile
65                  70                  75                  80
Tyr Tyr Ala Asp Ser Val Lys Gly Arg Phe Thr Ile Ser Arg Asp Asn
            85                  90                  95
Ala Lys Asn Ser Leu Tyr Leu Gln Met Asn Ser Leu Arg Asp Glu Asp
        100                 105                 110
Thr Ala Val Tyr Tyr Cys Ala Arg Asp Arg Ile Thr Ser Trp Tyr Glu
    115                 120                 125
Glu Asp Tyr Tyr Tyr Gly Met Asp Val Trp Gly Gln Gly Thr Thr
    130                 135                 140
Val Thr Val Ser Ser Ala Ser Thr Lys Gly Pro Ser Val Phe Pro Leu
145                 150                 155                 160
Ala Pro Ser Ser Lys Ser Thr Ser Gly Gly Thr Ala Ala Leu Gly Cys
            165                 170                 175
Leu Val Lys Asp Tyr Phe Pro Glu Pro Val Thr Val Ser Trp Asn Ser
        180                 185                 190
Gly Ala Leu Thr Ser Gly Val His Thr Phe Pro Ala Val Leu Gln Ser
    195                 200                 205
Ser Gly Leu Tyr Ser Leu Ser Ser Val Val Thr Val Pro Ser Ser Ser
    210                 215                 220
Leu Gly Thr Gln Thr Tyr Ile Cys Asn Val Asn His Lys Pro Ser Asn
225                 230                 235                 240
Thr Lys Val Asp Lys Lys Val Glu Pro Lys Ser Cys Asp Lys Thr His
            245                 250                 255
Thr Cys Pro Pro Cys Pro Ala Pro Glu Leu Leu Gly Gly Pro Ser Val
        260                 265                 270
Phe Leu Phe Pro Pro Lys Pro Lys Asp Thr Leu Met Ile Ser Arg Thr
    275                 280                 285
Pro Glu Val Thr Cys Val Val Val Asp Val Ser His Glu Asp Pro Glu
    290                 295                 300
Val Lys Phe Asn Trp Tyr Val Asp Gly Val Glu Val His Asn Ala Lys
305                 310                 315                 320
Thr Lys Pro Arg Glu Glu Gln Tyr Asn Ser Thr Tyr Arg Val Val Ser
            325                 330                 335
Val Leu Thr Val Leu His Gln Asp Trp Leu Asn Gly Lys Glu Tyr Lys
        340                 345                 350
Cys Lys Val Ser Asn Lys Ala Leu Pro Ala Pro Ile Glu Lys Thr Ile
    355                 360                 365
Ser Lys Ala Lys Gly Gln Pro Arg Glu Pro Gln Val Tyr Thr Leu Pro
    370                 375                 380
Pro Ser Arg Glu Glu Met Thr Lys Asn Gln Val Ser Leu Thr Cys Leu
385                 390                 395                 400
Val Lys Gly Phe Tyr Pro Ser Asp Ile Ala Val Glu Trp Glu Ser Asn
            405                 410                 415
Gly Gln Pro Glu Asn Asn Tyr Lys Thr Thr Pro Pro Val Leu Asp Ser
```

-continued

```
            420                 425                 430
Asp Gly Ser Phe Phe Leu Tyr Ser Lys Leu Thr Val Asp Lys Ser Arg
            435                 440                 445

Trp Gln Gln Gly Asn Val Phe Ser Cys Ser Val Met His Glu Ala Leu
            450                 455                 460

His Asn His Tyr Thr Gln Lys Ser Leu Ser Leu Ser Pro Gly Lys
465                 470                 475

<210> SEQ ID NO 114
<211> LENGTH: 1440
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 114
atggacatga gggtgcccgc tcagctcctg gggctcctgc tgctgtggct gagaggtgcg      60
cgctgtgagg tgcagctggt ggagtctggg ggaggcttgg tacagcctgg ggggtccctg     120
agactctcct gtgcagcctc tggattcacc ttcagtagct atggcatgaa ctgggtccgc     180
caggctccag ggaagggact ggagtgggtt tcatacatta gtagtagtag tagtaccata     240
tactacgcag actctgtgaa gggccgattc accatctcca gagacaatgc caagaactca     300
ctgtatctgc aaatgaacag cctgagagac gaggacacgc tgtgtatta ctgtgcgaga     360 gataggatca ccagctggta cgaggaggac tactattact acggtatgga cgtctggggc     420
caagggacca cggtcaccgt ctctagtgcc tccaccaagg gcccatcggt cttcccctg      480 gcaccctcct ccaagagcac ctctgggggc acagcggccc tgggctgcct ggtcaaggac     540
tacttccccg aaccggtgac ggtgtcgtgg aactcaggcg ccctgaccag cggcgtgcac     600
accttcccgg ctgtcctaca gtcctcagga ctctactccc tcagcagcgt ggtgaccgtg     660
ccctccagca gcttgggcac ccagacctac atctgcaacg tgaatcacaa gcccagcaac     720
accaaggtgg acaagaaagt tgagcccaaa tcttgtgaca aaactcacac atgcccaccg     780
tgcccagcac ctgaactcct ggggggaccg tcagtcttcc tcttcccccc aaaacccaag     840
gacaccctca tgatctcccg gacccctgag gtcacatgcg tggtggtgga cgtgagccac     900
gaagaccctg aggtcaagtt caactggtac gtggacggcg tggaggtgca taatgccaag     960
acaaagccgc gggaggagca gtacaacagc acgtaccgtg tggtcagcgt cctcaccgtc    1020
ctgcaccagg actggctgaa tggcaaggag tacaagtgca aggtctccaa caaagccctc    1080
ccagccccca tcgagaaaac catctccaaa gccaaagggc agccccgaga accacaggtg    1140
tacaccctgc ccccatcccg ggaggagatg accaagaacc aggtcagcct gacctgcctg    1200
gtcaaaggct tctatcccag cgacatcgcc gtggagtggg agagcaatgg gcagccggag    1260
aacaactaca agaccacgcc tcccgtgctg gactccgacg gctccttctt cctctatagc    1320
aagctcaccg tggacaagag caggtggcag caggggaacg tcttctcatg ctccgtgatg    1380
catgaggctc tgcacaacca ctacacgcag aagagcctct ccctgtctcc gggtaaatga    1440
```

ANTI-ERYTHROPOIETIN ANTIBODIES

This application claims the benefit of U.S. Provisional Application No. 61/664,687 filed Jun. 26, 2012 and U.S. Provisional Application No. 61/643,742 filed May 7, 2012, both of which are incorporated by reference in their entirety.

REFERENCE TO THE SEQUENCE LISTING

The present application contains a Sequence Listing in electronic format. The Sequence Listing is provided as a file entitled A-1709-US-NP_SL.txt created Jul. 17, 2013, which is 131 KB in size. The information in the electronic format of the Sequence Listing is incorporated herein by reference in its entirety.

FIELD OF THE INVENTION

The field of this invention relates to compositions and methods related to anti-human erythropoietin antibodies.

BACKGROUND OF THE INVENTION

Erythropoietin (EPO) is a glycoprotein hormone necessary for the maturation of erythroid progenitor cells into erythrocytes. It is produced in the kidney and is essential in regulating levels of red blood cells in the circulation. Conditions marked by low levels of tissue oxygen signal increased production of EPO, which in turn stimulates erythropoiesis. A loss of kidney function as is seen in chronic renal failure, for example, typically results in decreased production of EPO and a concomitant reduction in red blood cells.

Human urinary EPO was purified by Miyake et al. (J. Biol. Chem. 252, 5558 (1977)) from patients with aplastic anemia. However, the amount of purified EPO protein obtained from this source was insufficient for therapeutic applications. The identification and cloning of the gene encoding human EPO and expression of recombinant protein was disclosed in U.S. Pat. No. 4,703,008 to Lin. A method for purification of recombinant human erythropoietin from cell medium is disclosed in U.S. Pat. No. 4,667,016 to Lai et. al. The production of biologically active EPO from mammalian host cells has made available, for the first time, quantities of EPO suitable for therapeutic applications. In addition, knowledge of the gene sequence and the increased availability of purified protein has led to a better understanding of the mode of action of this protein.

Nephrologists often treat anemia patients with recombinant erythropoietin. Antibody-mediated pure red cell aplasia (PRCA) is a rare, but serious complication than can result from antibodies that develop in a treated patient and neutralize both the recombinant EPO and endogenous EPO. Many assays are currently in use for detection of anti-EPO antibodies, but results from different assays are currently not comparable.

The testing for anti-ESA antibodies is critical to monitor ESA safety and efficacy during clinical development and in a post-market setting [Koren E, Zuckerman L A, Mire-Sluis A R Immune responses to therapeutic proteins in humans—clinical significance, assessment and prediction. Curr Pharm Biotechnol 2002; 3(4):349-360]. A variety of analytical immunoassay methods have been described to detect and characterize anti-drug antibodies (ADAs). Each screening method offers its own unique advantages and disadvantages [Thorpe R, Swanson S J. Current methods for detecting antibodies against erythropoietin and other recombinant proteins. Clin Diagn Lab Immunol 2005; 12(1):28-39].

The most commonly used immunoassay methods in the industry for detection of binding antibodies (BAbs) are the ELISA, radioimmunoprecipitation assay (RIA), Electrochemiluminescent (ECL) assay, and Surface Plasmon Resonance Immunoassay (SPRIA), all of which have been demonstrated to detect the pathogenic antibodies in patients that develop antibody-mediated pure red cell aplasia (amPRCA) [Barger T E, Kuck A J, Chirmule N, et al. Detection of anti-ESA antibodies in human samples from PRCA and non-PRCA patients: an immunoassay platform comparison. Nephrology Dialysis Transplantation 2012; 27(2):688-693].

Although ESAs are generally well tolerated, rare cases of amPRCA have been reported [Pollock C, Johnson D W, Horl W H, et al. Pure red cell aplasia induced by erythropoiesis-stimulating agents. Clin J Am Soc Nephrol 2008; 3(1):193-199; Schellekens H, Jiskoot W. Eprex-associated pure red cell aplasia and leachates. Nat Biotechnol 2006; 24(6):613-614]. The antibody response to ESAs in patients that develop amPRCA have been previously characterized using a SPRIA and demonstrated to be a mixed IgG predominated by IgG1 and IgG4 [Mytych D T, La S, Barger T, et al. The development and validation of a sensitive, dual-flow cell, SPR-based biosensor immunoassay for the detection, semi-quantitation, and characterization of antibodies to darbepoetin alfa and epoetin alfa in human serum. J Pharm Biomed Anal 2009; 49(2):415-426; Swanson S J, Ferbas J, Mayeux P, et al. Evaluation of methods to detect and characterize antibodies against recombinant human erythropoietin. Nephron Clin Pract 2004; 96(3):c88-c95; Mytych D T, Barger T E, King C, et al. Development and characterization of a human antibody reference panel against erythropoietin suitable for the standardization of ESA immunogenicity testing. 2012]. An anti-ESA IgG1 antibody response appeared in some antibody-positive non-PRCA patients [Evens A M, Bennett C L, Luminari S. Epoetin-induced pure red-cell aplasia (PRCA): preliminary results from the research on adverse drug events and reports (RADAR) group. Best Pract Res Clin Haematol 2005; 18(3):481-489] but is also present with the detection of IgG4 in patients that develop amPRCA [Casadevall N, Nataf J, Viron B, et al. Pure Red-Cell Aplasia and Antierythropoietin Antibodies in Patients Treated with Recombinant Erythropoietin. New England Journal of Medicine 2002; 346(7):469-475]. Although the IgG1 response is considered to precede the IgG4 response, the switch is driven by the repeated and prolonged exposure to the ESA. This is also well illustrated by the analysis of antibody to grass pollen and bee venom in novice beekeepers [Aalberse R C, van der Gaag R, van Leeuwen J. Serologic aspects of IgG4 antibodies. I. Prolonged immunization results in an IgG4-restricted response. J Immunol 1983; 130(2):722-726]. The long-term administration of biological therapeutics such as adalimumab in rheumatoid arthritis (RA) patients [van Schouwenburg P A, Krieckaert C L, Nurmohamed M, et al. IgG4 Production Against Adalimumab During Long Term Treatment of RA Patients. J Clin Immunol 2012], IFN-β 1b in multiple sclerosis patients [Deisenhammer F, Reindl M, Berger T Immunoglobulin subclasses in patients with neutralizing and nonneutralizing antibodies against IFN-beta1b. J Interferon Cytokine Res 2001; 21(3):167-171] and factor VIII to hemophilia A patients [van Belden P M, van den Berg H M, Gouw S C, et al. IgG subclasses of anti-FVIII antibodies during immune tolerance induction in patients with hemophilia A. CORD Conference Proceedings 2008; 142(4):644-652] results in the development of IgG4 ADA. The development of anti-ESA IgG4 antibodies against ESAs is best studied in the nephrology patient population and has been shown to be coincident with amPRCA.

In general, serum concentrations of the IgG subclasses are not evenly distributed. The serum concentration ranges in normal adults for IgG1, IgG2, and IgG3 are 3.8 to 9.3 mg/mL, 2.4 to 7.0 mg/mL and 0.22 to 1.76 mg/mL, respectively. The total IgG4 antibody is the least abundant in serum (4% of total IgG) with a normal range of 0.04 to 0.86 mg/mL in human serum [French M M. Serum IgG subclasses in normal adults. Monogr Allergy 1986; 19:100-107]. The appearance of drug-specific IgG antibodies generally corresponds with the maturation of a secondary antibody response upon repeated exposure and generally elicits a mixed IgG subclass response [Stavnezer J J. Molecular processes that regulate class switching. Curr Top Microbiol Immunol 2000; 245(2):127-168]. The prevalence of the IgG subclasses can be antigen-specific, and the chronic exposure of a protein has been shown to develop an IgG4 isotype restriction [Shakib F F. The IgG4 subclass. Monogr Allergy 1986; 19:223-226].

In the case of the antibody response to ESAs, the greatest analytic challenge with the current immunological methods is the ability to measure the low abundance of anti-ESA specific IgG4 antibodies in the presence of much higher concentrations of the other ESA-specific IgG subclasses. The only published method to detect, but not quantitate, the anti-ESA antibody isotype is the SPRIA methodology. The challenge is that the more predominant isotypes such as IgG1 and IgG2 saturate the ESA coated surface, making it difficult to detect the less abundant anti-IgG4 antibodies.

The technology to detect specific immunoglobulins has existed for more than 50 years and has been used successfully to detect specific IgE antibodies to allergens [Maloney J M, Rudengren M, Ahlstedt S, et al. The use of serum-specific IgE measurements for the diagnosis of peanut, tree nut, and seed allergy. J Allergy Clin Immunol 2008; 122(1): 145-151] and more recently the detection of antigen-specific IgG4 antibodies [Ito K, Futamura M, Moverare R, et al. The usefulness of casein-specific IgE and IgG4 antibodies in cow's milk allergic children. Clin Mol Allergy 2012; 10(1): 1-1]. The advantage of this technology is the large binding capacity, allowing the quantitation of low level antigen-specific antibody isotypes such as IgG4 and IgE in a pool of other specific antibodies.

Accordingly, there is a need for anti-human EPO antibodies that can be used in sensitive, reproducible assays. Of particular need are antibodies of high- and low-affinity with binding specificity to neutralizing and non-neutralizing EPO epitopes, including IgG1, IgG2, and IgG4 subclasses of antibodies, as well as an IgM isotype. Of further need is the development of a highly sensitive and specific immunoassay for the measurement of anti-ESA IgG4 antibodies.

SUMMARY OF THE INVENTION

In one embodiment, the invention provides an isolated antibody or fragment of an antibody, wherein the antibody or the fragment specifically binds to human erythropoietin and comprises: a VH CDR1 having an amino acid sequence identical to or comprising 0, 1, 2, or 3 amino acid residue substitutions relative to SEQ ID NO: 36; a VH CDR2 having an amino acid sequence identical to or comprising 0, 1, 2, or 3 amino acid residue substitutions relative to SEQ ID NO: 37; a VH CDR3 having an amino acid sequence identical to or comprising 0, 1, 2, or 3 amino acid residue substitutions relative to SEQ ID NO: 38; a VL CDR1 having an amino acid sequence identical to or comprising 0, 1, 2, or 3 amino acid residue substitutions relative to SEQ ID NO: 6; a VL CDR2 having an amino acid sequence identical to or comprising 0, 1, 2, or 3 amino acid residue substitutions relative to SEQ ID NO: 7; and a VL CDR3 having an amino acid sequence identical to or comprising 0, 1, 2, or 3 amino acid residue substitutions relative to SEQ ID NO: 8.

In another embodiment, the invention provides an isolated antibody or fragment of an antibody, wherein the antibody or the fragment specifically binds to human erythropoietin and comprises: a VH CDR1 having an amino acid sequence identical to or comprising 1, 2, or 3 amino acid residue substitutions relative to SEQ ID NO: 42; a VH CDR2 having an amino acid sequence identical to or comprising 1, 2, or 3 amino acid residue substitutions relative to SEQ ID NO: 43; a VH CDR3 having an amino acid sequence identical to or comprising 1, 2, or 3 amino acid residue substitutions relative to SEQ ID NO: 44; a VL CDR1 having an amino acid sequence identical to or comprising 1, 2, or 3 amino acid residue substitutions relative to SEQ ID NO: 12; a VL CDR2 having an amino acid sequence identical to or comprising 1, 2, or 3 amino acid residue substitutions relative to SEQ ID NO: 13; and a VL CDR3 having an amino acid sequence identical to or comprising 1, 2, or 3 amino acid residue substitutions relative to SEQ ID NO: 14.

In a further embodiment, the invention provides an isolated antibody or fragment of an antibody, wherein the antibody or the fragment specifically binds to human erythropoietin and comprises: a VH CDR1 having an amino acid sequence identical to or comprising 1, 2, or 3 amino acid residue substitutions relative to SEQ ID NO: 48; a VH CDR2 having an amino acid sequence identical to or comprising 1, 2, or 3 amino acid residue substitutions relative to SEQ ID NO: 49; a VH CDR3 having an amino acid sequence identical to or comprising 1, 2, or 3 amino acid residue substitutions relative to SEQ ID NO: 50; a VL CDR1 having an amino acid sequence identical to or comprising 1, 2, or 3 amino acid residue substitutions relative to SEQ ID NO: 18; a VL CDR2 having an amino acid sequence identical to or comprising 1, 2, or 3 amino acid residue substitutions relative to SEQ ID NO: 19; and a VL CDR3 having an amino acid sequence identical to or comprising 1, 2, or 3 amino acid residue substitutions relative to SEQ ID NO: 20.

In another embodiment, the invention provides an isolated antibody or fragment of an antibody, wherein the antibody or the fragment specifically binds to human erythropoietin and comprises: a VH CDR1 having an amino acid sequence identical to or comprising 1, 2, or 3 amino acid residue substitutions relative to SEQ ID NO: 54; a VH CDR2 having an amino acid sequence identical to or comprising 1, 2, or 3 amino acid residue substitutions relative to SEQ ID NO: 55; a VH CDR3 having an amino acid sequence identical to or comprising 1, 2, or 3 amino acid residue substitutions relative to SEQ ID NO: 56; a VL CDR1 having an amino acid sequence identical to or comprising 1, 2, or 3 amino acid residue substitutions relative to SEQ ID NO: 24; a VL CDR2 having an amino acid sequence identical to or comprising 1, 2, or 3 amino acid residue substitutions relative to SEQ ID NO: 25; and a VL CDR3 having an amino acid sequence identical to or comprising 1, 2, or 3 amino acid residue substitutions relative to SEQ ID NO: 26.

In a further embodiment, the invention provides an isolated antibody or fragment of an antibody, wherein the antibody or the fragment specifically binds to human erythropoietin and comprises: a VH CDR1 having an amino acid sequence identical to or comprising 1, 2, or 3 amino acid residue substitutions relative to SEQ ID NO: 60; a VH CDR2 having an amino acid sequence identical to or comprising 1, 2, or 3 amino acid residue substitutions relative to SEQ ID NO: 61; a VH CDR3 having an amino acid sequence identical to or comprising 1, 2, or 3 amino acid residue substitutions relative to SEQ ID NO: 62; a VL CDR1 having an amino acid sequence identical to or comprising 1, 2, or 3 amino acid residue substitutions relative to SEQ ID NO: 30; a VL CDR2 having an amino acid sequence identical to or comprising 1, 2, or 3 amino acid residue substitutions relative to SEQ ID NO: 31; and a VL CDR3 having an amino acid sequence identical to or comprising 1, 2, or 3 amino acid residue substitutions relative to SEQ ID NO: 32.

In yet another embodiment, the invention provides an isolated antibody or antibody fragment, wherein the antibody or the fragment specifically binds human erythropoietin and comprises a heavy chain variable domain having at least 90% identity to the amino acid of SEQ ID NO: 69 and comprises a light chain variable domain having at least 90% identity to the amino acid sequence of SEQ ID NO: 63.

In a further embodiment, the invention provides an isolated antibody or antibody fragment, wherein the antibody or the fragment specifically binds human erythropoietin and comprises a heavy chain variable domain having at least 90% identity to the amino acid of SEQ ID NO: 70 and comprises a light chain variable domain having at least 90% identity to the amino acid sequence of SEQ ID NO: 64.

In another embodiment, the invention provides an isolated antibody or antibody fragment, wherein the antibody or the fragment specifically binds human erythropoietin and comprises a heavy chain variable domain having at least 90% identity to the amino acid of SEQ ID NO: 71 and comprises a light chain variable domain having at least 90% identity to the amino acid sequence of SEQ ID NO: 65.

In a further embodiment, the invention provides an isolated antibody or antibody fragment, wherein the antibody or the fragment specifically binds human erythropoietin and comprises a heavy chain variable domain having at least 90% identity to the amino acid of SEQ ID NO: 72 and comprises a light chain variable domain having at least 90% identity to the amino acid sequence of SEQ ID NO: 65.

In another embodiment, the invention provides an isolated antibody or antibody fragment, wherein the antibody or the fragment specifically binds human erythropoietin and comprises a heavy chain variable domain having at least 90% identity to the amino acid of SEQ ID NO: 73 and comprises a light chain variable domain having at least 90% identity to the amino acid sequence of SEQ ID NO: 66.

In another embodiment, the invention provides an isolated antibody or antibody fragment, wherein the antibody or the fragment specifically binds human erythropoietin and comprises a heavy chain variable domain having at least 90% identity to the amino acid of SEQ ID NO: 74 and comprises a light chain variable domain having at least 90% identity to the amino acid sequence of SEQ ID NO: 66.

In a further embodiment, the invention provides an isolated antibody or antibody fragment, wherein the antibody or the fragment specifically binds human erythropoietin and comprises a heavy chain variable domain having at least 90% identity to the amino acid of SEQ ID NO: 75 and comprises a light chain variable domain having at least 90% identity to the amino acid sequence of SEQ ID NO: 67.

In another embodiment, the invention provides an isolated antibody or antibody fragment, wherein the antibody or the fragment specifically binds human erythropoietin and comprises a heavy chain variable domain having at least 90% identity to the amino acid of SEQ ID NO: 76 and comprises a light chain variable domain having at least 90% identity to the amino acid sequence of SEQ ID NO: 68.

In one embodiment, the invention provides a method of measuring anti-human erythropoietin IgG4 antibody levels in a human subject comprising determining in vitro a level of anti-human erythropoietin IgG4 antibodies in a sample from said subject and comparing said level to a level obtained from the anti-human erythropoietin IgG4 antibody 8C10 or 3A4.

In another embodiment, the invention provides a method of measuring anti-human erythropoietin IgG4 antibody levels in a human subject comprising: contacting in vitro a blood or serum sample from said subject with a human erythropoietin, wherein the human erythropoietin captures anti-human IgG4 antibodies; contacting in vitro antibody 8C10 or 3A4 with a human erythropoietin, wherein the human erythropoietin captures 8C10 or 3A4; contacting said captured antibodies of steps a) and b) with a secondary anti-human IgG4 antibody that has been detectably labeled; and measuring the levels of said secondary antibody in each sample from step c).

In a further embodiment, the invention provides a method of detecting antibody-mediated pure red cell aplasia (amPRCA) in a human subject comprising determining in vitro a level of anti-human erythropoietin IgG4 antibodies in a sample from said subject and comparing said level to a level obtained from the anti-human erythropoietin IgG4 antibody 8C10 or 3A4, wherein an increase in a subject's anti-erythropoietin IgG4 levels indicates the onset or risk of amPRCA.

In another embodiment, the invention provides a method of predicting the onset of antibody-mediated pure red cell aplasia (amPRCA) comprising determining in vitro a level of anti-human erythropoietin IgG4 antibodies in a sample from said subject and comparing said level to a level obtained from the anti-human erythropoietin IgG4 antibody 8C10 or 3A4, wherein an increase in a subject's anti-erythropoietin IgG4 levels indicates the onset or risk of amPRCA.

In yet another embodiment, the invention provides a method of predicting the risk of antibody-mediated pure red cell aplasia (amPRCA) comprising determining in vitro a level of anti-human erythropoietin IgG4 antibodies in a sample from said subject and comparing said level to a level obtained from the anti-human erythropoietin IgG4 antibody 8C10 or 3A4, wherein an increase in a subject's anti-erythropoietin IgG4 levels indicates the onset or risk of amPRCA.

In one embodiment, the invention provides a kit for detecting amPRCA or predicting the risk or onset of amPRCA comprising an anti-human erythropoietin IgG4 antibody and human erythropoietin.

BRIEF DESCRIPTION OF THE FIGURES

FIG. 4. Topographical map illustrating human anti-EPO neutralizing antibody 8C10 and 3F5 binding to site 1 and 3A4 binding to site 2 on EPO; Non-neutralizing 9F7. The antibody 11D12 is not shown on this model.

FIG. 8. This is a graphical representation of a Wilcoxon Two-Sample test showing distribution of the anti-ESA IgG4 concentration (in ng/mL) displayed on the Y-axis and the patient classification of amPRCA and non-PRCA patients on the x-axis.

DETAILED DESCRIPTION OF THE INVENTION

Figure 1:
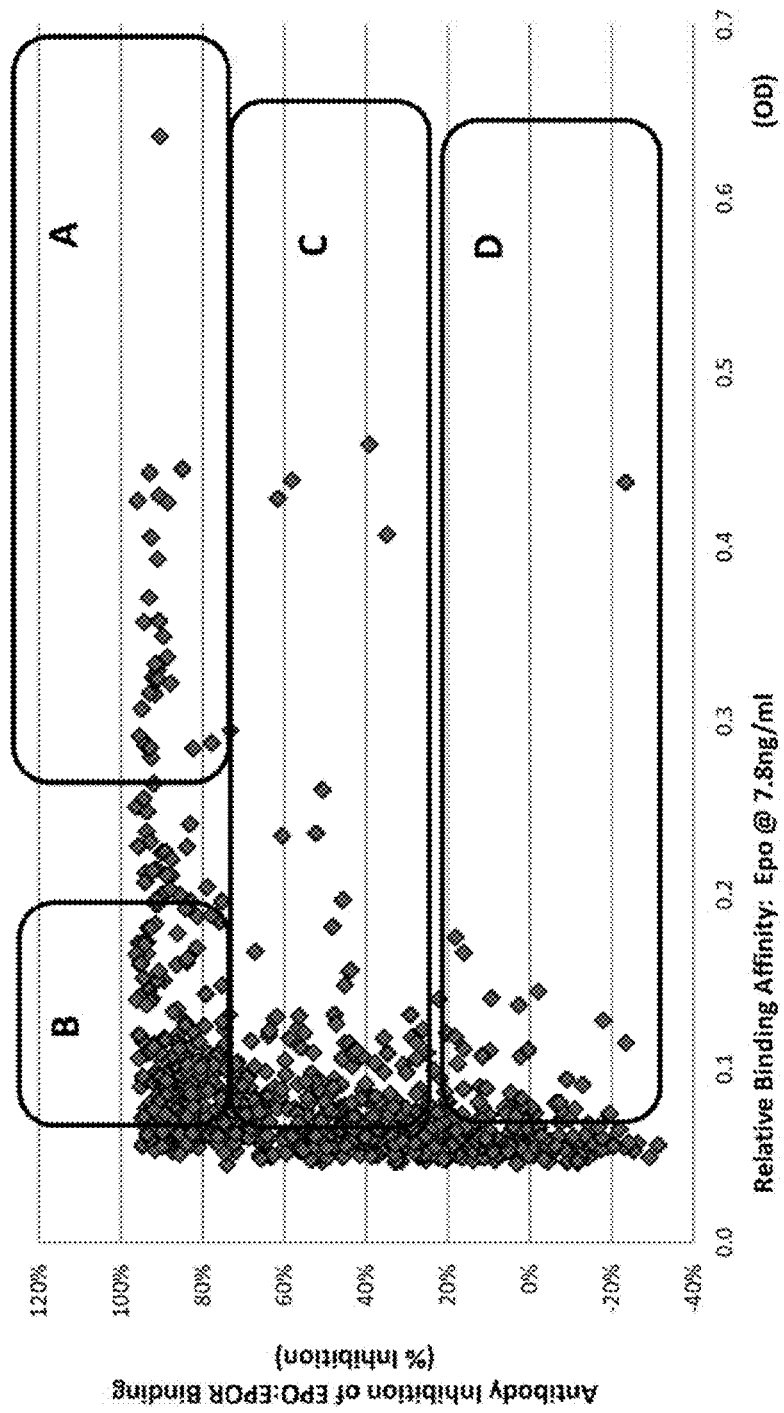
FIG. 1. A total of 792 anti-EPO hybridoma culture supernatants are compared for the ability to inhibit EPO binding to EPO receptor against the relative binding affinity to EPO by limited antigen equilibrium binding ELISA. Data is used to qualitatively categorize antibodies into 4 bins: A. high inhibition/mixed affinity; B. high inhibition/low affinity; C. moderate inhibition/mixed affinity; D. low inhibition and mixed affinity.

The present invention relates to antibodies that specifically bind to human erythropoietin. The present invention further provides compositions, kits, and methods relating to antibodies that specifically bind to human erythropoietin. Also provided are nucleic acid molecules, and derivatives and fragments thereof, comprising a sequence of polynucleotides that encode all or a portion of a polypeptide that binds to human erythropoietin, such as a nucleic acid encoding all or part of an anti-human erythropoietin antibody, antibody fragment, or antibody derivative. The present invention further provides vectors and plasmids comprising such nucleic acids, and cells or cell lines comprising such nucleic acids and/or vectors and plasmids. The provided methods include, for example, methods of making, identifying, or isolating anti-human erythropoietin antibodies, methods of determining whether an antibody binds to human erythropoietin, methods of making compositions, such as pharmaceutical compositions, comprising an antibody that binds to human erythropoietin, and methods of detecting, diagnosing and predicting antibody mediated pure red cell aplasia (amPRCA).

DEFINITIONS

Polynucleotide and polypeptide sequences are indicated using standard one- or three-letter abbreviations. Unless otherwise indicated, polypeptide sequences have their amino termini at the left and their carboxy termini at the right, and single-stranded nucleic acid sequences, and the top strand of double-stranded nucleic acid sequences, have their 5' termini at the left and their 3' termini at the right. A particular section of a polypeptide can be designated by amino acid residue number such as amino acids 1 to 50, or by the actual residue at that site such as asparagine to proline. A particular polypeptide or polynucleotide sequence also can be described by explaining how it differs from a reference sequence.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

The following terms, unless otherwise indicated, shall be understood to have the following meanings: The term "isolated molecule" (where the molecule is, for example, a polypeptide, a polynucleotide, or an antibody) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

The terms "peptide" "polypeptide" and "protein" each refers to a molecule comprising two or more amino acid residues joined to each other by peptide bonds. These terms encompass, e.g., native and artificial proteins, protein fragments and polypeptide analogs (such as muteins, variants, and fusion proteins) of a protein sequence as well as post-translationally, or otherwise covalently or non-covalently, modified proteins. A peptide, polypeptide, or protein may be monomeric or polymeric.

The term "polypeptide fragment" as used herein refers to a polypeptide that has an amino-terminal and/or carboxy-terminal deletion as compared to a corresponding full-length protein. Fragments can be, for example, at least 5, 6, 7, 8, 9, 10, 11, 12, 13, 14, 15, 20, 50, 70, 80, 90, 100, 150 or 200 amino acids in length. Fragments can also be, for example, at most 1,000, 750, 500, 250, 200, 175, 150, 125, 100, 90, 80, 70, 60, 50, 40, 30, 20, 15, 14, 13, 12, 11, or 10 amino acids in length. A fragment can further comprise, at either or both of its ends, one or more additional amino acids, for example, a sequence of amino acids from a different naturally-occurring protein (e.g., an Fc or leucine zipper domain) or an artificial amino acid sequence (e.g., an artificial linker sequence).

Polypeptides of the invention include polypeptides that have been modified in any way and for any reason, for example, to: (1) reduce susceptibility to proteolysis, (2) reduce susceptibility to oxidation, (3) alter binding affinity for forming protein complexes, (4) alter binding affinities, and (4) confer or modify other physicochemical or functional properties. Analogs include muteins of a polypeptide. For example, single or multiple amino acid substitutions (e.g., conservative amino acid substitutions) may be made in the naturally occurring sequence (e.g., in the portion of the polypeptide outside the domain(s) forming intermolecular contacts). A "conservative amino acid substitution" is one that does not substantially change the structural characteristics of the parent sequence (e.g., a replacement amino acid should not tend to break a helix that occurs in the parent sequence, or disrupt other types of secondary structure that characterize the parent sequence or are necessary for its functionality). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. Nature 354:105 (1991), which are each incorporated herein by reference.

A "variant" of a polypeptide (e.g., an antibody) comprises an amino acid sequence wherein one or more amino acid residues are inserted into, deleted from and/or substituted into the amino acid sequence relative to another polypeptide sequence. Variants of the invention include fusion proteins.

A "derivative" of a polypeptide is a polypeptide (e.g., an antibody) that has been chemically modified, e.g., via conjugation to another chemical moiety such as, for example, polyethylene glycol, albumin (e.g., human serum albumin), phosphorylation, and glycosylation. Unless otherwise indicated, the term "antibody" includes, in addition to antibodies comprising two full-length heavy chains and two full-length light chains, derivatives, variants, fragments, and muteins thereof, examples of which are described below.

An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

Naturally occurring immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat et al. in Sequences of Proteins of Immunological Interest, $5^{th}$ Ed., US Dept. of Health and Human Services, PHS, NIH, NIH Publication no. 91-3242, 1991.

An "antibody" refers to an intact immunoglobulin or to an antigen binding portion thereof that competes with the intact antibody for specific binding, unless otherwise specified. Antigen binding portions may be produced by recombinant DNA techniques or by enzymatic or chemical cleavage of intact antibodies. Antigen binding portions include, inter alia, Fab, Fab', F(ab')$_2$, Fv, domain antibodies (dAbs), fragments including complementarity determining regions (CDRs), single-chain antibodies (scFv), chimeric antibodies, diabodies, triabodies, tetrabodies, and polypeptides that contain at least a portion of an immunoglobulin that is sufficient to confer specific antigen binding to the polypeptide.

A Fab fragment is a monovalent fragment having the $V_L$, $V_H$, $C_L$ and $C_H1$ domains; a F(ab')$_2$ fragment is a bivalent fragment having two Fab fragments linked by a disulfide bridge at the hinge region; a Fd fragment has the $V_H$ and $C_H1$ domains; an Fv fragment has the $V_L$ and $V_H$ domains of a single arm of an antibody; and a dAb fragment has a $V_H$ domain, a $V_L$ domain, or an antigen-binding fragment of a $V_H$ or $V_L$ domain (U.S. Pat. Nos. 6,846,634, 6,696,245, US App. Pub. No. 05/0202512, 04/0202995, 04/0038291, 04/0009507, 03/0039958, Ward et al., Nature 341:544-546 (1989)).

A single-chain antibody (scFv) is an antibody in which a $V_L$ and a $V_H$ region are joined via a linker (e.g., a synthetic sequence of amino acid residues) to form a continuous protein chain wherein the linker is long enough to allow the protein chain to fold back on itself and form a monovalent antigen binding site (see, e.g., Bird et al., Science 242:423-26 (1988) and Huston et al., 1988, Proc. Natl. Acad. Sci. USA 85:5879-83 (1988)). Diabodies are bivalent antibodies comprising two polypeptide chains, wherein each polypeptide chain comprises $V_H$ and $V_L$ domains joined by a linker that is too short to allow for pairing between two domains on the same chain, thus allowing each domain to pair with a complementary domain on another polypeptide chain (see, e.g., Holliger et al., 1993, Proc. Natl. Acad. Sci. USA 90:6444-48 (1993), and Poljak et al., Structure 2:1121-23 (1994)). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

Complementarity determining regions (CDRs) and framework regions (FR) of a given antibody may be identified using the system described by Kabat et al. in Sequences of Proteins of Immunological Interest, 5th Ed., US Dept. of Health and Human Services, PHS, NIH, NIH Publication no. 91-3242, 1991. One or more CDRs may be incorporated into a molecule either covalently or noncovalently to make it an antibody. An antibody may incorporate the CDR(s) as part of a larger polypeptide chain, may covalently link the CDR(s) to another polypeptide chain, or may incorporate the CDR(s) noncovalently. The CDRs permit the antibody to specifically bind to a particular antigen of interest. In one embodiment, the invention contemplates a binding molecule that comprises at least one, at least two, at least three, at least four, at least five, or six CDRs from the antibodies of the invention.

An antibody may have one or more binding sites. If there is more than one binding site, the binding sites may be identical to one another or may be different. For example, a naturally occurring human immunoglobulin typically has two identical binding sites, while a "bispecific" or "bifunctional" antibody has two different binding sites.

The term "human antibody" includes all antibodies that have one or more variable and constant regions derived from human immunoglobulin sequences. In one embodiment, all of the variable and constant domains are derived from human immunoglobulin sequences (a fully human antibody). These antibodies may be prepared in a variety of ways known in the art, nonlimiting examples of which are described herein, including through the immunization with an antigen of interest of a mouse that is genetically modified to express antibodies derived from human heavy and/or light chain-encoding genes.

A humanized antibody has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies may be found in U.S. Pat. Nos. 6,054,297, 5,886,152 and 5,877,293.

The term "chimeric antibody" refers to an antibody that contains one or more regions from one antibody and one or more regions from one or more other antibodies. In one embodiment, one or more of the CDRs are derived from a human anti-human erythropoietin antibody. In another embodiment, all of the CDRs are derived from a human anti-human erythropoietin antibody. In another embodiment, the CDRs from more than one human anti-human erythropoietin antibodies are mixed and matched in a chimeric antibody. For instance, a chimeric antibody may comprise a CDR1 from the light chain of a first human anti-human erythropoietin antibody, a CDR2 and a CDR3 from the light chain of a second human anti-human erythropoietin antibody, and the CDRs from the heavy chain from a third anti-human erythropoietin antibody. Further, the framework regions may be derived from one of the same anti-human erythropoietin antibodies, from one or more different antibodies, such as a human antibody, or from a humanized antibody. In one example of a chimeric antibody, a portion of the heavy and/or light chain is identical with, homologous to, or derived from an antibody from a particular species or belonging to a particular antibody class or subclass, while the remainder of the chain(s) is/are identical with, homologous to, or derived from an antibody or antibodies from another species or belonging to another antibody class or subclass. Also included are fragments of such antibodies that exhibit the desired biological activity (i.e., the ability to specifically bind the human erythropoietin).

A "neutralizing antibody" or "inhibitory antibody" refers to an antibody that inhibits the binding of ligand to the receptor, and/or inhibits or reduces receptor signalling. The inhibition need not be complete and may be, in one embodiment, reduced binding or signalling by at least 20%. In further embodiments, the reduction in binding or signalling is at least 30%, 40%, 50%, 60%, 70%, 80%, 85%, 90%, 95%, 97%, 99% and 99.9%.

Fragments or analogs of antibodies can be readily prepared by those of ordinary skill in the art following the teachings of this specification and using techniques well-known in the art. Preferred amino- and carboxy-termini of fragments or analogs occur near boundaries of functional domains. Structural and functional domains can be identified by comparison of the nucleotide and/or amino acid sequence data to public or proprietary sequence databases. Computerized comparison methods can be used to identify sequence motifs or predicted protein conformation domains that occur in other proteins of known structure and/or function. Methods to identify protein sequences that fold into a known three-dimensional structure are known. See, e.g., Bowie et al., Science 253:164 (1991).

A "CDR grafted antibody" is an antibody comprising one or more CDRs derived from an antibody of a particular species or isotype and the framework of another antibody of the same or different species or isotype.

A "multi-specific antibody" is an antibody that recognizes more than one epitope on one or more antigens. A subclass of this type of antibody is a "bi-specific antibody" which recognizes two distinct epitopes on the same or different antigens.

An antibody "specifically binds" to an antigen, such as human erythropoietin if it binds to the antigen with a high binding affinity as determined by a dissociation constant (Kd, or corresponding Kb, as defined below) value of $10^{-7}$ M or less.

An "epitope" is the portion of a molecule that is bound by an antibody. An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antibody).

The "percent identity" of two polynucleotide or two polypeptide sequences is determined by comparing the sequences using the GAP computer program (a part of the GCG Wisconsin Package, version 10.3 (Accelrys, San Diego, Calif.)) using its default parameters.

The terms "polynucleotide," "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In one embodiment, the nucleic acid molecules of the invention comprise a contiguous open reading frame encoding an antibody, or a fragment, derivative, mutein, or variant thereof, of the invention.

Two single-stranded polynucleotides are "the complement" of each other if their sequences can be aligned in an anti-parallel orientation such that every nucleotide in one polynucleotide is opposite its complementary nucleotide in the other polynucleotide, without the introduction of gaps, and without unpaired nucleotides at the 5' or the 3' end of either sequence. A polynucleotide is "complementary" to another polynucleotide if the two polynucleotides can hybridize to one another under moderately stringent conditions. Thus, a polynucleotide can be complementary to another polynucleotide without being its complement.

A "vector" is a nucleic acid that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: Methods in Enzymology 185, Academic Press, San Diego, Calif. and Baron et al., 1995, Nucleic Acids Res. 23:3605-06.

A "host cell" is a cell that can be used to express a nucleic acid, e.g., a nucleic acid of the invention. A host cell can be a prokaryote, for example, E. coli, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but to the progeny or potential progeny of such a cell. Because certain modifications may occur in succeeding generations due to, e.g., mutation or environmental influence, such progeny may not, in fact, be identical to the parent cell, but are still included within the scope of the term as used herein.

Erythropoietin

Erythropoietin is a glycoprotein hormone involved in the maturation of erythroid progenitor cells into erythrocytes. It is essential in regulating levels of red blood cells in circulation. Naturally occurring erythropoietin is produced by the liver during fetal life and by the kidney of adults and circulates in the blood and stimulates the production of red blood cells in bone marrow. Anemia is almost invariably a consequence of renal failure due to decreased production of erythropoietin from the kidney. Recombinant erythropoietin produced by genetic engineering techniques involving the expression of a protein product from a host cell transformed with the gene encoding erythropoietin has been found to be effective when used in the treatment of anemia resulting from chronic renal failure.

The identification, cloning, and expression of genes encoding erythropoietin are described in U.S. Pat. No. 4,703,008 to Lin. A description of the purification of recombinant erythropoietin from cell medium that supported the growth of mammalian cells containing recombinant erythropoietin plasmids for example, is included in U.S. Pat. No. 4,667,016 to Lai et al. The expression and recovery of biologically active recombinant erythropoietin from mammalian cell hosts containing the erythropoietin gene on recombinant plasmids has made available quantities of erythropoietin suitable for therapeutic applications. The polynucleotide and polypeptide sequences for several species of erythropoietin are known. Table 1 presents nonlimiting examples of available sequences for human erythropoietin; the arginine at position 166 is optionally deleted.

TABLE 1

Erythropoietin Sequences

Human (Homo sapiens) polynucleotides (SEQ ID NO: 1)
AGCTTCCCGGGATGAGGGCCCCCGGTGTGGTCACCCGGCGCGCCCCAGGT
CGCTGAGGGACCCCGGCCAGGCGCGGAGATGGGGGTGCACGAATGTCCTG
CCTGGCTGTGGCTTCTCCTGTCCCTGCTGTCGCTCCCTCTGGGCCTCCCA
GTCCTGGGCGCCCACCACGCCTCATCTGTGACAGCCGAGTCCTGGAGAG
GTACCTCTTGGAGGCCAAGGAGGCCGAGAATATCACGACGGGCTGTGCTG
AACACTGCAGCTTGAATGAGAATATCACTGTCCCAGACACCAAAGTTAAT
TTCTATGCCTGGAAGAGGATGGAGGTCGGGCAGCAGGCCGTAGAAGTCTG
GCAGGGCCTGGCCCTGCTGTCGGAAGCTGTCCTGCGGGGCCAGGCCCTGT
TGGTCAACTCTTCCCAGCCGTGGGAGCCCCTGCAGCTGCATGTGGATAAA
GCCGTCAGTGGCCTTCGCAGCCTCACCACTCTGCTTCGGGCTCTGGGAGC
CCAGGAAGCCATCTCCCCTCCAGATGCGGCCTCAGCTGCTCCACTCCGAA
CAATCACTGCTGACACTTTCCGCAAACTCTTCCGAGTCTACTCCAATTTC TABLE 1-continued Erythropoietin Sequences

```
CTCCGGGGAAAGCTGAAGCTGTACACAGGGGAGGCCTGCAGGACAGGGGA
CAGATGACCAGGTGTGTCCACCTGGGCATATCCACCACCTCCCTCACCAA
CATTGCTTGTGCCACACCCTCCCCCGCCACTCCTGAACCCCGTC

Human (Homo sapiens) amino acid (SEQ ID NO: 2)
APPRLICDSRVLERYLLEAKEAENITTGCAEHCSLNENITVPDTKVNFYA
WKRMEVGQQAVEVWQGLALLSEAVLRGQALLVNSSQPWEPLQLHVDKAVS
GLRSLTTLLRALGAQKEAISPPDAASAAPLRTITADTFRKLFRVYSNFLR
GKLKLYTGEACRTGDR
```

Antibodies

In one aspect, the present invention provides antibodies, antibody fragments, antibody derivatives, antibody muteins, and antibody variants, that specifically bind to human erythropoietin. In one embodiment the antibody is a human antibody. In one embodiment, the invention provides an isolated antibody or fragment of an antibody, wherein the antibody or the fragment specifically binds to human erythropoietin and comprises: a VH CDR1 having an amino acid sequence identical to or comprising 0, 1, 2, or 3 amino acid residue substitutions relative to SEQ ID NO: 36; a VH CDR2 having an amino acid sequence identical to or comprising 0, 1, 2, or 3 amino acid residue substitutions relative to SEQ ID NO: 37; a VH CDR3 having an amino acid sequence identical to or comprising 0, 1, 2, or 3 amino acid residue substitutions relative to SEQ ID NO: 38; a VL CDR1 having an amino acid sequence identical to or comprising 0, 1, 2, or 3 amino acid residue substitutions relative to SEQ ID NO: 6; a VL CDR2 having an amino acid sequence identical to or comprising 0, 1, 2, or 3 amino acid residue substitutions relative to SEQ ID NO: 7; and a VL CDR3 having an amino acid sequence identical to or comprising 0, 1, 2, or 3 amino acid residue substitutions relative to SEQ ID NO: 8.

In another embodiment, the invention provides an isolated antibody or fragment of an antibody, wherein the antibody or the fragment specifically binds to human erythropoietin and comprises: a VH CDR1 having an amino acid sequence identical to or comprising 1, 2, or 3 amino acid residue substitutions relative to SEQ ID NO: 42; a VH CDR2 having an amino acid sequence identical to or comprising 1, 2, or 3 amino acid residue substitutions relative to SEQ ID NO: 43; a VH CDR3 having an amino acid sequence identical to or comprising 1, 2, or 3 amino acid residue substitutions relative to SEQ ID NO: 44; a VL CDR1 having an amino acid sequence identical to or comprising 1, 2, or 3 amino acid residue substitutions relative to SEQ ID NO: 12; a VL CDR2 having an amino acid sequence identical to or comprising 1, 2, or 3 amino acid residue substitutions relative to SEQ ID NO: 13; and a VL CDR3 having an amino acid sequence identical to or comprising 1, 2, or 3 amino acid residue substitutions relative to SEQ ID NO: 14.

In a further embodiment, the invention provides an isolated antibody or fragment of an antibody, wherein the antibody or the fragment specifically binds to human erythropoietin and comprises: a VH CDR1 having an amino acid sequence identical to or comprising 1, 2, or 3 amino acid residue substitutions relative to SEQ ID NO: 48; a VH CDR2 having an amino acid sequence identical to or comprising 1, 2, or 3 amino acid residue substitutions relative to SEQ ID NO: 49; a VH CDR3 having an amino acid sequence identical to or comprising 1, 2, or 3 amino acid residue substitutions relative to SEQ ID NO: 50; a VL CDR1 having an amino acid sequence identical to or comprising 1, 2, or 3 amino acid residue substitutions relative to SEQ ID NO: 18; a VL CDR2 having an amino acid sequence identical to or comprising 1, 2, or 3 amino acid residue substitutions relative to SEQ ID NO: 19; and a VL CDR3 having an amino acid sequence identical to or comprising 1, 2, or 3 amino acid residue substitutions relative to SEQ ID NO: 20.

In another embodiment, the invention provides an isolated antibody or fragment of an antibody, wherein the antibody or the fragment specifically binds to human erythropoietin and comprises: a VH CDR1 having an amino acid sequence identical to or comprising 1, 2, or 3 amino acid residue substitutions relative to SEQ ID NO: 54; a VH CDR2 having an amino acid sequence identical to or comprising 1, 2, or 3 amino acid residue substitutions relative to SEQ ID NO: 55; a VH CDR3 having an amino acid sequence identical to or comprising 1, 2, or 3 amino acid residue substitutions relative to SEQ ID NO: 56; a VL CDR1 having an amino acid sequence identical to or comprising 1, 2, or 3 amino acid residue substitutions relative to SEQ ID NO: 24; a VL CDR2 having an amino acid sequence identical to or comprising 1, 2, or 3 amino acid residue substitutions relative to SEQ ID NO: 25; and a VL CDR3 having an amino acid sequence identical to or comprising 1, 2, or 3 amino acid residue substitutions relative to SEQ ID NO: 26.

In a further embodiment, the invention provides an isolated antibody or fragment of an antibody, wherein the antibody or the fragment specifically binds to human erythropoietin and comprises: a VH CDR1 having an amino acid sequence identical to or comprising 1, 2, or 3 amino acid residue substitutions relative to SEQ ID NO: 60; a VH CDR2 having an amino acid sequence identical to or comprising 1, 2, or 3 amino acid residue substitutions relative to SEQ ID NO: 61; a VH CDR3 having an amino acid sequence identical to or comprising 1, 2, or 3 amino acid residue substitutions relative to SEQ ID NO: 62; a VL CDR1 having an amino acid sequence identical to or comprising 1, 2, or 3 amino acid residue substitutions relative to SEQ ID NO: 30; a VL CDR2 having an amino acid sequence identical to or comprising 1, 2, or 3 amino acid residue substitutions relative to SEQ ID NO: 31; and a VL CDR3 having an amino acid sequence identical to or comprising 1, 2, or 3 amino acid residue substitutions relative to SEQ ID NO: 32.

In yet another embodiment, the invention provides an isolated antibody or antibody fragment, wherein the antibody or the fragment specifically binds human erythropoietin and comprises a heavy chain variable domain having at least 90% identity to the amino acid of SEQ ID NO: 69 and comprises a light chain variable domain having at least 90% identity to the amino acid sequence of SEQ ID NO: 63.

In a further embodiment, the invention provides an isolated antibody or antibody fragment, wherein the antibody or the fragment specifically binds human erythropoietin and comprises a heavy chain variable domain having at least 90% identity to the amino acid of SEQ ID NO: 70 and comprises a light chain variable domain having at least 90% identity to the amino acid sequence of SEQ ID NO: 64.

In another embodiment, the invention provides an isolated antibody or antibody fragment, wherein the antibody or the fragment specifically binds human erythropoietin and comprises a heavy chain variable domain having at least 90% identity to the amino acid of SEQ ID NO: 71 and comprises a light chain variable domain having at least 90% identity to the amino acid sequence of SEQ ID NO: 65.

In a further embodiment, the invention provides an isolated antibody or antibody fragment, wherein the antibody or the fragment specifically binds human erythropoietin and comprises a heavy chain variable domain having at least 90% identity to the amino acid of SEQ ID NO: 72 and comprises a light chain variable domain having at least 90% identity to the amino acid sequence of SEQ ID NO: 65.

In another embodiment, the invention provides an isolated antibody or antibody fragment, wherein the antibody or the fragment specifically binds human erythropoietin and comprises a heavy chain variable domain having at least 90% identity to the amino acid of SEQ ID NO: 73 and comprises a light chain variable domain having at least 90% identity to the amino acid sequence of SEQ ID NO: 66.

In another embodiment, the invention provides an isolated antibody or antibody fragment, wherein the antibody or the fragment specifically binds human erythropoietin and comprises a heavy chain variable domain having at least 90% identity to the amino acid of SEQ ID NO: 74 and comprises a light chain variable domain having at least 90% identity to the amino acid sequence of SEQ ID NO: 66.

In a further embodiment, the invention provides an isolated antibody or antibody fragment, wherein the antibody or the fragment specifically binds human erythropoietin and comprises a heavy chain variable domain having at least 90% identity to the amino acid of SEQ ID NO: 75 and comprises a light chain variable domain having at least 90% identity to the amino acid sequence of SEQ ID NO: 67.

In another embodiment, the invention provides an isolated antibody or antibody fragment, wherein the antibody or the fragment specifically binds human erythropoietin and comprises a heavy chain variable domain having at least 90% identity to the amino acid of SEQ ID NO: 76 and comprises a light chain variable domain having at least 90% identity to the amino acid sequence of SEQ ID NO: 68.

In one embodiment, the antibody comprises sequences that each independently differ by 5, 4, 3, 2, 1, or 0 single amino acid additions, substitutions, and/or deletions from a CDR sequence of those listed in Table 2 below. As used herein, a CDR sequence that differs by no more than a total of, for example, four amino acid additions, substitutions and/or deletions from a CDR sequence shown in Table 2 below refers to a sequence with 4, 3, 2, 1 or 0 single amino acid additions, substitutions, and/or deletions compared with the sequences shown in Table 2.

The light chain CDRs of exemplary antibodies and the heavy chain CDRs of exemplary antibodies are shown below in Table 2. Also shown are polynucleotide sequences which encode the amino acid sequences of the CDRs.

TABLE 2

| | LIGHT CHAINS | | |
|---|---|---|---|
| Ab | CDR 1 | CDR 2 | CDR 3 |
| Ab3A4 NA | CAGGCGAGTCAGGACATTAGCA ACTTTTTGAAT (SEQ ID NO: 3) | GATGCATCCAATTTGGA AACA (SEQ ID NO: 4) | CAACAGTATGATAA TTTCCCGCTCACT (SEQ ID NO: 5) |
| AA | QASQDISNFLN (SEQ ID NO: 6) | DASNLET (SEQ ID NO: 7) | QQYDNFPLT (SEQ ID NO: 8) |
| Ab3F5 NA | CAGGCGAGTCAGGACATTAGCA ACTATTTAAAT (SEQ ID NO: 9) | GATGCATCCAATTTGGA AACA (SEQ ID NO: 10) | CAACAGTATGATGA TCTCCCGCTCACT (SEQ ID NO: 11) |
| AA | QASQDISNYLN (SEQ ID NO: 12) | DASNLET (SEQ ID NO: 13) | QQYDDLPLT (SEQ ID NO: 14) |
| Ab8C10 NA | GGGGGAAACAACATTGGAAGTA AAAGTGTGCAC (SEQ ID NO: 15) | GATGATAGCGACCGCC CTCA (SEQ ID NO: 16) | CAGGTGTGGGATAG TAGTGGTGATCATC CGGTA (SEQ ID NO: 17) |
| AA | GGNNIGSKSVH (SEQ ID NO: 18) | DDSDRPS (SEQ ID NO: 19) | QVWDSSGDHPV (SEQ ID NO: 20) |
| Ab9F7 NA | AGGGCCAGTCAGAGGGGTAATA ACAACTTAGCC (SEQ ID NO: 21) | GGTGCATCCACCAGGGC CACT (SEQ ID NO: 22) | CAGCAGTATAATAT CTGGCCTCGCAGT (SEQ ID NO: 23) |
| AA | RASQRGNNNLA (SEQ ID NO: 24) | GASTRAT (SEQ ID NO: 25) | QQYNIWPRS (SEQ ID NO: 26) |
| Ab11D12 NA | ACCCTGAGCAGCGGCTACAGTA ATTATAAAGTGGAC (SEQ ID NO: 27) | GTGGGCACTGGTGGGAT TGGGATCCAAGGGGG AT (SEQ ID NO: 28) | GGGGCAGACCATGG CAGTGGGAGCAACT TCGTGTGGGTG (SEQ ID NO: 29) |
| AA | TLSSGYSNYKVD (SEQ ID NO: 30) | VGTGGIVGSKGD (SEQ ID NO: 31) | GADHGSGSNFVWV (SEQ ID NO: 32) |
| | HEAVY CHAINS | | |
| Ab | CDR 1 | CDR 2 | CDR 3 |
| Ab3A4 NA | ACCTATGGTATCAA C (SEQ ID NO: 33) | TGGCTCAGCGCTTACAGTGGTA ACACAAACTATGCACAGAAACT CCAGGGC (SEQ ID NO: 34) | GGAGTGGGAGCTTCCTTTTACTTTG ACTAC (SEQ ID NO: 35) |
| AA | TYGIN (SEQ ID NO: 36) | WLSAYSGNTNYAQKLQG (SEQ ID NO: 37) | GVGASFYFDY (SEQ ID NO: 38) |
| Ab3F5 NA | AGCTATGGCATGAA C (SEQ ID NO: 39) | TACATTAGTAGTAGTAGTAGTA CCATATACTACGCAGACTCTGT GAAGGGC (SEQ ID NO: 40) | GATAGGATCACCAGCTGGTACGAGG AGGACTACTATTACTACGGTATGGA CGTC (SEQ ID NO: 41) |
| AA | SYGMN (SEQ ID NO: 42) | YISSSSSTIYYADSVKG (SEQ ID NO: 43) | DRITSWYEEDYYYYGMDV (SEQ ID NO: 44) |

TABLE 2-continued

| | | | |
|---|---|---|---|
| Ab8C10 NA | AGCAACAGTGCTGC TTGGAAC (SEQ ID NO: 45) | AGGACATACTACAGGTCCAAGT GGTATAATGATTATGAAGTATC TGTGAAAAGT (SEQ ID NO: 46) | GAGGAGGGGTATATAGAAGCCCACT CGGTTCCTTACTTTGACTAC (SEQ ID NO: 47) |
| AA | SNSAAWN (SEQ ID NO: 48) | RTYYRSKWYNDYEVSVKS (SEQ ID NO: 49) | EEGYIEAHSVPYFDY (SEQ ID NO: 50) |
| Ab9F7 NA | AACTATGCCATGAG C (SEQ ID NO: 51) | GCTGTTAGTGGTAGTGGTGGTA GCACATTCTACGCAGACTCCAT GAAGGGC (SEQ ID NO: 52) | GAGGGGCTGGAGATTCTGTACTACT TTGACTAC (SEQ ID NO: 53) |
| AA | NYAMS (SEQ ID NO: 54) | AVSGSGGSTFYADSMKG (SEQ ID NO: 55) | EGLEILYYFDY (SEQ ID NO: 56) |
| Ab11D12 NA | GGTTACTACTGGAG C (SEQ ID NO: 57) | GAAATCAATCATAGTGGAAGCA CCAACTACAACCCGTCCCTCAA GAGT (SEQ ID NO: 58) | GCAAAGTTCTATGGTTGGGGGAATT ATCCGTTTGACTCC (SEQ ID NO: 59) |
| AA | GYYWS (SEQ ID NO: 60) | EINHSGSTNYNPSLKS (SEQ ID NO: 61) | AKFYGWGNYPFDS (SEQ ID NO: 62) |

Table 3 below also provides the polynucleotide (DNA) sequences encoding the amino acid sequences of the variable light and variable heavy domains for exemplary anti-human erythropoietin antibodies.

TABLE 3

Anti-Erythropoietin Antibody Variable Region Amino Acid Sequences

Light Chain Variable Region Amino acid sequences

Ab8C10 LC
CSYVLTQPPSVSVAPGQTARITCGGNNIG
SKSVHWYQQKPGQAPVLVVYDDSDRPSGIPERFSGSNSGNTATLTISWVE
AGDEADYYCQVWDSSGDHPVFGGGTKLTVL (SEQ ID NO: 63)

Ab8C10 LC, native leader IgG4
TSYVLTQPPSVSVAPGQTARITCGGNNIGSKS
VHWYQQKPGQAPVLVVYDDSDRPSGIPERFSGSNSGNTATLTISWVEAGD
EADYYCQVWDSSGDHPVFGGGTKLTVL (SEQ ID NO: 64)

Ab9F7 LC
EIVMTQSPATLSVSPGERATLSCRASQR
GNNNLAWYQQKPGQAPRLLIYGASTRATGIPARFSGSGSGTEFTLTISSL
QSEDFAVYYCQQYNIWPRSFGQGTKLEIKR (SEQ ID NO: 65)

Ab11D12 LC
QPVLTQPPSASASLGASVTLTCTLSSGY
SNYKVDWYQQRPGKGPRFVMRVGTGGIVGSKGDGIPDRFSVLGSGLNRYL
TIKNIQEEDESDYHCGADHGSGSNFVWVFGGGTKLTVL (SEQ ID NO: 66)

Ab3A4 LC
CDIQMTQSPSSLSASVGDRVTITCQASQD
ISNFLNWYQQKPGKAPKLLIYDASNLETGVPSRFSGSGSGTDFTFTISSL
QPEDVATYYCQQYDNFPLTFGGGTKVEIKR (SEQ ID NO: 67)

Ab3F5 LC
CDIQMTQSPSSLSASVGDRVTITCQASQD
ISNYLNWFQQKPGKAPNLLIYDASNLETGVPSRFSGGGSGTDFTFTISSL
QPEDIATYYCQQYDDLPLTFGGGTKVEIKR (SEQ ID NO: 68)

Heavy Chain Variable Region Amino acid Sequences

Ab8C10 HC
CQVQLQQSGPGLVKPSQTLSLTCAISGDS
VSSSNSAAWNWIRQSPSRGLEWLGRTYYRSKWYNDYEVSVKSRIIINPDTS
KNQFSLQLNSVTPEDTAVYYCAREEGYIEAHSVPYFDYWGQGTLVTVSS
(SEQ ID NO: 69)

Ab8C10 HC, native leader IgG4
SQVQLQQSGPGLVKPSQTLSLTCAISGDSVS
SNSAAWNWIRQSPSRGLEWLGRTYYRSKWYNDYEVSVKSRIIINPDTSKN
QFSLQLNSVTPEDTAVYYCAREEGYIEAHSVPYFDYWGQGTLVTVSS
(SEQ ID NO: 70)

TABLE 3-continued

Anti-Erythropoietin Antibody Variable Region Amino Acid Sequences

Ab9F7 HC IgG2
EVQLLESGGGLVQPGGSLRLSCAASGFT
FSNYAMSWVRQAPGKGLEWVSAVSGSGGSTFYADSMKGRFTISRDNSKNT
LYLQMNSLRAEDTAVYFCAKEGLEILYYFDYWGQGTLVTVSS (SEQ ID NO: 71)

Ab9F7 HC IgM
EVQLLESGGGLVQPGGSLRLSCAASGFT
FSNYAMSWVRQAPGKGLEWVSAVSGSGGSTFYADSMKGRFTISRDNSKNT
LYLQMNSLRAEDTAVYFCAKEGLEILYYFDYWGQGTLVTVSS (SEQ ID NO: 72)

Ab11D12 HC IgG2
QVQLQQWGAGLLKPSETLSLTCAVYGGS
FSGYYWSWIRQFPGKGLEWIGEINHSGSTNYNPSLKSRVTISVDTSKNQF
SLKLSSVTAADTAVYYCARAKFYGWGNYPFDSWGQGTLVTVSS (SEQ ID NO: 73)

Ab11D12 HC IgM
QVQLQQWGAGLLKPSETLSLTCAVYGGSFSGYYWSWIRQPPGKGLEWIGE
INHSGSTNYNPSLKSRVTISVDTSKNQFSLKLSSVTAADTAVYYCARAKF
YGWGNYPFDSWGQGTLVTVSS (SEQ ID NO: 74)

Ab3A4 HC IgG4
CQVQLVQSGAEVKKPGASVKVSCKASGYT
FTTYGINWVRQAPGQGLEWMGWLSAYSGNTNYAQKLQGRVTMTTDTSTST
AYMELRSLRSDDTAVYYCARGVGASFYFDYWGQGTLVTVSS (SEQ ID NO: 75)

Ab3F5 HC IgG1
CEVQLVESGGGLVQPGGSLRLSCAASGFT
FSSYGMNWVRQAPGKGLEWVSYISSSSSTIYYADSVKGRFTISRDNAKNS
LYLQMNSLRDEDTAVYYCARDRITSWYEEDYYYYGMDVWGQGTTVTVSS
(SEQ ID NO: 76)

Particular embodiments of antibodies of the present invention comprise one or more amino acid sequences that are identical to the amino acid sequences of one or more of the CDRs and/or FRs (framework regions) illustrated above. In one embodiment, the antibody comprises a light chain CDR1 sequence illustrated above. In another embodiment, the antibody comprises a light chain CDR2 sequence illustrated above. In another embodiment, the antibody comprises a light chain CDR3 sequence illustrated in above. In another embodiment, the antibody comprises a heavy chain CDR1 sequence illustrated in above. In another embodiment, the antibody comprises a heavy chain CDR2 sequence illustrated above. In another embodiment, the antibody comprises a heavy chain CDR3 sequence illustrated above. In another embodiment, the antibody comprises a light chain FR1 sequence illustrated above. In another embodiment, the antibody comprises a light chain FR2 sequence illustrated above. In another embodiment, the antibody comprises a light chain FR3 sequence illustrated above. In another embodiment, the antibody comprises a light chain FR4 sequence illustrated above. In another embodiment, the antibody comprises a heavy chain FR1 sequence illustrated above. In another embodiment, the antibody comprises a heavy chain FR2 sequence illustrated above. In another embodiment, the antibody comprises a heavy chain FR3 sequence illustrated above. In another embodiment, the antibody comprises a heavy chain FR4 sequence illustrated above.

In another embodiment, at least one of the antibody's CDR3 sequences differs by no more than 6, 5, 4, 3, 2, 1 or 0 single amino acid addition, substitution, and/or deletion from a CDR3 sequence from the sequences as shown in Tables 2 and 3 above. In another embodiment, the antibody's light chain CDR3 sequence differs by no more than 6, 5, 4, 3, 2, 1 or 0 single amino acid addition, substitution, and/or deletion from a light chain CDR3 sequence from the sequences as shown above and the antibody's heavy chain CDR3 sequence differs by no more than 6, 5, 4, 3, 2, 1 or 0 single amino acid addition, substitution, and/or deletion from a heavy chain CDR3 sequence from the sequences as shown above. In another embodiment, the antibody further comprises 1, 2, 3, 4, or 5 CDR sequences that each independently differs by 6, 5, 4, 3, 2, 1, or 0 single amino acid additions, substitutions, and/or deletions from a CDR sequence of the sequences shown above. In another embodiment, the antibody comprises the CDRs of the light chain variable region and the CDRs of the heavy chain variable region set forth above. In a further embodiment, the antibody comprises the CDRs of any one of the antibodies listed above. In one embodiment, the antibody is a human antibody. In another embodiment, the antibody is a humanized antibody.

In one embodiment, the antibody (or antibody fragment) comprises a light chain variable domain comprising a sequence of amino acids that differs from the sequence of a light chain variable domain listed above only at 15, 14, 13, 12, 11, 10, 9, 8, 7, 6, 5, 4, 3, 2, 1 or 0 residues, wherein each such sequence difference is independently either a deletion, insertion, or substitution of one amino acid residue. In another embodiment, the light-chain variable domain comprises a sequence of amino acids that is at least 70%, 75%, 80%, 85%, 90%, 95%, 97%, or 99% identical to the sequence of a light chain variable domain listed above. In another embodiment, the light chain variable domain comprises a sequence of amino acids that is encoded by a nucleotide sequence that is at least 70%, 75%, 80%, 85%, 90%, 95%, 97%, or 99% identical to the polynucleotide sequence listed above. In another embodiment, the light chain variable domain comprises a sequence of amino acids that is encoded by a polynucleotide that hybridizes under moderately stringent conditions to the complement of a polynucleotide that encodes a light chain variable domain selected from the sequences listed above. In another embodiment, the light chain variable domain comprises a sequence of amino acids that is encoded by a polynucleotide that hybridizes under stringent conditions to the complement of a polynucleotide that encodes a light chain variable domain selected from the group consisting of the sequences listed above.

In another embodiment, the present invention provides an antibody comprising a heavy chain variable domain comprising a sequence of amino acids that differs from the sequence of a heavy chain variable domain selected from the sequences listed above only at 15, 14, 13, 12, 11, 10, 9, 8, 7, 6, 5, 4, 3, 2, 1 or 0 residue(s), wherein each such sequence difference is independently either a deletion, insertion, or substitution of one amino acid residue. In another embodiment, the heavy chain variable domain comprises a sequence of amino acids that is at least 70%, 75%, 80%, 85%, 90%, 95%, 97%, or 99% identical to the sequence of a heavy chain variable domain selected from the sequences listed above. In another embodiment, the heavy chain variable domain comprises a sequence of amino acids that is encoded by a nucleotide sequence that is at least 70%, 75%, 80%, 85%, 90%, 95%, 97%, or 99% identical to a nucleotide sequence that encodes a heavy chain variable domain selected from the sequences listed above. In another embodiment, the heavy chain variable domain comprises a sequence of amino acids that is encoded by a polynucleotide that hybridizes under moderately stringent conditions to the complement of a polynucleotide that encodes a heavy chain variable domain selected from the sequences listed above. In another embodiment, the heavy chain variable domain comprises a sequence of amino acids that is encoded by a polynucleotide that hybridizes under stringent conditions to the complement of a polynucleotide that encodes a heavy chain variable domain selected from the sequences listed above.

Antibodies of the invention can comprise any constant region known in the art. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant regions, e.g., a human alpha-, delta-, epsilon-, gamma-, or mu-type heavy chain constant region. In one embodiment, the light or heavy chain constant region is a fragment, derivative, variant, or mutein of a naturally occurring constant region.

Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype. See also Lanitto et al., Methods Mol. Biol. 178:303-16 (2002).

In one embodiment, an antibody of the invention further comprises the constant light chain kappa or lambda domains or a fragment of these. Sequences of the light chain constant regions and polynucleotides encoding them well known in the art. In another embodiment, an antibody of the invention further comprises a heavy chain constant domain, or a fragment thereof, such as the IgG1 or IgG2 heavy chain constant region, such sequences are well known in the art.

The antibodies of the present invention include those having a desired isotype (for example, IgA, IgG1, IgG2, IgG3, IgG4, IgM, IgE, and IgD) as well as Fab or F(ab')$_2$ fragments thereof. Moreover, if an IgG4 is desired, it may also be desired to introduce a point mutation in the hinge region as described in Bloom et al., 1997, Protein Science 6:407, (incorporated by reference herein) to alleviate a tendency to form intra-H chain disulfide bonds that can lead to heterogeneity in the IgG4 antibodies.

The term "antibody" refers to an intact antibody, or an antigen binding fragment thereof, as described extensively in the Definitions section. An antibody may comprise a complete antibody molecule (including polyclonal, monoclonal, chimeric, humanized, or human versions having full length heavy and/or light chains), or comprise an antigen binding fragment thereof. Antibody fragments include F(ab')$_2$, Fab, Fab', Fv, Fc, and Fd fragments, and can be incorporated into single domain antibodies, single-chain antibodies, maxibodies, minibodies, intrabodies, diabodies, triabodies, tetrabodies, v-NAR and bis-scFv (see e.g., Hollinger and Hudson, 2005, Nature Biotechnology, 23, 9, 1126-1136). Also included are antibody polypeptides such as those disclosed in U.S. Pat. No. 6,703,199, including fibronectin polypeptide monobodies. Other antibody polypeptides are disclosed in U.S. Patent Publication 2005/0238646, which are single-chain polypeptides. In one embodiment, the antibodies of the present invention comprise at least one CDR set forth in Table 2 above. In another aspect, the present invention provides hybridomas capable of producing the antibodies of the invention, and methods of producing antibodies from hybridomas, as described further below.

Chimeric antibodies and humanized antibodies are defined in the definition section and may be prepared by known techniques. In one embodiment, a humanized monoclonal antibody comprises the variable domain of a murine antibody (or all or part of the antigen binding site thereof) and a constant domain derived from a human antibody. Alternatively, a humanized antibody fragment may comprise the antigen binding site of a murine monoclonal antibody and a variable domain fragment (lacking the antigen-binding site) derived from a human antibody. Procedures for the production of engineered monoclonal antibodies include those described in Riechmann et al., 1988, Nature 332:323, Liu et al., 1987, Proc. Nat. Acad. Sci. USA 84:3439, Larrick et al., 1989, Bio/Technology 7:934, and Winter et al., 1993, TIPS 14:139. In one embodiment, the chimeric antibody is a CDR grafted antibody. Techniques for humanizing antibodies are discussed in, e.g., U.S. Pat. Nos. 5,869,619; 5,225,539; 5,821,337; 5,859,205; 6,881,557, Padlan et al., 1995, FASEB J. 9:133-39, Tamura et al., 2000, J. Immunol. 164:1432-41, Zhang, W., et al., Molecular Immunology. 42(12):1445-1451, 2005; Hwang W. et al., Methods. 36(1): 35-42, 2005; Dall'Acqua W F, et al., Methods 36(1):43-60, 2005; and Clark, M., Immunology Today. 21(8):397-402, 2000.

An antibody of the present invention may also be a fully human monoclonal antibody. Fully human monoclonal antibodies may be generated by any number of techniques with which those having ordinary skill in the art will be familiar. Such methods include, but are not limited to, Epstein Barr Virus (EBV) transformation of human peripheral blood cells (e.g., containing B lymphocytes), in vitro immunization of human B-cells, fusion of spleen cells from immunized transgenic mice carrying inserted human immunoglobulin genes, isolation from human immunoglobulin V region phage libraries, or other procedures as known in the art and based on the disclosure herein.

Procedures have been developed for generating human monoclonal antibodies in non-human animals. For example, mice in which one or more endogenous immunoglobulin genes have been inactivated by various means have been prepared. Human immunoglobulin genes have been introduced into the mice to replace the inactivated mouse genes. In this technique, elements of the human heavy and light chain locus are introduced into strains of mice derived from embryonic stem cell lines that contain targeted disruptions of the endogenous heavy chain and light chain loci (see also Bruggemann et al., Curr. Opin. Biotechnol. 8:455-58 (1997)). For example, human immunoglobulin transgenes may be mini-gene constructs, or transloci on yeast artificial chromosomes, which undergo B-cell-specific DNA rearrangement and hypermutation in the mouse lymphoid tissue. Antibodies produced in the animal incorporate human immunoglobulin polypeptide chains encoded by the human genetic material introduced into the animal. In one embodiment, a non-human animal, such as a transgenic mouse, is immunized with a suitable human erythropoietin immunogen.

Examples of techniques for production and use of transgenic animals for the production of human or partially human antibodies are described in U.S. Pat. Nos. 5,814,318, 5,569,825, and 5,545,806, Davis et al., Production of human antibodies from transgenic mice in Lo, ed. Antibody Engineering: Methods and Protocols, Humana Press, NJ:191-200 (2003), Kellermann et al., 2002, Curr Opin Biotechnol. 13:593-97, Russel et al., 2000, Infect Immun 68:1820-26, Gallo et al., 2000, Eur J Immun 30:534-40, Davis et al., 1999, Cancer Metastasis Rev. 18:421-25, Green, 1999, J Immunol Methods. 231:11-23, Jakobovits, 1998, Advanced Drug Delivery Reviews 31:33-42, Green et al., 1998, J Exp Med. 188:483-95, Jakobovits A, 1998, Exp. Opin. Invest. Drugs. 7:607-14, Tsuda et al., 1997, Genomics. 42:413-21, Mendez et al., 1997, Nat Genet. 15:146-56, Jakobovits, 1994, Curr Biol. 4:761-63, Arbones et al., 1994, Immunity. 1:247-60, Green et al., 1994, Nat Genet. 7:13-21, Jakobovits et al., 1993, Nature. 362:255-58, Jakobovits et al., 1993, Proc Natl Acad Sci USA. 90:2551-55. Chen, J., M. Trounstine, F. W. Alt, F. Young, C. Kurahara, J. Loring, D. Huszar "Immunoglobulin gene rearrangement in B-cell deficient mice generated by targeted deletion of the JH locus." International Immunology 5 (1993): 647-656, Choi et al., 1993, Nature Genetics 4: 117-23, Fishwild et al., 1996, Nature Biotechnology 14: 845-51, Harding et al., 1995, Annals of the New York Academy of Sciences, Lonberg et al., 1994, Nature 368: 856-59, Lonberg, 1994, Transgenic Approaches to Human Monoclonal Antibodies in Handbook of Experimental Pharmacology 113: 49-101, Lonberg et al., 1995, Internal Review of Immunology 13: 65-93, Neuberger, 1996, Nature Biotechnology 14: 826, Taylor et al., 1992, Nucleic Acids Research 20: 6287-95, Taylor et al., 1994, International Immunology 6: 579-91, Tomizuka et al., 1997, Nature Genetics 16: 133-43, Tomizuka et al., 2000, Proceedings of the National Academy of Sciences USA 97: 722-27, Tuaillon et al., 1993, Proceedings of the National Academy of Sciences USA 90: 3720-24, and Tuaillon et al., 1994, Journal of Immunology 152: 2912-20.; Lonberg et al., Nature 368:856, 1994; Taylor et al., Int. Immun 6579, 1994; U.S. Pat. No. 5,877,397; Bruggemann et al., 1997 Curr. Opin. Biotechnol. 8:455-58; Jakobovits et al., 1995 Ann. N. Y. Acad. Sci. 764:525-35. In addition, protocols involving the XenoMouse® (Abgenix, now Amgen, Inc.) are described, for example in U.S. Ser. No. 05/0118643 and WO 05/694879, WO 98/24838, WO 00/76310, and U.S. Pat. No. 7,064,244.

Lymphoid cells from the immunized transgenic mice are fused with myeloma cells for example to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in such fusions include Sp-20, P3-X63/Ag8, P3-X63-Ag8.653, NS1/1.Ag 4 1, Sp210-Ag14, FO, NSO/U, MPC-11, MPC11-X45-GTG 1.7 and S194/5XX0 Bul; examples of cell lines used in rat fusions include R210.RCY3, Y3-Ag 1.2.3, IR983F and 4B210. Other cell lines useful for cell fusions are U-266, GM1500-GRG2, LICR-LON-HMy2 and UC729-6.

The lymphoid (e.g., spleen) cells and the myeloma cells may be combined for a few minutes with a membrane fusion-promoting agent, such as polyethylene glycol or a nonionic detergent, and then plated at low density on a selective medium that supports the growth of hybridoma cells but not unfused myeloma cells. One selection media is HAT (hypoxanthine, aminopterin, thymidine). After a sufficient time, usually about one to two weeks, colonies of cells are observed. Single colonies are isolated, and antibodies produced by the cells may be tested for binding activity to human erythropoietin using any one of a variety of immunoassays known in the art and described herein. The hybridomas are cloned (e.g., by limited dilution cloning or by soft agar plaque isolation) and positive clones that produce an antibody specific to human erythropoietin are selected and cultured. The monoclonal antibodies from the hybridoma cultures may be isolated from the supernatants of hybridoma cultures. Thus the present invention provides hybridomas that comprise polynucleotides encoding the antibodies of the invention in the chromosomes of the cell. These hybridomas can be cultured according to methods described herein and known in the art.

Another method for generating human antibodies of the invention includes immortalizing human peripheral blood cells by EBV transformation. See, e.g., U.S. Pat. No. 4,464, 456. Such an immortalized B-cell line (or lymphoblastoid cell line) producing a monoclonal antibody that specifically binds to human erythropoietin can be identified by immunodetection methods as provided herein, for example, an ELISA, and then isolated by standard cloning techniques. The stability of the lymphoblastoid cell line producing an anti-human erythropoietin antibody may be improved by fusing the transformed cell line with a murine myeloma to produce a mouse-human hybrid cell line according to methods known in the art (see, e.g., Glasky et al., Hybridoma 8:377-89 (1989)). Still another method to generate human monoclonal antibodies is in vitro immunization, which includes priming human splenic B-cells with human erythropoietin, followed by fusion of primed B-cells with a heterohybrid fusion partner. See, e.g., Boerner et al., 1991 J. Immunol. 147:86-95.

In certain embodiments, a B-cell that is producing an anti-human erythropoietin antibody is selected and the light chain and heavy chain variable regions are cloned from the B-cell according to molecular biology techniques known in the art (WO 92/02551; U.S. Pat. No. 5,627,052; Babcook et al., Proc. Natl. Acad. Sci. USA 93:7843-48 (1996)) and described herein. B-cells from an immunized animal may be isolated from the spleen, lymph node, or peripheral blood sample by selecting a cell that is producing an antibody that specifically binds to human erythropoietin. B-cells may also be isolated from humans, for example, from a peripheral blood sample. Methods for detecting single B-cells that are producing an antibody with the desired specificity are well known in the art, for example, by plaque formation, fluorescence-activated cell sorting, in vitro stimulation followed by detection of specific antibody, and the like. Methods for selection of specific antibody-producing B-cells include, for example, preparing a single cell suspension of B-cells in soft agar that contains human erythropoietin. Binding of the specific antibody produced by the B-cell to the antigen results in the formation of a complex, which may be visible as an immunoprecipitate. After the B-cells producing the desired antibody are selected, the specific antibody genes may be cloned by isolating and amplifying DNA or mRNA according to methods known in the art and described herein.

An additional method for obtaining antibodies of the invention is by phage display. See, e.g., Winter et al., 1994 Annu. Rev. Immunol. 12:433-55; Burton et al., 1994 Adv. Immunol. 57:191-280. Human or murine immunoglobulin variable region gene combinatorial libraries may be created in phage vectors that can be screened to select Ig fragments (Fab, Fv, sFv, or multimers thereof) that bind specifically to TGF-beta binding protein or variant or fragment thereof. See, e.g., U.S. Pat. No. 5,223,409; Huse et al., 1989 Science 246:1275-81; Sastry et al., Proc. Natl. Acad. Sci. USA 86:5728-32 (1989); Alting-Mees et al., Strategies in Molecular Biology 3:1-9 (1990); Kang et al., 1991 Proc. Natl. Acad. Sci. USA 88:4363-66; Hoogenboom et al., 1992 J. Molec. Biol. 227:381-388; Schlebusch et al., 1997 Hybridoma 16:47-52 and references cited therein. For example, a library containing a plurality of polynucleotide sequences encoding Ig variable region fragments may be inserted into the genome of a filamentous bacteriophage, such as M 13 or a variant thereof, in frame with the sequence encoding a phage coat protein. A fusion protein may be a fusion of the coat protein with the light chain variable region domain and/or with the heavy chain variable region domain. According to certain embodiments, immunoglobulin Fab fragments may also be displayed on a phage particle (see, e.g., U.S. Pat. No. 5,698,426).

Heavy and light chain immunoglobulin cDNA expression libraries may also be prepared in lambda phage, for example, using λImmunoZap™ (H) and λImmunoZap™ (L) vectors (Stratagene, La Jolla, Calif.). Briefly, mRNA is isolated from a B-cell population, and used to create heavy and light chain immunoglobulin cDNA expression libraries in the λImmunoZap(H) and λImmunoZap(L) vectors. These vectors may be screened individually or co-expressed to form Fab fragments or antibodies (see Huse et al., supra; see also Sastry et al., supra). Positive plaques may subsequently be converted to a non-lytic plasmid that allows high level expression of monoclonal antibody fragments from E. coli.

In one embodiment, in a hybridoma the variable regions of a gene expressing a monoclonal antibody of interest are amplified using nucleotide primers. These primers may be synthesized by one of ordinary skill in the art, or may be purchased from commercially available sources. (See, e.g., Stratagene (La Jolla, Calif.), which sells primers for mouse and human variable regions including, among others, primers for $V_{Ha}$, $V_{Hb}$, $V_{Hc}$, $V_{Hd}$, $C_{H1}$, $V_L$ and $C_L$ regions.) These primers may be used to amplify heavy or light chain variable regions, which may then be inserted into vectors such as ImmunoZAP™ H or ImmunoZAP™ L (Stratagene), respectively. These vectors may then be introduced into E. coli, yeast, or mammalian-based systems for expression. Large amounts of a single-chain protein containing a fusion of the $V_H$ and $V_L$ domains may be produced using these methods (see Bird et al., Science 242:423-426, 1988).

Once cells producing antibodies according to the invention have been obtained using any of the above-described immunization and other techniques, the specific antibody genes may be cloned by isolating and amplifying DNA or mRNA therefrom according to standard procedures as described herein. The antibodies produced therefrom may be sequenced and the CDRs identified and the DNA coding for the CDRs may be manipulated as described previously to generate other antibodies according to the invention.

In certain embodiments, antibodies are generated by first identifying antibodies that bind to cells expressing human erythropoietin and/or compete for binding with the antibodies described in this application.

It will be understood by one skilled in the art that some proteins, such as antibodies, may undergo a variety of posttranslational modifications. The type and extent of these modifications often depends on the host cell line used to express the protein as well as the culture conditions. Such modifications may include variations in glycosylation, methionine oxidation, diketopiperizine formation, aspartate isomerization and asparagine deamidation. A frequent modification is the loss of a carboxy-terminal basic residue (such as lysine or arginine) due to the action of carboxypeptidases (as described in Harris, R. J. Journal of Chromatography 705:129-134, 1995).

An alternative method for production of a murine monoclonal antibody is to inject the hybridoma cells into the peritoneal cavity of a syngeneic mouse, for example, a mouse that has been treated (e.g., pristane-primed) to promote formation of ascites fluid containing the monoclonal antibody. Monoclonal antibodies can be isolated and purified by a variety of well-established techniques. Such isolation techniques include affinity chromatography with Protein-A Sepharose, size-exclusion chromatography, and ion-exchange chromatography (see, for example, Coligan at pages 2.7.1-2.7.12 and pages 2.9.1-2.9.3; Baines et al., "Purification of Immunoglobulin G (IgG)," in Methods in Molecular Biology, Vol. 10, pages 79-104 (The Humana Press, Inc. 1992)). Monoclonal antibodies may be purified by affinity chromatography using an appropriate ligand selected based on particular properties of the antibody (e.g., heavy or light chain isotype, binding specificity, etc.). Examples of a suitable ligand, immobilized on a solid support, include Protein A, Protein G, an anticonstant region (light chain or heavy chain) antibody, an anti-idiotype antibody, and a TGF-beta binding protein, or fragment or variant thereof.

Molecular evolution of the complementarity determining regions (CDRs) in the center of the antibody binding site also has been used to isolate antibodies with increased affinity, for example, antibodies having increased affinity for c-erbB-2, as described by Schier et al., 1996, J. Mol. Biol. 263:551. Accordingly, such techniques are useful in preparing antibodies to human erythropoietin.

Antibodies directed against human erythropoietin can be used, for example, in assays to detect the presence of human erythropoietin, either in vitro or in vivo.

Although human, partially human, or humanized antibodies will be suitable for many applications, particularly those involving administration of the antibody to a human subject, other types of antibodies will be suitable for certain applications. The non-human antibodies of the invention can be, for example, derived from any antibody-producing animal, such as mouse, rat, rabbit, goat, donkey, or non-human primate (for example, monkey such as cynomologus or rhesus monkey) or ape (e.g., chimpanzee)). Non-human antibodies of the invention can be used, for example, in in vitro and cell-culture based applications, or any other application where an immune response to the antibody of the invention does not occur, is insignificant, can be prevented, is not a concern, or is desired. In one embodiment, a non-human antibody of the invention is administered to a non-human subject. In another embodiment, the non-human antibody does not elicit an immune response in the non-human subject. In another embodiment, the non-human antibody is from the same species as the non-human subject, e.g., a mouse antibody of the invention is administered to a mouse. An antibody from a particular species can be made by, for example, immunizing an animal of that species with the desired immunogen or using an artificial system for generating antibodies of that species (e.g., a bacterial or phage display-based system for generating antibodies of a particular species), or by converting an antibody from one species into an antibody from another species by replacing, e.g., the constant region of the antibody with a constant region from the other species, or by replacing one or more amino acid residues of the antibody so that it more closely resembles the sequence of an antibody from the other species. In one embodiment, the antibody is a chimeric antibody comprising amino acid sequences derived from antibodies from two or more different species.

Antibodies also may be prepared by any of a number of conventional techniques. For example, they may be purified from cells that naturally express them (e.g., an antibody can be purified from a hybridoma that produces it), or produced in recombinant expression systems, using any technique known in the art. See, for example, Monoclonal Antibodies, Hybridomas: A New Dimension in Biological Analyses, Kennet et al. (eds.), Plenum Press, New York (1980); and Antibodies: A Laboratory Manual, Harlow and Land (eds.), Cold Spring Harbor Laboratory Press, Cold Spring Harbor, N.Y., (1988). This is discussed in the nucleic acid section below.

Where it is desired to improve the affinity of antibodies according to the invention containing one or more of the above-mentioned CDRs can be obtained by a number of affinity maturation protocols including maintaining the CDRs (Yang et al., J. Mol. Biol., 254, 392-403, 1995), chain shuffling (Marks et al., Bio/Technology, 10, 779-783, 1992), use of mutation strains of E. coli. (Low et al., J. Mol. Biol., 250, 350-368, 1996), DNA shuffling (Patten et al., Curr. Opin. Biotechnol., 8, 724-733, 1997), phage display (Thompson et al., J. Mol. Biol., 256, 7-88, 1996) and additional PCR techniques (Crameri, et al., Nature, 391, 288-291, 1998). All of these methods of affinity maturation are discussed by Vaughan et al. (Nature Biotechnology, 16, 535-539, 1998).

Antibody Fragments

In another aspect, the present invention provides fragments of an anti-human erythropoietin antibody of the invention. Such fragments can consist entirely of antibody-derived sequences or can comprise additional sequences. Examples of antigen-binding fragments include Fab, F(ab')2, single chain antibodies, diabodies, triabodies, tetrabodies, and domain antibodies. Other examples are provided in Lunde et al., 2002, Biochem. Soc. Trans. 30:500-06.

Single chain antibodies may be formed by linking heavy and light chain variable domain (FIT region) fragments via an amino acid bridge (short peptide linker), resulting in a single polypeptide chain Such single-chain Fvs (scFvs) have been prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e g, dimers, trimers, or tetramers), depending on the length of a flexible linker between the two variable domains (Kortt et al., 1997, Prot. Eng. 10:423; Kortt et al., 2001, Biomol. Eng. 18:95-108). By combining different $V_L$ and $V_H$-comprising polypeptides, one can form multimeric scFvs that bind to different epitopes (Kriangkum et al., 2001, Biomol. Eng. 18:31-40). Techniques developed for the production of single chain antibodies include those described in U.S. Pat. No. 4,946,778; Bird, 1988, Science 242:423; Huston et al., 1988, Proc. Natl. Acad. Sci. USA 85:5879; Ward et al., 1989, Nature 334:544, de Graaf et al., 2002, Methods Mol Biol. 178:379-87. Single chain antibodies derived from antibodies provided herein include, but are not limited to, scFvs comprising the variable domain combinations L1H1, L2H2, L3H3, L4H4, L5H5, L6H6, L7H7, L8H8, L9H9, and L10H10 are encompassed by the present invention.

Antigen binding fragments derived from an antibody can also be obtained, for example, by proteolytic hydrolysis of the antibody, for example, pepsin or papain digestion of whole antibodies according to conventional methods. By way of example, antibody fragments can be produced by enzymatic cleavage of antibodies with pepsin to provide a 5S fragment termed $F(ab')_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using papain produces two monovalent Fab fragments and an Fc fragment directly. These methods are described, for example, by Goldenberg, U.S. Pat. No. 4,331,647, Nisonoff et al., Arch. Biochem. Biophys. 89:230, 1960; Porter, Biochem. J. 73:119, 1959; Edelman et al., in Methods in Enzymology 1:422 (Academic Press 1967); and by Andrews, S. M. and Titus, J. A. in Current Protocols in Immunology (Coligan J. E., et al., eds), John Wiley & Sons, New York (2003), pages 2.8.1-2.8.10 and 2.10A.1-2.10A.5. Other methods for cleaving antibodies, such as separating heavy chains to form monovalent light-heavy chain fragments (Fd), further cleaving of fragments, or other enzymatic, chemical, or genetic techniques may also be used, so long as the fragments bind to the antigen that is recognized by the intact antibody.

Another form of an antibody fragment is a peptide comprising one or more complementarity determining regions (CDRs) of an antibody. CDRs can be obtained by constructing polynucleotides that encode the CDR of interest. Such polynucleotides are prepared, for example, by using the polymerase chain reaction to synthesize the variable region using mRNA of antibody-producing cells as a template (see, for example, Larrick et al., Methods: A Companion to Methods in Enzymology 2:106, 1991; Courtenay-Luck, "Genetic Manipulation of Monoclonal Antibodies," in Monoclonal Antibodies: Production, Engineering and Clinical Application, Ritter et al. (eds.), page 166 (Cambridge University Press 1995); and Ward et al., "Genetic Manipulation and Expression of Antibodies," in Monoclonal Antibodies: Principles and Applications, Birch et al., (eds.), page 137 (Wiley-Liss, Inc. 1995)). The antibody fragment further may comprise at least one variable region domain of an antibody described herein. Thus, for example, the V region domain may be monomeric and be a $V_H$ or $V_L$ domain, which is capable of independently binding human erythropoietin with an affinity at least equal to $10^{-7}$M or less as described below.

The variable region domain may be any naturally occurring variable domain or an engineered version thereof. By engineered version is meant a variable region domain that has been created using recombinant DNA engineering techniques. Such engineered versions include those created, for example, from a specific antibody variable region by insertions, deletions, or changes in or to the amino acid sequences of the specific antibody. Particular examples include engineered variable region domains containing at least one CDR and optionally one or more framework amino acids from a first antibody and the remainder of the variable region domain from a second antibody.

The variable region domain may be covalently attached at a C-terminal amino acid to at least one other antibody domain or a fragment thereof. Thus, for example, a VH domain that is present in the variable region domain may be linked to an immunoglobulin CH1 domain, or a fragment thereof. Similarly a $V_L$ domain may be linked to a $C_K$ domain or a fragment thereof. In this way, for example, the antibody may be a Fab fragment wherein the antigen binding domain contains associated $V_H$ and $V_L$ domains covalently linked at their C-termini to a CH1 and $C_K$ domain, respectively. The CH1 domain may be extended with further amino acids, for example to provide a hinge region or a portion of a hinge region domain as found in a Fab' fragment, or to provide further domains, such as antibody CH2 and CH3 domains.

Derivatives and Variants of Antibodies

The nucleotide sequences of the antibodies of the present invention, encoding the corresponding amino acid sequences of the antibodies of the present invention, can be altered, for example, by random mutagenesis or by site-directed mutagenesis (e.g., oligonucleotide-directed site-specific mutagenesis) to create an altered polynucleotide comprising one or more particular nucleotide substitutions, deletions, or insertions as compared to the non-mutated polynucleotide. Examples of techniques for making such alterations are described in Walder et al., 1986, Gene 42:133; Bauer et al. 1985, Gene 37:73; Craik, BioTechniques, January 1985, 12-19; Smith et al., 1981, Genetic Engineering: Principles and Methods, Plenum Press; and U.S. Pat. Nos. 4,518,584 and 4,737,462. These and other methods can be used to make, for example, derivatives of anti-human erythropoietin antibodies that have a desired property, for example, increased affinity, avidity, or specificity for human erythropoietin increased activity or stability in vivo or in vitro, or reduced in vivo side-effects as compared to the underivatized antibody.

Other derivatives of anti-human erythropoietin antibodies within the scope of this invention include covalent or aggregative conjugates of anti-human erythropoietin antibodies, or fragments thereof, with other proteins or polypeptides, such as by expression of recombinant fusion proteins comprising heterologous polypeptides fused to the N-terminus or C-terminus of an anti-human erythropoietin antibody polypeptide. For example, the conjugated peptide may be a heterologous signal (or leader) polypeptide, e.g., the yeast alpha-factor leader, or a peptide such as an epitope tag. Antibody-containing fusion proteins can comprise peptides added to facilitate purification or identification of antibody (e.g., poly-His). An antibody also can be linked to the FLAG peptide as described in Hopp et al., Bio/Technology 6:1204, 1988, and U.S. Pat. No. 5,011,912. The FLAG peptide is highly antigenic and provides an epitope reversibly bound by a specific monoclonal antibody (mAb), enabling rapid assay and facile purification of expressed recombinant protein. Reagents useful for preparing fusion proteins in which the FLAG peptide is fused to a given polypeptide are commercially available (Sigma, St. Louis, Mo.).

In another embodiment, oligomers that contain one or more antibodies may be employed as human erythropoietin antagonists. Oligomers may be in the form of covalently-linked or non-covalently-linked dimers, trimers, or higher oligomers. Oligomers comprising two or more antibody are contemplated for use, with one example being a homodimer Other oligomers include heterodimers, homotrimers, heterotrimers, homotetramers, heterotetramers, etc.

One embodiment is directed to oligomers comprising multiple antibodies joined via covalent or non-covalent interactions between peptide moieties fused to the antibodies. Such peptides may be peptide linkers (spacers), or peptides that have the property of promoting oligomerization. Leucine zippers and certain polypeptides derived from antibodies are among the peptides that can promote oligomerization of antibodies attached thereto, as described in more detail below.

In particular embodiments, the oligomers comprise from two to four antibodies. The antibodies of the oligomer may be in any form, such as any of the forms described above, e.g., variants or fragments. Preferably, the oligomers comprise antibodies that have human erythropoietin binding activity.

In one embodiment, an oligomer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al., 1991, PNAS USA 88:10535; Byrn et al., 1990, Nature 344:677; and Hollenbaugh et al., 1992 "Construction of Immunoglobulin Fusion Proteins", in Current Protocols in Immunology, Suppl. 4, pages 10.19.1-10.19.11. One embodiment of the present invention is directed to a dimer comprising two fusion proteins created by fusing a human erythropoietin binding fragment of an anti-human erythropoietin antibody to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

The term "Fc polypeptide" as used herein includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

One suitable Fc polypeptide, described in PCT application WO 93/10151 (hereby incorporated by reference), is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in Baum et al., 1994, EMBO J. 13:3992-4001. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors. In other embodiments, the variable portion of the heavy and/or light chains of an anti-human erythropoietin antibody may be substituted for the variable portion of an antibody heavy and/or light chain.

Alternatively, the oligomer is a fusion protein comprising multiple antibodies, with or without peptide linkers (spacer peptides). Among the suitable peptide linkers are those described in U.S. Pat. Nos. 4,751,180 and 4,935,233.

Another method for preparing oligomeric antibodies involves use of a leucine zipper. Leucine zipper domains are peptides that promote oligomerization of the proteins in which they are found. Leucine zippers were originally identified in several DNA-binding proteins (Landschulz et al., 1988, Science 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in PCT application WO 94/10308, and the leucine zipper derived from lung surfactant protein D (SPD) described in Hoppe et al., 1994, FEBS Letters 344:191, hereby incorporated by reference. The use of a modified leucine zipper that allows for stable trimerization of a heterologous protein fused thereto is described in Fanslow et al., 1994, Semin. Immunol. 6:267-78. In one approach, recombinant fusion proteins comprising an anti-human erythropoietin antibody fragment or derivative fused to a leucine zipper peptide are expressed in suitable host cells, and the soluble oligomeric anti-human erythropoietin antibody fragments or derivatives that form are recovered from the culture supernatant.

In another embodiment, the antibody derivatives can comprise at least one of the CDRs disclosed herein. For example, one or more CDR may be incorporated into known antibody framework regions (IgG1, IgG2, etc.), or conjugated to a suitable vehicle to enhance the half-life thereof. Suitable vehicles include, but are not limited to Fc, albumin, transferrin, and the like. These and other suitable vehicles are known in the art. Such conjugated CDR peptides may be in monomeric, dimeric, tetrameric, or other form. In one embodiment, one or more water-soluble polymer is bonded at one or more specific position, for example at the amino terminus, of a binding agent. In an example, an antibody derivative comprises one or more water soluble polymer attachments, including, but not limited to, polyethylene glycol, polyoxyethylene glycol, or polypropylene glycol. See, e.g., U.S. Pat. Nos. 4,640,835, 4,496,689, 4,301,144, 4,670,417, 4,791,192 and 4,179,337. In certain embodiments, a derivative comprises one or more of monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of such polymers. In certain embodiments, one or more water-soluble polymer is randomly attached to one or more side chains. In certain embodiments, PEG can act to improve the therapeutic capacity for a binding agent, such as an antibody. Certain such methods are discussed, for example, in U.S. Pat. No. 6,133,426, which is hereby incorporated by reference for any purpose.

It will be appreciated that an antibody of the present invention may have at least one amino acid substitution, providing that the antibody retains binding specificity. Therefore, modifications to the antibody structures are encompassed within the scope of the invention. These may include amino acid substitutions, which may be conservative or non-conservative, that do not destroy the human erythropoietin binding capability of an antibody. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties. A conservative amino acid substitution may also involve a substitution of a native amino acid residue with a normative residue such that there is little or no effect on the polarity or charge of the amino acid residue at that position.

Non-conservative substitutions may involve the exchange of a member of one class of amino acids or amino acid mimetics for a member from another class with different physical properties (e.g. size, polarity, hydrophobicity, charge). Such substituted residues may be introduced into regions of the human antibody that are homologous with non-human antibodies, or into the non-homologous regions of the molecule.

Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change may be avoided. In other words, based on information gathered from such routine experiments, one skilled in the art can readily determine the amino acids where further substitutions should be avoided either alone or in combination with other mutations.

A skilled artisan will be able to determine suitable variants of the polypeptide as set forth herein using well-known techniques. In certain embodiments, one skilled in the art may identify suitable areas of the molecule that may be changed without destroying activity by targeting regions not believed to be important for activity. In certain embodiments, one can identify residues and portions of the molecules that are conserved among similar polypeptides. In certain embodiments, even areas that may be important for biological activity or for structure may be subject to conservative amino acid substitutions without destroying the biological activity or without adversely affecting the polypeptide structure. Additionally, one skilled in the art can review structure-function studies identifying residues in similar polypeptides that are important for activity or structure. In view of such a comparison, one can predict the importance of amino acid residues in a protein that correspond to amino acid residues which are important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of an antibody with respect to its three dimensional structure. In certain embodiments, one skilled in the art may choose not to make radical changes to amino acid residues predicted to be on the surface of the protein, since such residues may be involved in important interactions with other molecules. A number of scientific publications have been devoted to the prediction of secondary structure. See Moult J., Curr. Op. in Biotech., 7(4):422-427 (1996), Chou et al., Biochemistry, 13(2):222-245 (1974); Chou et al., Biochemistry, 113(2):211-222 (1974); Chou et al., Adv. Enzymol. Relat. Areas Mol. Biol., 47:45-148 (1978); Chou et al., Ann. Rev. Biochem., 47:251-276 and Chou et al., Biophys. J., 26:367-384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See Holm et al., Nucl. Acid. Res., 27(1):244-247 (1999). It has been suggested (Brenner et al., Curr. Op. Struct. Biol., 7(3):369-376 (1997)) that there are a limited number of folds in a given polypeptide or protein and that once a critical number of structures have been resolved, structural prediction will become dramatically more accurate.

Additional methods of predicting secondary structure include "threading" (Jones, D., Curr. Opin. Struct. Biol., 7(3):377-87 (1997); Sippl et al., Structure, 4(1):15-19 (1996)), "profile analysis" (Bowie et al., Science, 253:164-170 (1991); Gribskov et al., Meth. Enzym., 183:146-159 (1990); Gribskov et al., Proc. Nat. Acad. Sci., 84(13):4355-4358 (1987)), and "evolutionary linkage" (See Holm, supra (1999), and Brenner, supra (1997)).

In certain embodiments, variants of antibodies include glycosylation variants wherein the number and/or type of glycosylation site has been altered compared to the amino acid sequences of a parent polypeptide. In certain embodiments, variants comprise a greater or a lesser number of N-linked glycosylation sites than the native protein. Alternatively, substitutions which eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional antibody variants include cysteine variants wherein one or more cysteine residues are deleted from or substituted for another amino acid (e.g., serine) as compared to the parent amino acid sequence. Cysteine variants may be useful when antibodies must be refolded into a biologically active conformation such as after the isolation of insoluble inclusion bodies. Cysteine variants generally have fewer cysteine residues than the native protein, and typically have an even number to minimize interactions resulting from unpaired cysteines.

Desired amino acid substitutions (whether conservative or non-conservative) can be determined by those skilled in the art at the time such substitutions are desired. In certain embodiments, amino acid substitutions can be used to identify important residues of antibodies to human erythropoietin, or to increase or decrease the affinity of the antibodies to human erythropoietin described herein.

According to certain embodiments, preferred amino acid substitutions are those which: (1) reduce susceptibility to proteolysis, (2) reduce susceptibility to oxidation, (3) alter binding affinity for forming protein complexes, (4) alter binding affinities, and/or (4) confer or modify other physiochemical or functional properties on such polypeptides. According to certain embodiments, single or multiple amino acid substitutions (in certain embodiments, conservative amino acid substitutions) may be made in the naturally-occurring sequence (in certain embodiments, in the portion of the polypeptide outside the domain(s) forming intermolecular contacts). In certain embodiments, a conservative amino acid substitution typically may not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. Nature 354:105 (1991), which are each incorporated herein by reference.

In certain embodiments, antibodies of the invention may be chemically bonded with polymers, lipids, or other moieties.

The antigen binding agents may comprise at least one of the CDRs described herein incorporated into a biocompatible framework structure. In one example, the biocompatible framework structure comprises a polypeptide or portion thereof that is sufficient to form a conformationally stable structural support, or framework, or scaffold, which is able to display one or more sequences of amino acids that bind to an antigen (e.g., CDRs, a variable region, etc.) in a localized surface region. Such structures can be a naturally occurring polypeptide or polypeptide "fold" (a structural motif), or can have one or more modifications, such as additions, deletions or substitutions of amino acids, relative to a naturally occurring polypeptide or fold. These scaffolds can be derived from a polypeptide of any species (or of more than one species), such as a human, other mammal, other vertebrate, invertebrate, plant, bacteria or virus.

Typically the biocompatible framework structures are based on protein scaffolds or skeletons other than immunoglobulin domains. For example, those based on fibronectin, ankyrin, lipocalin, neocarzinostain, cytochrome b, CP1 zinc finger, PST1, coiled coil, LACI-D1, Z domain and tendamistat domains may be used (See e.g., Nygren and Uhlen, 1997, Current Opinion in Structural Biology, 7, 463-469).

Additionally, one skilled in the art will recognize that suitable binding agents include portions of these antibodies, such as one or more of heavy chain CDR1, CDR2, CDR3, light chain CDR1, CDR2 and CDR3 as specifically disclosed herein. At least one of the regions of heavy chain CDR1, CDR2, CDR3, CDR1, CDR2 and CDR3 may have at least one amino acid substitution, provided that the antibody retains the binding specificity of the non-substituted CDR. The non-CDR portion of the antibody may be a non-protein molecule. The non-CDR portion of the antibody may be composed of amino acids, wherein the antibody is a recombinant binding protein or a synthetic peptide.

Nucleic Acids

In one aspect, the present invention provides isolated nucleic acid molecules that encode the antigen binding agents of the present invention. In addition, provided are vectors comprising the nucleic acids, cell comprising the nucleic acids, and methods of making the antibodies of the invention. The nucleic acids comprise, for example, polynucleotides that encode all or part of an antibody, for example, one or both chains of an antibody of the invention, or a fragment, derivative, mutein, or variant thereof, polynucleotides sufficient for use as hybridization probes, PCR primers or sequencing primers for identifying, analyzing, mutating or amplifying a polynucleotide encoding a polypeptide, anti-sense nucleic acids for inhibiting expression of a polynucleotide, and complementary sequences of the foregoing. The nucleic acids can be any length. They can be, for example, 5, 10, 15, 20, 25, 30, 35, 40, 45, 50, 75, 100, 125, 150, 175, 200, 250, 300, 350, 400, 450, 500, 750, 1,000, 1,500, 3,000, 5,000 or more nucleotides in length, and/or can comprise one or more additional sequences, for example, regulatory sequences, and/or be part of a larger nucleic acid, for example, a vector. The nucleic acids can be single-stranded or double-stranded and can comprise RNA and/or DNA nucleotides, and artificial variants thereof (e.g., peptide nucleic acids).

Nucleic acids encoding antibody polypeptides (e.g., heavy or light chain, variable domain only, or full length) may be isolated from B-cells of mice that have been immunized with human erythropoietin antigen. The nucleic acid may be isolated by conventional procedures such as polymerase chain reaction (PCR).

Nucleic acid sequences encoding the variable regions of the heavy and light chain variable regions are shown above. The skilled artisan will appreciate that, due to the degeneracy of the genetic code, each of the polypeptide sequences disclosed herein is encoded by a large number of other nucleic acid sequences. The present invention provides each degenerate nucleotide sequence encoding each antibody of the invention.

The invention further provides nucleic acids that hybridize to other nucleic acids (e.g., nucleic acids comprising a nucleotide sequence of any of A1-A14) under particular hybridization conditions. Methods for hybridizing nucleic acids are well-known in the art. See, e.g., Current Protocols in Molecular Biology, John Wiley & Sons, N.Y. (1989), 6.3.1-6.3.6. As defined herein, for example, a moderately stringent hybridization condition uses a prewashing solution containing 5× sodium chloride/sodium citrate (SSC), 0.5% SDS, 1.0 mM EDTA (pH 8.0), hybridization buffer of about 50% formamide, 6×SSC, and a hybridization temperature of 55° C. (or other similar hybridization solutions, such as one containing about 50% formamide, with a hybridization temperature of 42° C.), and washing conditions of 60° C., in 0.5×SSC, 0.1% SDS. A stringent hybridization condition hybridizes in 6×SSC at 45° C., followed by one or more washes in 0.1×SSC, 0.2% SDS at 68° C. Furthermore, one of skill in the art can manipulate the hybridization and/or washing conditions to increase or decrease the stringency of hybridization such that nucleic acids comprising nucleotide sequences that are at least 65, 70, 75, 80, 85, 90, 95, 98 or 99% identical to each other typically remain hybridized to each other. The basic parameters affecting the choice of hybridization conditions and guidance for devising suitable conditions are set forth by, for example, Sambrook, Fritsch, and Maniatis (1989, Molecular Cloning: A Laboratory Manual, Cold Spring Harbor Laboratory Press, Cold Spring Harbor, N.Y., chapters 9 and 11; and Current Protocols in Molecular Biology, 1995, Ausubel et al., eds., John Wiley & Sons, Inc., sections 2.10 and 6.3-6.4), and can be readily determined by those having ordinary skill in the art based on, for example, the length and/or base composition of the DNA. Changes can be introduced by mutation into a nucleic acid, thereby leading to changes in the amino acid sequence of a polypeptide (e.g., an antibody) that it encodes. Mutations can be introduced using any technique known in the art. In one embodiment, one or more particular amino acid residues are changed using, for example, a site-directed mutagenesis protocol. In another embodiment, one or more randomly selected residues is changed using, for example, a random mutagenesis protocol. However it is made, a mutant polypeptide can be expressed and screened for a desired property.

Mutations can be introduced into a nucleic acid without significantly altering the biological activity of a polypeptide that it encodes. For example, one can make nucleotide substitutions leading to amino acid substitutions at non-essential amino acid residues. In one embodiment, a nucleotide sequence provided herein for of the antibodies of the present invention, or a desired fragment, variant, or derivative thereof, is mutated such that it encodes an amino acid sequence comprising one or more deletions or substitutions of amino acid residues that are shown herein for the light chains of the antibodies of the present invention or the heavy chains of the antibodies of the present invention to be residues where two or more sequences differ. In another embodiment, the mutagenesis inserts an amino acid adjacent to one or more amino acid residues shown herein for the light chains of the antibodies of the present invention or the heavy chains of the antibodies of the present invention to be residues where two or more sequences differ. Alternatively, one or more mutations can be introduced into a nucleic acid that selectively change the biological activity. (e.g., binding to human erythropoietin) of a polypeptide that it encodes. For example, the mutation can quantitatively or qualitatively change the biological activity. Examples of quantitative changes include increasing, reducing or eliminating the activity. Examples of qualitative changes include changing the antigen specificity of an antibody.

In another aspect, the present invention provides nucleic acid molecules that are suitable for use as primers or hybridization probes for the detection of nucleic acid sequences of the invention. A nucleic acid molecule of the invention can comprise only a portion of a nucleic acid sequence encoding a full-length polypeptide of the invention, for example, a fragment that can be used as a probe or primer or a fragment encoding an active portion (e.g., a human erythropoietin binding portion) of a polypeptide of the invention.

Probes based on the sequence of a nucleic acid of the invention can be used to detect the nucleic acid or similar nucleic acids, for example, transcripts encoding a polypeptide of the invention. The probe can comprise a label group, e.g., a radioisotope, a fluorescent compound, an enzyme, or an enzyme co-factor. Such probes can be used to identify a cell that expresses the polypeptide.

In another aspect, the present invention provides vectors comprising a nucleic acid encoding a polypeptide of the invention or a portion thereof. Examples of vectors include, but are not limited to, plasmids, viral vectors, non-episomal mammalian vectors and expression vectors, for example, recombinant expression vectors.

The recombinant expression vectors of the invention can comprise a nucleic acid of the invention in a form suitable for expression of the nucleic acid in a host cell. The recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells (e.g., SV40 early gene enhancer, Rous sarcoma virus promoter and cytomegalovirus promoter), those that direct expression of the nucleotide sequence only in certain host cells (e.g., tissue-specific regulatory sequences, see Voss et al., 1986, Trends Biochem. Sci. 11:287, Maniatis et al., 1987, Science 236:1237, incorporated by reference herein in their entireties), and those that direct inducible expression of a nucleotide sequence in response to particular treatment or condition (e.g., the metallothionin promoter in mammalian cells and the tet-responsive and/or streptomycin responsive promoter in both prokaryotic and eukaryotic systems (see id.). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

In another aspect, the present invention provides host cells into which a recombinant expression vector of the invention has been introduced. A host cell can be any prokaryotic cell or eukaryotic cell. Prokaryotic host cells include gram negative or gram positive organisms, for example E. coli or bacilli. Higher eukaryotic cells include insect cells, yeast cells, and established cell lines of mammalian origin. Examples of suitable mammalian host cell lines include Chinese hamster ovary (CHO) cells or their derivatives such as Veggie CHO and related cell lines which grow in serum-free media (see Rasmussen et al., 1998, Cytotechnology 28:31) or CHO strain DXB-11, which is deficient in DHFR (see Urlaub et al., 1980, Proc. Natl. Acad. Sci. USA 77:4216-20). Additional CHO cell lines include CHO-K1 (ATCC#CCL-61), EM9 (ATCC# CRL-1861), and UV20 (ATCC# CRL-1862). Additional host cells include the COS-7 line of monkey kidney cells (ATCC CRL 1651) (see Gluzman et al., 1981, Cell 23:175), L cells, C127 cells, 3T3 cells (ATCC CCL 163), AM-1/D cells (described in U.S. Pat. No. 6,210,924), HeLa cells, BHK (ATCC CRL 10) cell lines, the CV1/EBNA cell line derived from the African green monkey kidney cell line CV1 (ATCC CCL 70) (see McMahan et al., 1991, EMBO J. 10:2821), human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Appropriate cloning and expression vectors for use with bacterial, fungal, yeast, and mammalian cellular hosts are described by Pouwels et al. (Cloning Vectors: A Laboratory Manual, Elsevier, New York, 1985).

Vector DNA can be introduced into prokaryotic or eukaryotic cells via conventional transformation or transfection techniques. For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Additional selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die), among other methods.

The transformed cells can be cultured under conditions that promote expression of the polypeptide, and the polypeptide recovered by conventional protein purification procedures. Polypeptides contemplated for use herein include substantially homogeneous recombinant mammalian anti-human erythropoietin antibody polypeptides substantially free of contaminating endogenous materials.

Cells containing the nucleic acid encoding the antibodies of the present invention also include hybridomas. The production and culturing of hybridomas are discussed in the antibody section above.

Antibody Production

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody or a fragment of the antibody. Once a polynucleotide encoding an antibody molecule has been obtained, the vector for the production of the antibody may be produced by recombinant DNA technology. An expression vector is constructed containing antibody coding sequences and appropriate transcriptional and translational control signals. These methods include, for example, in vitro recombinant DNA techniques, synthetic techniques, and in vivo genetic recombination.

The expression vector is transferred to a host cell by conventional techniques and the transfected cells are then cultured by conventional techniques to produce an antibody of the invention. In one aspect of the invention, vectors encoding both the heavy and light chains may be co-expressed in the host cell for expression of the entire immunoglobulin molecule, as detailed below.

A variety of host-expression vector systems may be utilized to express the antibody molecules of the invention as described above. Such host-expression systems represent vehicles by which the coding sequences of interest may be produced and subsequently purified, but also represent cells which may, when transformed or transfected with the appropriate nucleotide coding sequences, express an antibody molecule of the invention in situ. Bacterial cells such as E. coli, and eukaryotic cells are commonly used for the expression of a recombinant antibody molecule, especially for the expression of whole recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, COS, 293, 3T3, or myeloma cells.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk, hgprt or aprt-cells, respectively. Also, antimetabolite resistance can be used as the basis of selection for the following genes: dhfr, which confers resistance to methotrexate (Wigler et al., Proc. Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 (Wu and Wu, Biotherapy 3:87-95 (1991)); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, "The use of vectors based on gene amplification for the expression of cloned genes in mammalian cells" (DNA Cloning, Vol. 3. Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and size-exclusion chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide. Fused or conjugated antibodies of the present invention may be used for ease in purification. See e.g., Harbor et al., supra, and PCT publication WO 93/21232; EP 439,095; Naramura et al., Immunol. Lett. 39:91-99 (1994); U.S. Pat. No. 5,474, 981; Gillies et al., Proc. Natl. Acad. Sci. 89:1428-1432 (1992); Fell et al., J. Immunol. 146:2446-2452 (1991).

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

Affinity and Activity of Antibodies

In one aspect, the present invention provides antibodies, in particular human, humanized, or chimeric antibodies, that specifically bind to human erythropoietin. Such antibodies include antagonizing or neutralizing antibodies, and non-neutralizing antibodies. Such antibodies can be of low, medium or high affinity binding to human erythropoietin. Exemplary properties of the antibodies of the invention are shown in Tables 6-8 herein.

In certain embodiments, the antibodies of the invention bind human erythropoietin with a KD of less than 100 pM. In other embodiments, the antibodies of the invention bind human erythropoietin with a KD of about 10 pM to about 100 pM. In other embodiments, the antibodies of the invention bind human erythropoietin with a KD of 10 pM to 100 pM. In other embodiments, the antibodies of the invention bind human erythropoietin with a KD of about 100 pM to about 1000 pM. In other embodiments, the antibodies of the invention bind human erythropoietin with a KD of at least 10 pM, at least 50 pM, at least 100 pM, at least 1000 pM, at least 5,000 pM, at least 10,000 pM, at least 50,000 pM, or at least 100,000 pM. In other embodiments, the antibodies of the invention bind human erythropoietin with a KD of about 1000 pM to about 5000 pM. In other embodiments, the antibodies of the invention bind human erythropoietin with a KD of 1000 pM to 5000 pM. In other embodiments, the antibodies of the invention bind human erythropoietin with a KD of about 20,000 pM to about 40,000 pM. In other embodiments, the antibodies of the invention bind human erythropoietin with a KD of 20,000 pM to 40,000 pM. In other embodiments, the antibodies of the invention bind human erythropoietin with a KD of about 100,000 pM to about 150,000 pM. In other embodiments, the antibodies of the invention bind human erythropoietin with a KD of 100,000 pM to 150,000 pM.

Binding to Human Erythropoietin

In one embodiment, the present invention provides antibodies that compete for binding with a reference antibody, wherein the reference antibody comprises a combination of light chain and heavy chain variable domain sequences selected from the sequences provided herein. In another embodiment, the present invention provides human antibodies that cross-compete for binding with a reference antibody, wherein the reference antibody is an anti-human erythropoietin antibody.

The ability to cross-compete with an antibody can be determined using any suitable assay. Numerous types of competitive binding assays can be used, for example: solid phase direct or indirect radioimmunoassay (RIA), solid phase direct or indirect enzyme immunoassay (EIA), sandwich competition assay (see, e.g., Stahli et al. (1983) Methods in Enzymology 9:242-253); solid phase direct biotin-avidin EIA (see, e.g., Kirkland et al., (1986) J. Immunol. 137:3614-3619) solid phase direct labeled assay, solid phase direct labeled sandwich assay (see, e.g., Harlow and Lane (1988) Antibodies, A Laboratory Manual, Cold Spring Harbor Press); solid phase direct label RIA using 1-125 label (see, e.g., Morel et al. (1988) Molec. Immunol 25:7-15); solid phase direct biotin-avidin EIA (see, e.g., Cheung, et al. (1990) Virology 176:546-552); and direct labeled RIA (Moldenhauer et al. (1990) Scand. J. Immunol. 32:77-82). Typically, such an assay involves the use of purified antigen bound to a solid surface or cells bearing either of these, an unlabelled test antibody and a labeled reference antibody. Competitive inhibition is measured by determining the amount of label bound to the solid surface or cells in the presence of the test antibody. Usually the test antibody is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to a common antigen by at least 40%, 45%, 50%, 55%, 60%, 65%, 70% or 75%. In certain embodiments, binding is inhibited by at least 80%, 85%, 90%, 95%, or 97% or more.

Epitope

As described herein, an epitope is the portion of a molecule that is bound by an antibody. An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antibody). Further, an epitope can comprise or consist of simply a linear, contiguous polypeptide sequence.

As shown in FIG. 4 (structure in figure adapted from Syed et al., Nature, 1998), antibodies of the invention were characterized and classed into three different epitope specificities or topographical binding domains on human erythropoietin—non-neutralizing, neutralizing that maps to the high affinity site 1 on human erythropoietin and neutralizing that maps to low affinity site 2 on human erythropoietin. Accordingly, the invention provides non-neutralizing anti-human erythropoietin antibodies that compete for binding with the antibodies of the invention. The invention further provides neutralizing anti-human erythropoietin antibodies that compete for binding with the antibodies of the invention that bind to high affinity site 1 of human erythropoietin. The invention further provides neutralizing anti-human erythropoietin antibodies that compete for binding with the antibodies of the invention that bind to low affinity site 2 on human erythropoietin.

Conjugates

According to certain aspects of the invention, agents can be conjugated to the antibodies of the invention for use in the compositions and methods of the invention. Such antibodies can be useful for monitoring or prognosing the onset, development, progression and/or severity of a disease or disorder (e.g., amPRCA) as part of a clinical testing procedure, such as determining the efficacy of a particular therapy. In certain embodiments, these conjugates can be generated as fusion proteins. Numerous proteins, enzymes, fluorochromes, isotopes or other detectable labels can optionally be conjugated to the antibodies of the invention. Antibodies of the present invention may optionally be covalently or non-covalently linked to such a detectable label.

Detectable labels suitable for such use include, but are not limited to, various enzymes, such as, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and acquorin; radioactive materials, such as, but not limited to, iodine ($^{131}I$, $^{125}I$, $^{123}I$, and $^{121}I$), carbon ($^{14}C$), sulfur ($^{35}S$), tritium ($^{3}H$), indium ($^{115}In$, $^{113}In$, $^{112}In$, and $^{111}In$), technetium ($^{99}Tc$), thallium ($^{201}Ti$), ($^{68}Ga$, $^{67}Ga$), palladium ($^{103}Pd$), molybdenum ($^{99}Mo$), xenon ($^{133}Xe$), fluorine ($^{18}F$), $^{153}Sm$, $^{177}Lu$, $^{159}Gd$, $^{149}Pm$, $^{140}La$, $^{175}Yb$, $^{166}Ho$, $^{90}Y$, $^{47}Sc$, $^{186}Re$, $^{188}Re$, $^{142}Pr$, $^{105}Rh$, $^{97}Ru$, $^{68}Ge$, $^{57}Co$, $^{65}Zn$, $^{85}Sr$, $^{32}P$, $^{153}Gd$, $^{169}Yb$, $^{51}Cr$, $^{54}Mn$, $^{75}Se$, $^{113}Sn$, and $^{117}Sn$; and positron emitting metals using various positron emission tomographies, and nonradioactive paramagnetic metal ions.

Covalent modifications of the anti-human erythropoietin antibody of the invention are included within the scope of this invention. They may be made by chemical synthesis or by enzymatic or chemical cleavage of the antibody, if applicable. Other types of covalent modifications of the anti-human erythropoietin antibody are introduced into the molecule by reacting targeted amino acid residues of the antibody with an organic derivatizing agent that is capable of reacting with selected side chains or the N- or C-terminal residues.

Cysteinyl residues most commonly are reacted with alpha-haloacetates (and corresponding amines), such as chloroacetic acid or chloroacetamide, to give carboxymethyl or carboxyamidomethyl derivatives. Similarly, iodo-reagents may also be used. Cysteinyl residues also are derivatized by reaction with bromotrifluoroacetone, alpha-bromo-beta-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysyl and amino-terminal residues are reacted with succinic or other carboxylic acid anhydrides. Derivatization with these agents has the effect of reversing the charge of the lysinyl residues. Other suitable reagents for derivatizing .alpha.-amino-containing residues and/or e-amino-containing residues include imidoesters such as methyl picolinimidate, pyridoxal phosphate, pyridoxal, chloroborohydride, trinitrobenzenesulfonic acid, 0-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginyl residues generally requires that the reaction be performed in alkaline conditions because of the high pKa of the guanidine functional group. Furthermore, these reagents may react with the epsilon-amino groups of lysine as well as the arginine epsilon-amino group.

The specific modification of tyrosyl residues may be made, with particular interest in introducing spectral labels into tyrosyl residues by reaction with aromatic diazonium compounds or tetranitromethane Most commonly, N-acetylimidizole and tetranitromethane are used to form O-acetyl tyrosyl species and 3-nitro derivatives, respectively. Tyrosyl residues are iodinated using $I^{125}$ or $I^{131}$ to prepare labeled proteins for use in radioimmunoassay.

Carboxyl side groups (aspartyl or glutamyl) are selectively modified by reaction with carbodiimides (R—N=C=N—R'), where R and R' are different alkyl groups, such as 1-cyclohexyl-3-(2-morpholinyl-4-ethyl)carbodiimide or 1-ethyl-3-(4-azonia-4,4-dimethylpentyl)carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the .alpha-amino groups of lysine, arginine, and histidine side chains (T. E. Creighton, Proteins: Structure and Molecular Properties, W.H. Freeman & Co., San Francisco, pp. 79-86 (1983)), acetylation of the N-terminal amine, and amidation of any C-terminal carboxyl group.

Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published 11 Sep. 1987, and in Aplin and Wriston, CRC Crit. Rev. Biochem., pp. 259-306 (1981).

Diagnostic Uses

Antibodies of the invention can be used to assay human erythropoietin levels in a biological sample using classical immunohistological methods as described herein or as known to those of skill in the art (e.g., see Jalkanen et al., 1985, J. Cell. Biol. 101:976-985; and Jalkanen et al., 1987, J. Cell. Biol. 105:3087-3096). Other nonlimiting examples of antibody-based methods useful for detecting protein gene expression include immunoassays, such as the enzyme linked immunosorbent assay (ELISA), Western blot, isoelectric focusing, and the radioimmunoassay (RIA). Suitable antibody assay labels are known in the art and are described herein.

In one aspect, the invention provides a method of detecting the presence of human erythropoietin in a biological sample. In certain embodiments, the method comprises contacting the biological sample with an anti-human erythropoietin antibody under conditions permissive for binding of the anti-human erythropoietin antibody to human erythropoietin, and detecting whether a complex is formed between the anti-human erythropoietin antibody and human erythropoietin.

In one aspect, the invention provides a method of diagnosing a disorder associated with increased expression of human erythropoietin. In certain embodiments, the method comprises contacting a test cell with an anti-human erythropoietin antibody; determining the level of expression (either quantitatively or qualitatively) of human erythropoietin by the test cell by detecting binding of the anti-human erythropoietin antibody to human erythropoietin; and comparing the level of expression of human erythropoietin by the test cell with the level of expression of human erythropoietin by a control cell (e.g., a normal cell of the same tissue origin as the test cell or a cell that expresses human erythropoietin at levels comparable to such a normal cell), wherein a higher level of expression of human erythropoietin by the test cell as compared to the control cell indicates the presence of a disorder associated with increased expression of human erythropoietin. In certain embodiments, the test cell is obtained from an individual suspected of having a disorder associated with increased expression of human erythropoietin. In certain embodiments, the disorder is a cell proliferative disorder, such as a cancer or a tumor.

In certain embodiments, a method of diagnosis or detection, such as those described above, comprises detecting binding of an anti-human erythropoietin antibody to human erythropoietin expressed on the surface of a cell or in a membrane preparation obtained from a cell expressing human erythropoietin on its surface, or human erythropoietin in soluble form in a human subject sample or media or other solution. In certain embodiments, the method comprises contacting a cell with an anti-human erythropoietin antibody under conditions permissive for binding of the anti-human erythropoietin antibody to human erythropoietin, and detecting whether a complex is formed between the anti-human erythropoietin antibody and human erythropoietin on the cell surface. A nonlimiting exemplary assay for detecting binding of an anti-human erythropoietin antibody to human erythropoietin expressed on the surface of a cell is a "FACS" assay. In certain embodiments, the antibodies of the invention can be used to assay for direct binding to human erythropoietin. In other embodiments, the antibodies of the invention can be used in a competitive assay to measure human anti-erythropoietin binding. In further embodiments, the antibodies of the invention can be used to assay for the presence of neutralizing or non-neutralizing antibodies in biological fluids.

The antibody subclass IgG4 is an indicator of a mature immune response. Development of antibody-mediated pure red cell aplasia (amPRCA) in a subject typically requires antibody maturation—isotype switching and affinity maturation. In subjects without amPRCA, there is a lack of anti-erythropoietin IgG4 antibodies, as is also the case in subjects with pre-existing anti-erythropoietin antibodies (generally IgG1 and IgM). It has been found that a strong correlation exists between the presence of anti-erythropoietin IgG4 antibodies and neutralizing antibodies. Accordingly, detecting the presence or increase of anti-erythropoietin IgG4 antibodies is useful for diagnosing, predicting, and following the progression of amPRCA in subject.

The presence of anti-human erythropoietin antibodies, including IgG4 subclasses, can be assayed for using any number of different immunoassays well known in the art. Further, it is conceived that assays that rely on detection of nucleic acids (e.g., Southern blot, Northern blot, PCR, RT-PCR, FISH) can be used to assay for the expression of anti-human erythropoietin antibodies. The presence or absence of anti-human erythropoietin IgG4 antibodies, and their increasing or decreasing levels, can be useful in, for example, detecting the onset of amPRCA, predicting the risk of amPRCA, and monitoring the progression of amPRCA. For example, a human subject prior to the initiation of treatment with human erythropoietin may shows no anti-human erythropoietin IgG4 antibodies being detected. If, upon treatment with human erythropoietin, the subject is tested and the presence of anti-human erythropoietin IgG4 antibodies is detected, this could indicate a risk of, or the onset of amPRCA. Further, if this subject is again tested at a later date and higher levels of anti-human erythropoietin IgG4 antibodies are detected, this could indicate progression of amPRCA. Conversely, if the subject is later tested and lower levels of anti-human erythropoietin IgG4 antibodies are detected, this could indicate regression of amPRCA.

Accordingly, in one embodiment, the invention provides a method of measuring anti-human erythropoietin IgG4 antibody levels in a human subject comprising determining in vitro a level of anti-human erythropoietin IgG4 antibodies in a sample from said subject and comparing said level to a level obtained from the anti-human erythropoietin IgG4 antibody 8C10 or 3A4. In certain embodiment, the level obtained from the 8C10 or 3A4 antibody is a level from a standard curve. In other embodiments, the level obtained from the 8C10 or 3A4 antibody is a level from their use as a positive control.

In another embodiment, the invention provides a method of measuring anti-human erythropoietin IgG4 antibody levels in a human subject comprising: contacting in vitro a blood or serum sample from said subject with a human erythropoietin, wherein the human erythropoietin captures anti-human IgG4 antibodies; contacting in vitro antibody 8C10 or 3A4 with a human erythropoietin, wherein the human erythropoietin captures 8C10 or 3A4; contacting said captured antibodies of steps a) and b) with a secondary anti-human IgG4 antibody that has been detectably labeled; and measuring the levels of said secondary antibody in each sample from step c). In certain embodiments, the levels from the human subject are compared to the levels from 8C10 or 3A4. In certain embodiment, the level obtained from the 8C10 or 3A4 antibody is a level from a standard curve. In other embodiments, the level obtained from the 8C10 or 3A4 antibody is a level from their use as a positive control.

In a further embodiment, the invention provides a method of detecting antibody-mediated pure red cell aplasia (amPRCA) in a human subject comprising determining in vitro a level of anti-human erythropoietin IgG4 antibodies in a sample from said subject and comparing said level to a level obtained from the anti-human erythropoietin IgG4 antibody 8C10 or 3A4, wherein an increase in a subject's anti-erythropoietin IgG4 levels indicates the onset or risk of amPRCA. In certain embodiment, the level obtained from the 8C10 or 3A4 antibody is a level from a standard curve. In other embodiments, the level obtained from the 8C10 or 3A4 antibody is a level from their use as a positive control.

In another embodiment, the invention provides a method of predicting the onset of antibody-mediated pure red cell aplasia (amPRCA) comprising determining in vitro a level of anti-human erythropoietin IgG4 antibodies in a sample from said subject and comparing said level to a level obtained from the anti-human erythropoietin IgG4 antibody 8C10 or 3A4, wherein an increase in a subject's anti-erythropoeitin IgG4 levels indicates the onset or risk of amPRCA. In certain embodiment, the level obtained from the 8C10 or 3A4 antibody is a level from a standard curve. In other embodiments, the level obtained from the 8C10 or 3A4 antibody is a level from their use as a positive control.

In yet another embodiment, the invention provides a method of predicting the risk of antibody-mediated pure red cell aplasia (amPRCA) comprising determining in vitro a level of anti-human erythropoietin IgG4 antibodies in a sample from said subject and comparing said level to a level obtained from the anti-human erythropoietin IgG4 antibody 8C10 or 3A4, wherein an increase in a subject's anti-erythropoeitin IgG4 levels indicates the onset or risk of amPRCA. In certain embodiment, the level obtained from the 8C10 or 3A4 antibody is a level from a standard curve. In other embodiments, the level obtained from the 8C10 or 3A4 antibody is a level from their use as a positive control.

As discussed, in certain embodiments, the antibody 8C10 or 3A4, or other anti-human erythropoietin IgG4 antibody of the invention, is used as a positive control. Nonlimiting examples for the use of the human anti-EPO IgG4 8C10 or 3A4 is as a reagent to monitor assay performance, trend, assess reproducibility, guide assay validation, set limits of an assay, or to confirm the binding to said EPO in an assay for human anti-EPO antibodies.

As discussed, in other embodiments, the antibody 8C10 or 3A4, or other anti-human erythropoietin IgG4 antibody of the invention, is used to generate a standard curve for levels of anti-human erythropoietin IgG4 antibodies so that samples (e.g., human subject samples) with unknown levels of anti-human erythropoietin IgG4 antibodies can be assayed and levels of such antibodies measured.

In other embodiments, the antibody 8C10 or 3A4, or other anti-human erythropoietin IgG4 antibody of the invention, are used to assay and compare the total anti-human erythropoietin IgG antibodies to anti-EPO IgG4, such that a ratio can be determined. In other embodiments, the antibody 8C10 or 3A4, or other anti-human erythropoietin IgG4 antibody of the invention, are used to assay and compare the total anti-human erythropoietin IgG1 antibodies to anti-human erythropoietin IgG4 antibodies, such that a ratio can be determined.

It is conceived that the antibodies of the invention can be used with any number of immunoassays well known in the art. A nonlimiting exemplary assay for measuring the anti-human erythropoietin IgG4 antibodies from a human subject is the ImmunoCAP™ assay (www.phadia.com). In this assay, human erythropoietin is covalently coupled to a solid phase and reacts with any anti-human erythropoietin antibodies present in the human subject's sample. After washing away nonspecific antibodies, labeled anti-human IgG4 antibodies are added, which form a complex with any anti-human erythropoietin IgG4 antibodies that have been captured by the human erythropoietin bound to the solid phase. After washing, the labeled anti-IgG4 antibodies are detected, allowing quantitation of the amount of anti-IgG4 antibodies, which allows quantitation of the amount of anti-human erythropoietin IgG4 antibodies from the subject's sample.

In one embodiment, the antibodies of the invention can be used as part of a reference panel of antibodies to validate and monitor assay performance (e.g., proficiency testing) and determine the limits of another assay platforms to detect the full repertoire of anti-human erythropoietin antibodies that may be present in a human subject sample after receiving treatment with a human erythropoietin. In certain embodiments, the panel of antibodies includes at least one of an IgG1, IgG2, and IgG4 subclass, as well as an IgM isotype.

In one embodiment, an immunoassay reference panel of antibodies includes mAb 8C10 and 3A4 to assess sensitivity using a high-affinity antibody and to ensure IgG detection. In another embodiment, the panel includes mAb 3F5 or 11D12 to assess detection of low-affinity IgG antibodies. In another embodiment, the panel includes mAb 11D12 or 9F7 to assess detection of low affinity IgM antibodies. In certain embodiments, any combination of the above antibodies can be used to generate an antibody panel.

In another embodiment, a bioassay reference panel of antibodies includes mAb 8C10 to assess sensitivity using a high-affinity neutralizing antibody and to assure IgG detection. In another embodiment, the panel includes mAb 3A4, 3F5, and 11D12 to assess detection of low-affinity IgG and/or IgM antibodies with moderate to weak neutralization. In certain embodiment, mAb 9F7 is used as a negative control for a binding, non-neutralizing antibody.

In one embodiment, the invention provides a kit for detecting amPRCA or predicting the risk or onset of amPRCA comprising an anti-human erythropoietin IgG4 antibody and human erythropoietin. In certain embodiments, the kit comprises the antibody 8C10 or 3A4, or other anti-human erythropoietin IgG4 antibody of the invention.

In one aspect, anti-human erythropoietin antibodies of the invention are useful for detecting the presence of human erythropoietin in a biological sample. The term "detecting" as used herein encompasses quantitative or qualitative detection. In certain embodiments, a biological sample comprises a cell or tissue. In certain embodiments, such tissues include normal and/or cancerous tissues that express human erythropoietin at higher levels relative to other tissues.

Certain other methods can be used to detect binding of anti-human erythropoietin antibodies to human erythropoietin. Such methods include, but are not limited to, antigen-binding assays that are well known in the art, such as western blots, radioimmunoassays, ELISA (enzyme linked immunosorbent assay), "sandwich" immunoassays, immunoprecipitation assays, fluorescent immunoassays, protein A immunoassays, and immunohistochemistry (IHC). In certain embodiments, anti-human erythropoietin antibodies are labeled, as described herein.

In certain embodiments, anti-human erythropoietin antibodies are immobilized on an insoluble matrix Immobilization entails separating the anti-human erythropoietin antibody from any human erythropoietin that remains free in solution. This conventionally is accomplished by either insolubilizing the anti-human erythropoietin antibody before the assay procedure, as by adsorption to a water-insoluble matrix or surface (Bennich et al., U.S. Pat. No. 3,720,760), or by covalent coupling (for example, using glutaraldehyde cross-linking), or by insolubilizing the anti-human erythropoietin antibody after formation of a complex between the anti-human erythropoietin antibody and human erythropoietin, e.g., by immunoprecipitation.

The invention having been described, the following examples are offered by way of illustration, and not limitation.

EXAMPLES

Example 1

Development of Human Anti-EPO Antibodies Using the XenoMouse Technology

Immunization

Fully human antibodies to EPO were generated by immunizing XenoMouse™ transgenic mice; strains used included XMG2-KL and XMG4-KL, (Mendez et al., 1997; Kellerman and Green, 2002). Mice were immunized with human Epoetin alfa (Amgen, Inc., Thousand Oaks, Calif.) 8 times over 4 weeks. For the initial immunization, each mouse was injected with a total of 10 µg of antigen by intraperitonial (IP) injection. Subsequent boosts were 5 µg doses, and injections were staggered between IP injections and subcutaneous (SC) injections at the base of the tail. For IP injections, antigen was prepared as an emulsion with Titer-Max® Gold (Sigma Aldrich, Oakville, Ontario) and for SC injections antigen was mixed with Alum prepared from aluminum potassium sulfate (EMD Chemicals Inc., Gibbstown, N.J.). A final injection of 5 µg of antigen per mouse was delivered in phosphate buffered saline (PBS) and delivered into 2 sites (50% IP into the abdomen and 50% SC at the base of tail). Serum titer was monitored by ELISA, and mice that tested positive for specific anti-EPO antibodies were sacrificed and used for hybridoma generation (Köhler and Milstein, 1975).

ELISA Binding Screens

Primary binding screens of the hybridoma lines identified 792 EPO specific binders using biotinylated EPO coated neutravidin plates as described above. To differentiate the antibodies by relative binding affinity, the panel of antigen specific binders was then compared in equilibrium based ELISA binding screens using decreasing amounts of biotinylated EPO (500-7.8 ng/mL). Methods used are described in U.S. Pat. No. 7,754,433. For binding screens with the avidin(N)-EPO variants, Costar 3667 Poly-D-Lysine 96 well plates were biotinylated with 50 µg/mL Sulfo-NHS-LC-Biotin (Thermo Scientific, Rockford, Ill.) in PBS pH 8.6 (50 µL/well) and incubated for 1 hr at 37° C. Free biotin was washed away, and the plates were then loaded with 1 µg/mL avidin(N)-EPO variant and incubated for 1 hour at room temperature. Plates were then washed and the ELISA completed as described above.

Antibody Competition ELISA

An antibody competition ELISA was performed using two mouse monoclonal antibodies (mAb F12, mAb D11) and a commercial antibody EPO-16 mAb (STEMCELL Technologies, Inc., Vancouver, British Columbia). The anti-EPO murine monoclonal antibodies were individually captured on ELISA plates coated with Goat anti-Mouse (Fc) antibody. Separately, hybridoma supernatants were mixed with biotinylated EPO conjugated through the carbohydrate moieties (EZ-Link Hydrazide-Biotin, Thermo Scientific, Rockford, Ill.) and incubated for 1 hour at room temperature. The biotinylated EPO hybridoma supernatant mix was then transferred onto the plates pre-coated with the murine antibodies and allowed to bind for 1 hour at room temperature. The plates were washed, and the amount of EPO bound to the plates was detected using a streptavidin-HRP conjugate (Thermo Scientific, Rockford, Ill.). Competition was observed as a reduction in the amount of EPO bound to the plate when EPO was complexed with a hybridoma supernatant versus EPO alone. Percent inhibition was determined by the following equation: % inhibition=1−[(sample OD)/(max OD)].

EPO Receptor Inhibition ELISA

An EPO receptor inhibition assay was performed by coating Costar medium binding plates (Corning, N.Y.) with EPO-R/Fc chimera (R&D Systems, Minneapolis, Minn.) at 2 µg/mL (30 µL/well) in PBS/0.05% sodium azide overnight at 4° C. Plates were then washed with 1×PBS and blocked with 1×PBS/1% milk assay buffer (125 µL/well) for 30 minutes at RT. Separately, excess amounts of hybridoma supernatants were mixed with biotinylated EPO conjugated through the carbohydrate moieties, in assay buffer for 1 hour at RT. After the incubation, 30 µL of the hybridoma supernatant and biotinylated EPO mixture was added to the EPOR-coated plates and incubated for 1 hour at RT. The plates were washed, and receptor bound EPO was detected using streptavidin HRP conjugate. The maximum EPO binding signal was the average signal observed using irrelevant hybridoma supernatant samples. Percent inhibition was determined by the following equation: % inhibition=1−[(sample OD)/(max OD)].

Cloning of Recombinant Antibodies

Hybridoma cells were collected and total RNA extracted using Qiagen RNeasy Mini Kit. The gamma heavy chain cDNA was obtained using Qiagen One Step Reverse Transcriptase PCR (RT-PCR) (Valencia, Calif.). This RT-PCR was used to generate the first strand cDNA from the RNA template and then amplify the variable region for the heavy chain using multiplex PCR primers. The 5' gamma primers annealed to the first 6-8 amino acids of the gamma heavy chain signal sequence, while the 3' primer annealed to the gamma constant region. The PCR reaction generated a 609 base pair product encoding a 203 amino acid peptide that included the signal sequence, the variable region (V-D-J), and the first 57 amino acids of the heavy chain constant region. The kappa light chain was obtained using Qiagen One Step RT-PCR (Valencia, Calif.). This RT-PCR was used to generate the first strand cDNA from the RNA template and then amplify the variable region for the kappa light chain using multiplex PCR primers. The 5' kappa primers annealed to the first 7-9 amino acids of the kappa light chain signal sequence, while the 3' primer annealed to the kappa constant region. The PCR reaction generated a 522 base pair product encoding a 174 amino acid peptide that included the signal sequence, the variable region (V-J), and the first 42 amino acids of the kappa constant region. The lambda light chain was obtained using Qiagen One Step Reverse Transcriptase PCR (RT-PCR) (Valencia, Calif.). This RT-PCR was used to generate the first strand cDNA from the RNA template and then amplify the variable region for the lambda light chain using multiplex PCR primers. The 5' lambda primers annealed to the first 7 amino acids of the lambda light chain signal sequence, while the 3' primer annealed to the lambda constant region. The PCR reaction generated a 466 base pair product encoding a 153 amino acid peptide that included the signal sequence, the variable region (V-J), and the first 16 amino acids of the lambda constant region. The VH chains were then cloned into an expression construct containing the original genomic IgG1 and IgG2 constant regions. The cDNA of the constant region of the IgG4 and IgM were used in place of genomic DNA to improve expression levels. The VL chains were cloned into their respective kappa or lambda expression constructs containing their constant region. To simplify purification of the IgM isotype antibodies, a FLAG 6× histidine tag (amino acid sequence DYKDDDDKHHHHHH (SEQ ID NO: 78)) was added to the C-terminus of the IgM constant region.

Expression and Purification of Avidin(N)-EPO Variants

Avidin(N)-EPO fusion proteins or variants FL, A, B, C, D, E, F, G, H, I, K, L, M, Q, and S (see Table 1b for details of each variant) were transiently expressed in CHO-S cells at 1-2 L scale as previously described (Haldankar et al., 2006). Based on coomassie blue gel stain analysis, the estimated expression was approximately 1-2 mg/L. About 2 L of culture media (CM) from CHO cell lines expressing avidin (N)-EPO was collected and then loaded onto a 60 mL IminoBiotin (IB) column (2 6×11 cm). The column was pre-equilibrated with 20 mM Na Borate, 0.5M NaCl, pH 10. After loading, the column was washed with 5 column volumes of the equilibration buffer and eluted with 20 mM NaOAc, 0.15M NaCl pH 4. IB pool (90 mL) was immediately neutralized with 1M Tris-HCl, pH 9.2 to pH 7.1. Samples were purified by SP-HP Chromatography according to the following: approximately 90 mL of IB pool was diluted with 180 mL of cold water. The diluted IB pool was loaded onto a 5 mL Hi-Trap SP-HP column. The column was pre-equilibrated with 10 mM $NaPO_4$, pH 7.2. After loading, the column was washed with 5 column volumes of the equilibration buffer and eluted with 25 column volumes of a gradient from 0-400 mM NaCl in 10 mM $NaPO_4$, pH 7.2. Filtered Purified Bulk: SP-HP pool (45 mL) was concentrated to 5.2 mL, 2.75 mg/mL. The concentrate was filtered with 0.2 μm Pall Acrodisc syringe filter. Each mutant was then purified by size exclusion chromatography according to AUFS 0.5, 5 mL/min, 5 mL/Fx SP-HP#12-21, total 50 mL, then concentrated to 4.6 mL, 3 mg/mL, and finally filtered through a 0.2 micron filter.

To correlate changes in immunological reactivity as a result of the direct EPO mutagenesis of key residues (and not changes in protein structure of the molecule and thus alter a conformational epitope), we performed Differential Scanning calorimetry (DSC) analysis as previously described (Wen et al., 2007) on purified avidin(N)-EPO variants and immunological reactivity of the three murine anti-EPO antibodies against all avidin(N)-EPO variants referred to in Table 1b.

Expression and Purification of Human Anti-EPO Antibodies

Each of the recombinant human antibodies was transiently expressed in the human embryonic kidney 293 cell line stably expressing Epstein Barr virus Nuclear Antigen-1 (293-EBNA1) (National Research Council, Montreal, Canada) (Durocher et al., 2002). Cells were maintained as serum-free suspension cultures using F17 medium (Invitrogen, Carlsbad, Calif.) supplemented with 6 mM L-glutamine (Invitrogen, Carlsbad, Calif.), 1.1% F-68 Pluronic (Invitrogen, Carlsbad, Calif.), and 50 μg/μL Geneticin (Invitrogen, Carlsbad, Calif.). The suspension cell cultures were maintained in 3 L Erlenmeyer shake flasks (Corning, N.Y.) with 1 L working volume on an Innova 2100 platform shaker (New Brunswick Scientific, Edison, N.J.). Cultures were incubated in a reach-in incubator (Forma Scientific, Asheville, N.C.) at 37° C. and maintained in a humidified, 5% $CO_2$ atmosphere. Cells were transfected using standard expression conditions that have been previously described (Durocher et al., 2002). The standard harvest time was 7 days post-transfection. The estimated titer from the large scale production of each recombinant human antibody was >100 mg/L. Approximately 2 L of conditioned medium was then purified over a Protein A column. Protein A purification was not suitable for the 11D12 IgM isotype antibody and instead a nickel affinity resin was used. The purified antibody was then characterized by SDS-PAGE, HPLC, and N-terminal sequencing.

Example 2

Biosensor Immunoassay

Antibody Detection Using the Biosensor Immunoassay

The biosensor immunoassay was performed on a Biacore 3000 instrument (BIAcore, a GE Healthcare Company) to measure human antibody binding to EPO. The immunoassay method was previously published (Mytych et al., 2009). In brief, Epoetin alfa (30.4 kDa, 4.03 mg/mL, >95% purity based on SDS-PAGE) and darbepoetin alfa (37.3 kDa, 1.99 mg/mL, >95% purity based on SDS-PAGE) were covalently immobilized onto separate flow cells of a CM5 biosensor chip (BIAcore, Inc. a GE Healthcare Company) through the primary amines of the protein with micelle-assisted amine chemistry. After immobilization, human antibodies were diluted and injected (50 μL; 10 μL/min) across each Epoetin alfa surface. Sample binding was confirmed to be human antibodies by injecting (20 μL) goat anti-human IgA+IgM+ IgG (H+L) followed by surface regeneration (50 mM HCl, 2.5% P-20, 1.5M Guanidine-HCl) to remove serum proteins. Antibody samples were considered positive to EPO if: (1) the sensor surface response units (RU) were the threshold value to discriminate specific from non-specific binding determined during assay validation, (2) the anti-human antibody RU was at least 2-fold higher than the serum sample RU. The limit of detection (LOD) for this immunoassay was 80 ng/mL of anti-EPO antibodies.

Antibody Isotype and IgG Subclass

The human antibody isotype and IgG subclass for each human antibody sample was determined. The qualified antibody isotyping reagents included anti-human IgG, IgE (ICN Pharmaceuticals, Costa Mesa Calif.), and IgM (Fitzgerald Industries International, Concord, Mass.) that were diluted to 100 μg/mL. Anti-human IgA (ICN Pharmaceuticals, Costa Mesa, Calif.) was diluted to 200 μg/mL. Positive identification for a given isotype was recorded if: (1) there were at least 100 RUs of sample binding, and (2) an increase of at least 100 RUs (over the sample binding) observed after injection of the isotyping reagent. The subclasses of IgG were determined by similar methods, except that antibodies specific for human IgG1, IgG2, IgG3, and IgG4 antibodies (The Binding Site Inc., San Diego, Calif.) were used.

Antibody Affinity by BIAcore

Kinetic analysis of purified anti-EPO monoclonal antibodies was performed with the Biacore A100 (Biacore, a GE Healthcare Company) using a previously described method (Säfsten et al., 2006). In summary, goat anti-human IgG, Fc (Jackson Immunoresearch, West Grove, Pa.) was immobilized onto spot 1, 2, 4, and 5 with standard amine coupling chemistry (Johnsson et al., 1991). Spot 3 was used as a blank reference. Each antibody was diluted to a concentration (typically 0.5 to 1 μg/mL) to allow a maximum Epoetin alfa binding level between 50 and 100 RU. Epoetin alfa was serially diluted from 400 nM to 3.13 nM. Instrument protocol included human antibody injections (20 μL, 10 μL/min) followed by Epoetin alfa (75 μL, 30 μL/min) and a 5-minute dissociation period. Surface regeneration was performed by injection of 60 μL of a 50 mM glycine, pH 1.7 at 30 μL/minute. Kinetic interactions between the mAb and Epoetin alfa were calculated using Biacore A100 evaluation software.

Cross-Reactivity to Other ESAs Using BIAcore

The described biosensor immunoassay method was used to determine cross-reactivity of two human antibodies against other commercially available ESAs (Silapo™, Eprex™ Mircera™, and Neorecormon™). Each ESA was immobilized to the biosensor flow cells using micelle-assisted amine coupling to a final surface density of approximately 1500 to 2500 RU. Each human antibody was serially diluted in pooled normal human serum to make a standard concentration curve (0.01 to 10 µg/mL). Sensitivity of each mAb to the ESA was estimated by determining the concentration at which the serum sample binding was twice that of pooled normal human serum.

Example 3

Bridging ECL Assay

The assay sensitivity associated with each human antibody was determined with a previously described bridging ECL immunoassay (Barger et al., 2011). Briefly, Epoetin alfa was separately conjugated to biotin using carbohydrate coupling chemistry (Thermo Scientific, Rockford Ill.) or Sulfo TAG ruthenium (MSD, Gaithersburg, Md.). Biotinylated Epoetin alfa was diluted to 0.50 µg/mL and incubated in wells of a streptavidin coated plate (MSD, Gaithersburg, Md.). Wells were washed and 10% diluted serum samples were added to plate wells. After a second plate wash, 0.50 µg/mL ruthenium-Epoetin alfa was added and allowed to incubate. A final plate wash was performed and Read Buffer T (MSD, Gaithersburg, Md.) was added to individual plate wells and read on an MSD Sector Imager 6000 (MSD, Gaithersburg, Md.) using MSD Workbench™ version 2.0.7.3. Results were reported as unknown sample ECL (S) to negative control ECL (N) ratio (S/N).

Example 4

CBA Epitope Mapping of Human Antibodies Using Avidin-EPO Variants

To assess the epitope specificity of the human antibodies, a cytometric bead assay (CBA) was developed using EPO variants with single amino acid substitutions (Elliot et al., 1997). In brief, biotin-labeled beads were coated with different avidin-EPO variants using either purified or culture media (CM) containing the variants. Each antibody sample was tested for binding to avidin-full length erythropoietin (avidin-FL-EPO) and compared to the binding to 15 avidin-EPO variants containing non-neutralizing epitopes and variants containing site-specific substitutions within the EPO domains critical for engaging the erythropoietin receptor (see Table 1b). Beads were first blocked with 5% bovine serum albumin (BSA) in phosphate buffered saline (PBS), coated with 100 µL avidin-EPO variants at 0.1 µg/mL or 14 ng/mL in 1% culture media, incubated for 1 hour, and then washed. All human antibodies were spiked into neat serum at 10 µg/mL and then diluted 1:200 in assay diluent. A 100 µL aliquot of each sample was incubated with each of the 15 avidin-EPO variants for 1 hour and then washed. Finally, goat anti-human IgG-PE antibody was added, incubated for 1 hour, and washed. Beads were acquired on a FACS Canto II flow cytometer (Becton Dickinson, San Jose, Calif.). Results were expressed as % binding loss to each avidin-EPO variants relative to binding to avidin-FL-EPO.

Example 5

Neutralizing Antibody Bioassay

A cell-based bioassay was used to detect neutralizing antibodies against Epoetin alfa in serum samples. The assay utilizes the cell line 32D-EPOR, which depends on Epoetin alfa for proliferation. Neutralizing antibodies against Epoetin alfa inhibit erythropoietin-dependant proliferation. Full details of this assay have been described elsewhere (Wei et al., 2004). Briefly, 20,000 cells per well were plated in 96-well plates, and incubated with 1 ng/mL Epoetin alfa and the test samples for 44±1 hr at 3TC, 5% $CO_2$ and 95% relative humidity. Cell proliferation was assessed by measuring the incorporation of $^3$H-thymidine into cellular DNA, and expressed as counts per minute (cpm). The lower limit of detection is 500 ng/mL anti-Epoetin alfa antibodies. The percent (%) neutralization of each antibody was expressed by normalizing the cpm response of each sample by the maximum proliferation control.

Example 6

Hybridoma Epitope Binning

Epitope binning is a technique to sort antibodies based on their epitope specificities and group the antibodies with similar pairing profiles. An antibody competition ELISA using murine monoclonal antibodies was performed to recognize known conformational epitopes on EPO (see Table 1a) to epitope bin the hybridomas. A loss in hybridoma antibody binding to EPO in the presence of the EPO-bound murine antibody indicated that the hybridoma antibodies bind EPO with similar or overlapping epitope specificity as the murine mAb.

A total of 206 hybridoma lines could be discretely assigned to an epitope competition bin (data not shown); 163 were inhibited by mAb 16 by >80%, 40 were inhibited by mAb D11 >80% and only 3 hybridomas were inhibited by F12 >69%. There were also a small number of antibodies that did not fall into only one discrete epitope bin; 4 lines were observed to compete with both mAb D11 and mAb 16 and another 12 lines were observed to compete against both mAb D11 and F12. The hybridoma lines which showed competition to 2 different antibodies could be polyclonal hybridoma lines with two different specificities. These antibodies were not taken forward to subcloning to conclusively determine the epitope. The remainder of the hybridoma lines had partial inhibition (535), enhanced binding (26) or no inhibition (9). The grouping of these hybridomas with similar profiles indicated that the antibodies bound to the same or closely related epitopes. The initial binning allowed for the selection of hybridomas that compete for binding to the non-neutralizing epitope recognized by mAb F12. Of most interest, the majority of the hybridoma lines produced human antibodies that competed with neutralizing mAb 16 and D11.

From the initial hybridoma screen, 12 hybridoma cell lines were selected from the 4 groups of antibody bins described in FIG. 1. The results of the small scale antibody purification of the 12 subcloned hybridoma cell lines are presented in Table 2a. Seven antibodies showed at least 78% inhibition in the EPO receptor (EPOR) binding ELISA; six of these antibodies were blocked by mAb 16, suggestive of recognition of the high affinity receptor binding site 1 on EPO. Antibody 10H12, which demonstrated strong inhibition in the EPOR binding ELISA, was blocked by D11 binding suggestive of recognition of the low affinity receptor binding site 2 on EPO. Two additional antibodies, 11D12 and 3F8 also were blocked by D11 antibody. Despite the blocked binding by D11, antibody 11D12 had a weak inhibition (22%) while 3F8 had no inhibition in the EPO receptor inhibition ELISA. The remaining 3 antibodies (5G1, 9F7 and 10B5) were not inhibitory in the EPOR binding ELISA. This data suggested that 3F8, 5G1, 9F7 and 10B5 were non-neutralizing antibodies.

Despite the identification of 10H12 binding to site 2 on EPO, a second screen was initiated to identify additional discrete antibody hybridomas with strong neutralizing capacity for the low affinity receptor binding site 2. All 792 hybridomas supernatants were re-screened in the ELISA to identify reduced binders against EPO A and EPO I avidin-EPO variants (which contain mutations in the site 2 domain) relative to EPO FL avidin-EPO variant (contains no mutation). The results of screen 2, which are shown in Table 2b, identified hybridoma 3A4 and 14G10. Both demonstrated antibody competition with D11 and significant inhibition in the EPO receptor inhibition ELISA; however, 3A4 was sensitive to EPO I, which contained a substitution at residue 103 whereas 14G10 was sensitive to EPO A, which had a substitution at residue 14. Since the 3A4 hybridoma had a much stronger neutralization (90%), 14G10 was not pursued further and 3A4 was subsequently subcloned and purified.

A total of 13 purified antibodies were then further tested in a cytometric bead assay (CBA) using a large panel of avidin(N)-EPO variants which contain single point mutations within EPO to map the antibody binding epitope at high resolution. Each purified antibody was tested for binding to the full-length EPO (FL) and then assessed for loss of binding to the 14 avidin(N)-EPO variants (see Table 1b). The use of avidin(N)-EPO variants was previously described (Burgess et al., 2006). The results are shown in Table 3 and were used to determine the potential neutralizing activity of each antibody and to map which of the two mutually exclusive epitopes were responsible for EPOR binding (Cheetham et al., 1998). These two nonequivalent receptor binding sites on EPO were reported to have different affinities for the EPOR: the high affinity receptor binding site or site 1 (~1 nM) and the low affinity receptor binding site or site 2 (~1 µM) based on studies using the extracellular domain of the EPOR in solution (Philo et al., 1996).

Six of the thirteen antibodies (8C10, 6E12, 7F1, 3F5, 8H10 and 14F5), which had at least 78% inhibition in the EPOR inhibition ELISA and were blocked by mAb 16 (see Table 2a) all recognized key residues clustered within the high affinity site 1 binding domain as evidenced by the lack of binding to EPO E, EPO F or EPO M in the CBA. In addition, antibody 5G1, which was blocked by mAb 16, had reduced binding to EPO E suggesting the epitope it binds was within the high affinity site 1 binding domain. The lack of EPOR inhibition may be related to affinity. The strong EPOR inhibition (78%) and the loss of binding to EPO in the presence of murine antibody D11 (and F12) demonstrated by 10H12 was consistent with the CBA data demonstrating the loss of binding to EPO G, which contained a mutation at residue 96 located within the low affinity receptor site 2 on EPO. The CBA analysis of 3F8 and 9F7 antibody demonstrated that residue 116 was critical for 3F8 binding and residue 32 critical for 9F7 binding to EPO, both residues not involved in EPO receptor binding and therefore not expected to be neutralizing. The epitope for antibody 10B5 and 11D12 was not identified using the 14 avidin-EPO variants. Finally, CBA analysis of antibody 3A4 confirmed the previous ELISA data, demonstrating that 3A4 lacked binding to EPO I, which contained a substitution at residue 103 and is within the low affinity receptor site 2 on EPO.

TABLE 4

Characteristics of Epitope Binning Reagents a) Murine anti-huEPO Monoclonal Antibodies

| Reference mAb | Source | Epitope Type | Neutralizing Activity | Avidin-EPO variants with reduced binding | Epitope Site (Amino acid residues critical for mAb binding) |
| --- | --- | --- | --- | --- | --- |
| D11 | Amgen | Conformational | + | EPO I | 64-78, 99-110 |
| F12 | Amgen | Conformational | − | EPO D | 31-33, 86-91 and 138 |
| 16F1H11(16) | STEMCELL | Conformational | + | EPO E | ND | b) Avidin-EPO Variants

| Avidin-EPO variant | AA Mutation Site | Native AA | Mutated AA | Marker | Epitope |
| --- | --- | --- | --- | --- | --- |
| FL | None | None | None | NA | NA |
| A | 14 | Arg | Gln | A Helix | Site on EPO that binds cellular receptor with low affinity (site 2) |
| B | 15 | Tyr | Ile | | |
| C | 20 | Lys | Gln | | |
| G | 96 | Asp | Arg | C Helix | |
| H | 100 | Ser | Glu | | |
| I | 103 | Arg | Ala | | |
| E | 45 | Lys | Asp | AB loop | Site on EPO that binds cellular receptor with high affinity (site 1) |
| F | 49 | Tyr | Ser | | |
| K | 147 | Asn | Lys | D Helix | |
| L | 150 | Arg | Ala | | |
| M | 155 | Leu | Ala | | |
| Q | 87 | Pro | Val | BC loop | Non EPOR binding |

TABLE 4-continued

Characteristics of Epitope Binning Reagents

| | | | | | |
|---|---|---|---|---|---|
| D | 32 | His | Ile | AB loop | region |
| S | 116 | Lys | Glu | CD loop | | a) Monoclonal antibodies were selected to compete for epitope binding on EPO. Binding inhibition indicated a shared epitope to the reference antibody.
b) Avidin-EPO variants were used to determine the antibody binding epitope on EPO. Reduced antibody binding to a variant as compared to native EPO FL indicated that the mutated amino acid residue is a critical residue within the epitope for antibody binding.

TABLE 5

Epitope binning of the hybridomas. (a.) Purified antibody from the subcloned lines was tested by epitope competition ELISA with murine antibodies and in an antibody dependent inhibition of EPO binding to EPO receptor. (b.) A second screen was performed to identify additional hybridomas producing antibody to the low affinity receptor site 2 on EPO. Hybridoma supernatant was used to assess binding in an ELISA to two avidin(N)-EPO variants and FL-EPO.

a.

| Screen 1 | | Antibody Competition ELISA (% Inhibition) [Ab] = 10 µg/mL | | | EPO Receptor Inhibition ELISA [Ab] = 10 µg/mL |
|---|---|---|---|---|---|
| Antibody ID | Hybridoma Supernatant Selection Bin | D11 | F12 | mAb 16 | % Inhibition |
| 8C10 | A | 0 | 9 | 95 | 90 |
| 6E12 | A | 0 | 18 | 96 | 86 |
| 7F1 | A | 22 | 22 | 98 | 95 |
| 10H12 | A | 96 | 95 | 18 | 78 |
| 3F5 | B | 10 | 30 | 97 | 89 |
| 8H10 | B | 14 | 35 | 96 | 94 |
| 14F5 | B | 0 | 40 | 92 | 84 |
| 11D12 | C | 83 | 0 | 0 | 22 |
| 3F8 | D | 41 | 0 | 24 | 0 |
| 5G1 | D | 0 | 0 | 46 | 0 |
| 9F7 | D | 0 | 20 | 0 | 0 |
| 10B5 | D | 25 | 0 | 0 | 0 | b.

| Screen 2 | | Antibody Competition ELISA (% Inhibition) [Ab] = 10 µg/mL | | | EPO Receptor Inhibition ELISA [Ab] = 10 µg/mL | EPO variant binding ELISA (OD) | | |
|---|---|---|---|---|---|---|---|---|
| Antibody ID | Hybridoma Supernatant Selection Bin | D11 | F12 | mAb 16 | % Inhibition | EPO-FL | EPO-A | EPO-I |
| 3A4 | B | 91 | 30 | 0 | 90 | 3.33 | 2.35 | 0.18 |
| 14G10 | C | 40 | 0 | 0 | 69 | 3.46 | 0.51 | 3.38 |

Example 7

Affinity Analysis by BIAcore and Neutralization in a Bioassay

The binding affinity and neutralization for the 13 purified human antibodies was examined using the Biacore A100 and a bioassay. The data is summarized in Table 3. Seven antibodies with confirmed binding specificity to the high affinity receptor binding site (site 1) on EPO demonstrated a broad range of affinities that correlated with neutralizing capacity in the bioassay. The 3 antibodies (8C10, 7F1 and 8H10) with KD values below 300 pM exhibited high neutralization for EPO (between 74% and 100%), while the 4 antibodies (6E12, 14F5, 3F5 and 5G1) with KD values greater than 500 pM exhibited weak neutralization (between 5% and 17.6%). The antibody 8C10 demonstrated the highest affinity (8 pM) with an extremely fast on (ka) and slow off rate (kd) followed by 7F1, 8H10, 6E12, 14F5, 3F5 and 5G1 respectively. The two antibodies (10H12 and 3A4) with confirmed binding specificity to the low affinity receptor binding site (site 2) on EPO demonstrated moderate neutralization in the bioassay despite a high affinity for EPO (KD of 110 and 148 pM, respectively). The four non-neutralizing antibodies (3F8, 9F7, 11D12 and 10B5) had relatively low affinity for EPO (74, 119, 5.5 and 178 nM KD respectively) and relatively fast off-rates, ranging from $10^{-2}$ to $10^{-4}$ $s^{-1}$.

Example 8

Cloning and Isotype/IgG Subclass Selection for Recombinant Antibody Production Four subcloned hybridoma cell lines (3F8, 3F5, 8C10 and 3A4) were advanced for variable heavy (VH) and variable light (VL) chain sequencing and cloning to develop IgM and IgG subclass-specific recombinant human antibodies. The selection of which human antibody isotype and IgG subclass to develop was based on historical isotype and subclass data collected at Amgen on antibody-positive patient serum from clinical and safety testing.

A summary of the prevalence of anti-EPO antibody isotypes confirmed in the Biacore immunoassay from over 6,000 patients in three study populations is presented in Table 4. The patient population included subjects administered Epoetin alfa or darbepoetin alfa. Both IgM and IgG1 anti-EPO antibody isotypes were most prevalent. This analysis adds to previously published descriptions of binding, non-neutralizing anti-EPO IgM and IgG1 antibodies in non-PRCA patients (Barger et al., 2011). However, patients that develop antibody-mediated PRCA do not have anti-EPO IgM, but rather exhibit a mixed neutralizing IgG subclass with a high incidence of anti-EPO IgG4 antibodies (Swanson et al., 2004). Based on these clinical datasets, an IgM isotype and IgG1, IgG2 and IgG4 subclass antibodies were developed. Since published data has identified the predominance of IgG1 and IgG4 seen in antibody-mediated PRCA subjects, VH and VL chains from the neutralizing human antibody clone 8C10 were cloned onto an IgG1, IgG2 and IgG4; 3A4 onto an IgG4; and 3F5 onto an IgG1 framework. The purpose of developing 8C10 IgG1, IgG2 and IgG4 subclass antibodies was to provide an appropriate anti-EPO neutralizing IgG subclass standard for both immunoassay and bioassay. In addition, these antibodies will be used in the biosensor immunoassay method to validate the sensitivity of the Biacore method using each IgG subclass reagent. Despite the promising non-neutralizing binding characteristics demonstrated by the purified antibody from the subcloned 3F8 cell line, the cloning and expression proved difficult. Due to low level of expression and lack of EPO binding, this antibody was not pursued further. Therefore, the VH and VL chains of the weakly neutralizing antibody 11D12 were cloned onto an IgM and IgG2 framework. In addition, the non-neutralizing 9F7 VH and VL chains were cloned onto an IgM and IgG2 framework. It is important to note that the recombinant IgM was cloned and expressed as a monomeric antibody. The development of an anti-EPO IgG3 antibody was not considered because cloning and expression proved extremely difficult due to the inherent instability caused by the numerous disulfides in the hinge region of IgG3 isotypes. A total of 9 recombinant human antibodies were generated for further testing.

Example 9

Evaluation of the Recombinant Human Antibodies

Characterization

The detailed characterization of all nine recombinant human antibodies is shown in Table 5. After transient expression in 293 suspension cells, the antibodies went through large scale Protein A purification followed by SDS-PAGE, HPLC, and N-terminal sequencing (data not shown). All purified antibodies were then tested using the previously described battery of assays. First, each antibody was characterized for isotype/subclass, affinity for EPO by Biacore, and EPO epitope specificity by CBA. To determine the antibody isotype and subclass by Biacore, each antibody was injected across an EPO-immobilized flow cell followed by the subsequent injection of the anti-human isotype and anti-human IgG subclass specific antibodies. As expected, all recombinant antibodies were confirmed to have the expected immunoglobulin isotype or IgG subclass as shown in Table 5. The antibody affinity for EPO was determined on the Biacore A100. The affinity was similar between the antibodies purified from the subcloned hybridoma (see Table 4) and the large scale purified recombinant antibodies presented in Table 5 with the most notable differences in 3A4 and 8C10. The largest difference was observed in the highest affinity mAb 8C10. Analysis of the fine epitope specificity of each antibody using the avidin-(N)EPO variants confirmed the EPO epitope binding assessed from the subcloned hybridoma.

Immunoassay Detection

Figure 2:
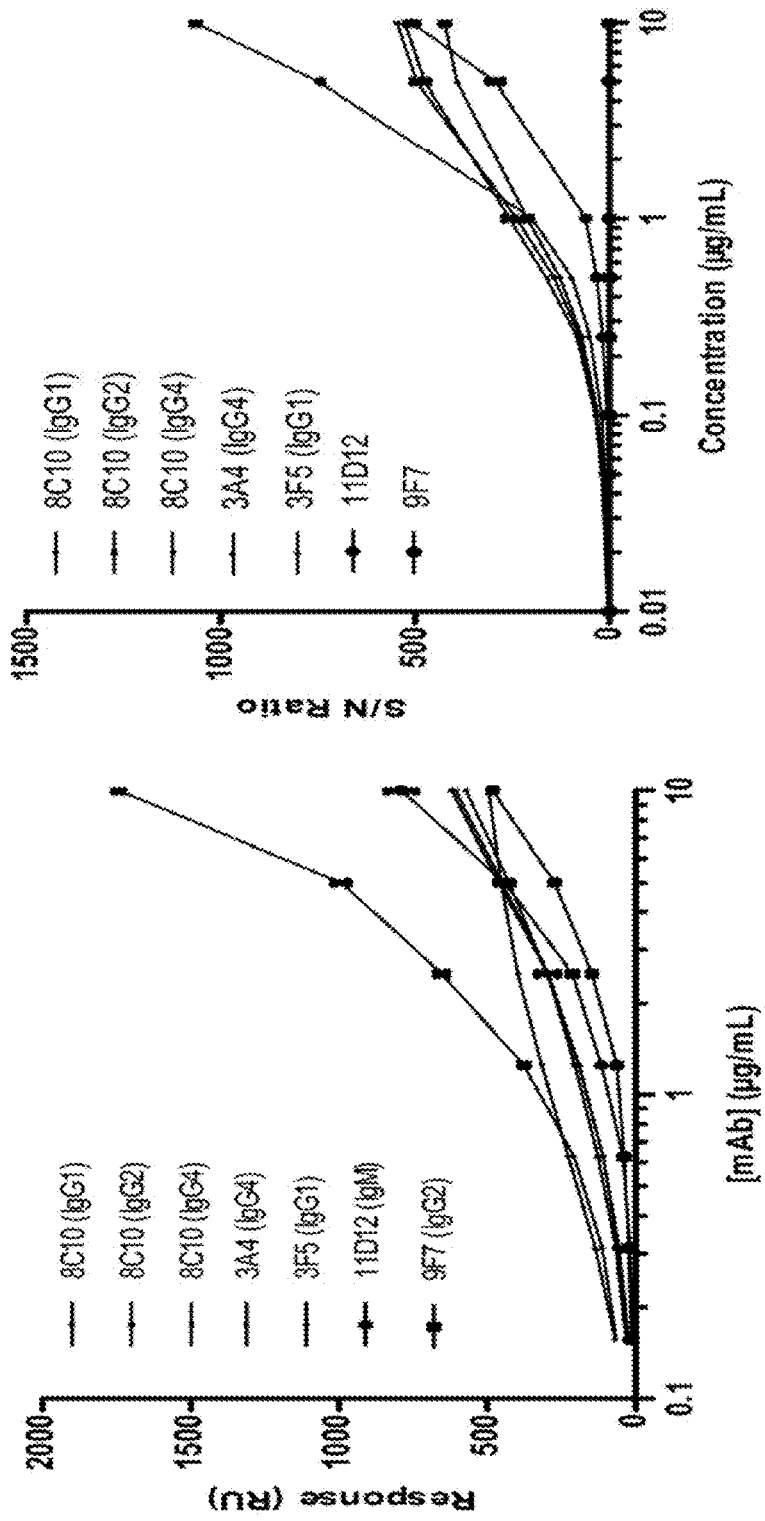
FIG. 2. Dose-response curves demonstrating binding of each recombinant human anti-EPO antibody to immobilized EPO as determined by the following: a.) Biacore Immunoassay and b.) Bridging ECL assay.

With the characteristics of the recombinant antibody panel confirmed, each antibody was evaluated in two different immunoassay methods. Both the Biacore and bridging ELISA methods are used routinely for anti-ESA antibody detection (Thorpe and Swanson, 2005), and both methods have previously been reported (Mytych et al., 2009; Hoesel et al., 2004). In the Biacore immunoassay, all antibodies were serially diluted from 10 µg/mL to 0.156 µg/mL of antibody in neat serum, diluted 1:2 in diluents, and tested for binding to the immobilized EPO surface. The Biacore immunoassay results shown in FIG. 2a demonstrate a dose dependent increase in binding (in RU) with an increase in antibody concentration for all antibodies tested. The lowest antibody concentration above background was reported in Table 5 as the sensitivity. The 3A4 antibody outperformed all others in dynamic binding to EPO both at a high antibody concentration as well as being detected positive at 20 ng/mL. The antibodies 8C10, 3F5, and 9F7 were all detected positive below the 100 ng/mL concentration despite significant differences in affinity or differences in subclass. Finally, the low affinity antibody 11D12 demonstrated a sensitivity of 272 ng/mL of antibody. The antibody panel was then tested with a bridging ECL assay. All antibodies were serially diluted from 10 µg/mL to 0.010 µg/mL of antibody in neat serum and diluted 1:10 in diluent. The results of the bridging ECL assay, shown in FIG. 2b, demonstrate a dose dependent increase in binding (in S/N) with an increase in antibody concentration for all antibodies except 3F5 and 9F7. Both 3F5 and 9F7 had no detectable binding even at the 10 µg/mL concentration. The lowest antibody concentration that produced an S/N greater than 1.16 was reported in Table 5 as the antibody sensitivity. As with the Biacore immunoassay, antibody 3A4 outperformed all others in binding to EPO at the high antibody concentration, but 3A4, 8C10 and 11D12 were all detected at concentrations <10 ng/mL. The detection of antibody 8C10 and 11D12 in both immunoassays was not influenced by antibody IgG subclass or isotype respectively.

Neutralizing Antibody Bioassay Dose Response

Figure 3:
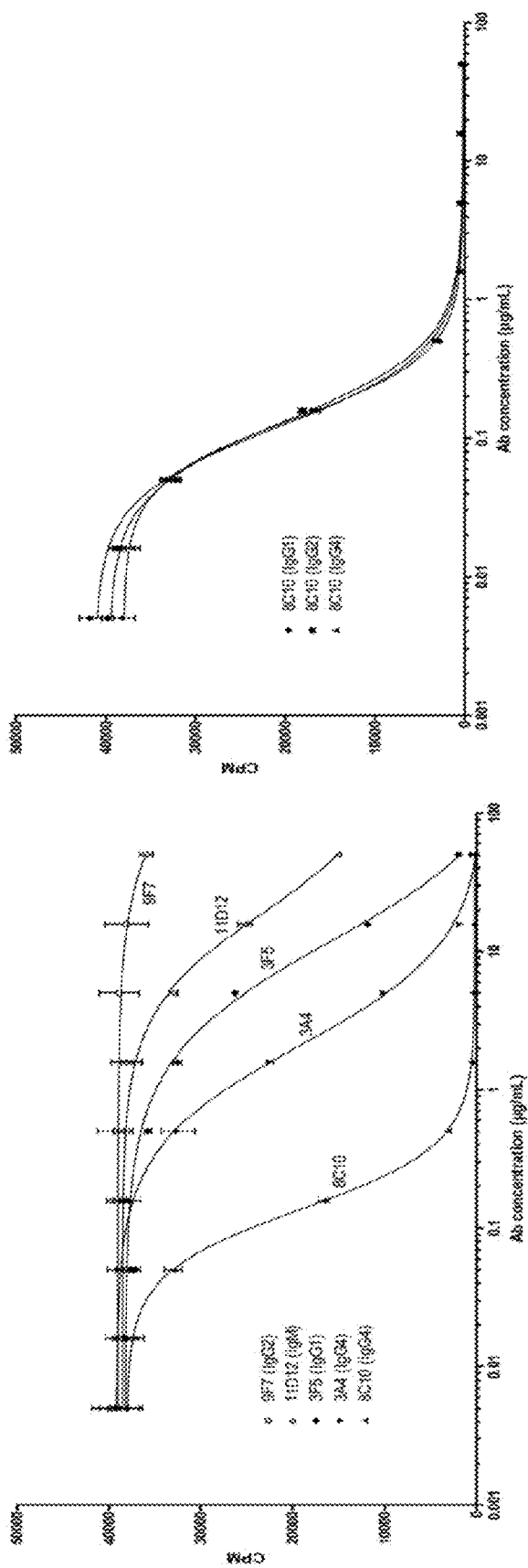
FIG. 3. Concentration-dependent neutralization in a cell-based assay of five antibodies, including a non-neutralizing antibody 9F7 (a); and 8C10 containing different IgG subclasses (b).

The cell-based assay was used to measure the capacity of each recombinant antibody to neutralize erythropoietin-responsive cells. Each antibody was prepared as a dose-response curve by serially diluting in neat serum (50.0 to 0.005 µg/mL). The antibody dose-response curves are shown in FIG. 3a. The assay sensitivity for each antibody was interpolated off each dose-response curve at the point corresponding to 50% inhibition of the epoetin alfa induced proliferation. The assay sensitivity was determined by using each antibody at a 500 ng/mL concentration, except 3A4 which was used at 333 ng/mL. The results are presented in Table 5. Antibody neutralization appeared to be associated with binding epitope and affinity, with 8C10 demonstrating the strongest neutralizing capacity and overall affinity for EPO followed by 3A4, 3F5 and 11D12. As expected, 9F7 did not demonstrate neutralizing activity since its binding epitope is outside the receptor binding sites on EPO. To confirm that the antibody framework does not impact neutralization, 8C10 IgG1, IgG2 and IgG4 antibodies were tested in the bioassay. The results in FIG. 3b demonstrate overlapping dose response curves (see FIG. 3b) and nearly identical assay sensitivity for the detection of neutralization (see Table 5). Also, the IgG2 and IgM isotype of 11D12 showed very similar neutralization (data not shown).

Cross-Reactivity with Four Commercially Available ESAs

The ability of selected antibodies from this panel to cross-react with other erythropoietin-based ESAs was assessed on the Biacore immunoassay platform. We set out to determine reactivity against Mircera®, Silapo®, Eprex® and NeoRecormon®. All ESAs tested were unmodified erythropoietin except for Mircera®, a pegylated erythropoietin. We assessed the binding of 8C10 and 3F5 because they were readily available in enough quantity for testing. The results of the binding of 8C10 and 3F5 to each of the 6 ESAs are shown in Table 6, and are expressed as the lowest antibody concentration that scored positive to each immobilized ESA. The binding of 8C10 (a neutralizing antibody that recognizes the epitope on EPO that binds with high affinity to EPO receptor) to Epogen®, Silapo®, and NeoRecormon® was sensitive down to 160 ng/mL of antibody, and required a 2-4 fold higher antibody concentration to detect binding to Eprex® and Aranesp®. A much higher concentration of 8C10, up to 1.25 µg/mL of 8C10 was required to detect binding to Mircera®. The binding of 3F5 to the various ESAs was slightly better (detected at a lower concentration) than 8C10 binding, and demonstrated more consistent binding across all ESAs. Binding data on NeoRecormon® is not reported due to insufficient test material.

TABLE 6

Antibody characterization of subcloned hybridomas. All antibodies were purified and analyzed for EPO epitope specificity in the CBA, neutralization in a bioassay and affinity to EPO determined by Biacore A100. The % neutralization represents a decrease in bioactivity using 500 ng/mL of each antibody and 1 ng/mL EPO.

| Clone | CBA confirmed Epitopes (avidin(N)-EPO variant) | EPO Bioassay % Neutralization | Biacore Affinity | | |
|---|---|---|---|---|---|
| | | | KD(pM) | ka (1/Ms) | kd (1/s) |
| 8C10 | 45 (E); 49 (F) | 73.6% | 210 | 3.6E+05 | 7.4E−05 |
| 7F1 | 49 (F) | 99.2% | 48 | 2.1E+06 | 9.7E−05 |
| 8H10 | 49 (F) | 84.3% | 181 | 3.0E+06 | 5.4E−04 |
| 10H12 | 96 (G) | 69.4% | 110 | 6.8E+04 | 7.2E−06 |
| 3F8 | 116 (S) | 7.6% | 74,400 | 8.2E+04 | 6.1E−03 |
| 9F7 | 32 (D) | 2.1% | 119,000 | 4.0E+04 | 4.7E−03 |
| 11D12 | N/A | 6.3% | 5,540 | 2.6E+04 | 1.4E−04 |
| 10B5 | N/A | 3.8% | 178,000 | 3.2E+05 | 5.8E−02 |
| 6E12 | 45 (E); 49 (F) | 13.2% | 552 | 4.3E+05 | 2.4E−04 |
| 14F5 | 49 (F) | 14.8% | 2,850 | 1.3E+06 | 3.7E−03 |
| 3F5 | 49 (F); 155 (M) | 17.6% | 50,500 | 1.0E+06 | 5.3E−02 |
| 5G1 | 45 (E) | 5.0% | 179,000 | 5.4E+05 | 9.6E−02 |
| 3A4 | 103 (I) | 32.6% | 148 | 1.8E+05 | 2.6E−05 |

TABLE 7

Cumulative characterization analysis performed on the panel of purified recombinant human antibodies including: a) verification of the isotype by Biacore method, b) identification of critical antibody-binding epitopes as determined by CBA, c) bioassay sensitivity represents the concentration of antibody that inhibits the activity of 1 ng/mL Epoetin alfa by 50% in the bioassay, d) assay sensitivity for each human antibody with an Biacore method, e) assay sensitivity for each human antibody in a bridging ECL method, and f) determination of affinity rates and affinity constant (KD).

| Clone Name | Light Chain | Biacore confirmed Isotype[a] | CBA confirmed Epitopes[b] (EPO variant) | Bioassay Sensitivity[c] (ng/mL) | Biacore Sensitivity[d] (ng/mL) | Bridging ECL Sensitivity[e] (ng/mL) | Affinity[f] | | |
|---|---|---|---|---|---|---|---|---|---|
| | | | | | | | KD (pM) | ka (1/Ms) | kd (1/s) |
| 8C10 | λ | IgG1 | 45 (E); 49 (F) | 119 | 34 | <10 | 63 | 3.7E+05 | 2.3E−05 |
| 8C10 | λ | IgG2 | 45 (E); 49 (F) | 124 | 31 | <10 | 41 | 4.0E+05 | 1.7E−05 |
| 8C10 | λ | IgG4 | 45 (E); 49 (F) | 121 | 37 | <10 | 43 | 4.2E+05 | 1.8E−05 |
| 9F7 | κ | IgM | 32 (D) | No neutralization | 54 | 1260 | 100,000 | 5.0E+04 | 4.9E−03 |
| 9F7 | κ | IgG2 | 32 (D) | No neutralization | 77 | 1260 | 121,000 | 4.1E+04 | 5.0E−03 |
| 11D12 | λ | IgM | N/A | 26300 | 272 | <10 | 3,400 | 5.3E+04 | 1.8E−04 |
| 11D12 | λ | IgG2 | N/A | 23990 | 272 | <10 | 3,610 | 3.1E+04 | 1.1E−04 |
| 3F5 | κ | IgG1 | 49 (F); 155 (M) | 8110 | 24 | >10000 | 36,800 | 1.4E+06 | 5.3E−02 |
| 3A4 | κ | IgG4 | 103 (I) | 1782 | 20 | <10 | 460 | 1.7E+05 | 7.9E−05 |

TABLE 8

The relative binding of anti-EPO neutralizing antibodies in the biosensor immunoassay against different ESAs. Results are reported as assay sensitivity in µg/mL of antibody to each ESA.

| Anti-EPO Antibody | ESA | | | | | |
|---|---|---|---|---|---|---|
| | Silapo | Eprex | Micera | NeoRecormon (in µg/mL) | Epogen | Aranesp |
| 8C10 | 0.16 | 0.31 | 1.25 | 0.16 | 0.16 | 0.44 |
| 3F5 | 0.16 | 0.16 | 0.31 | NA | 0.08 | 0.31 |
| 3A4 | 0.08 | NA | 0.625 | 0.16 | 0.03 | 0.06 |
| 11D12, IgG2 | 0.08 | NA | 0.625 | 0.16 | 0.1 | 0.31 |
| 9F7, IgM | 1.25 | NA | 10.0 | 0.625 | 0.625 | No binding |

TABLE 9

Isotype prevalence observed in Nephrology, Oncology, and Congestive Heart Failure (CHF) clinical studies; includes both baseline and post-treatment samples. Anti-EPO IgM and IgG1 antibodies are most commonly detected in study samples with infrequent IgG2 and IgG3 detection. IgG4 anti-EPO antibodies have not been detected in these study populations.

| Study Population | Subjects (N) | Isotype Prevalence (%) | | | | |
|---|---|---|---|---|---|---|
| | | IgM | IgG1 | IgG2 | IgG3 | IgG4 |
| Nephrology | 1235 | 1.21 | 0.40 | 0.00 | 0.00 | 0.00 |
| Oncology | 5051 | 0.77 | 0.30 | 0.02 | 0.04 | 0.00 |
| CHF | 584 | 0.51 | 0.68 | 0.00 | 0.00 | 0.00 |

Example 10

The Measurement of Anti-ESA IgG4 Antibody as an Indicator of Antibody-Mediated PRCA Background:

Patients treated with erythropoiesis stimulating agents (ESAs) can develop a rare but life-threatening condition called antibody-mediated pure red cell aplasia (amPRCA). The antibody characteristics in a nephrology patient with amPRCA include high antibody concentrations with neutralizing activity, and a mixed IgG subclass including anti-ESA IgG4 antibodies. In contrast, anti-ESA IgG4 antibody is generally not detected in baseline samples and antibody-positive non-PRCA patients. This suggests that antibody maturation including the IgG4 isotype switch is characteristic of a mature, adaptive immune response to the ESA. Therefore, we developed and validated a highly sensitive immunoassay using the ImmunoCAP® 100 instrument to detect anti-ESA IgG4 antibodies.

Methods:

A novel immunoassay was validated on an Immuno-CAP® 100 instrument to detect anti-ESA IgG4 antibodies in human serum using a human recombinant anti-Epoetin alfa (EPO) IgG4 antibody as a calibrator. The biotinylated ESA drug was coated on a streptavidin ImmunoCAP and bound anti-ESA IgG4 antibodies were detected using a beta galactosidase-conjugated mouse anti-human IgG4 antibody. Assay validation included assay sensitivity, specificity, and anti-ESA IgG4 detection in the presence of excess anti-ESA IgG1 and IgG2 subclass antibodies. The validated assay was used to detect anti-ESA IgG4 in amPRCA and non-PRCA patients.

Results:

The anti-ESA IgG4 antibody immunoassay detected 15 ng/mL of human anti-EPO IgG4 antibody in the presence of a 200-molar excess of human anti-ESA IgG1, IgG2, or IgM antibody and tolerated 2 µg/mL of soluble erythropoietin. All patient samples with confirmed amPRCA had measurable anti-ESA IgG4 antibodies. In addition, 94% (17/18) of non-PRCA patient samples were antibody negative or below 15 ng/mL of anti-ESA IgG4 antibodies.

Conclusions:

We have validated a novel immunoassay that can measure low nanogram concentrations of human anti-ESA IgG4 antibodies in the presence of excess anti-ESA IgG1, IgG2 and IgM antibodies. Increased concentration of anti-ESA IgG4 antibody is associated with the development of amPRCA. The measurement of anti-ESA specific IgG4 antibodies can facilitate early detection of amPRCA in patients receiving ESAs.

Materials and Methods

Sample Selection and Classification

Sixty normal human serum samples and pooled normal human serum (PNHS) were obtained from Bioreclamation (Hicksville, N.Y.) for assay validation. A total of 25 human serum samples were compiled from clinical studies (n=6) and post-marketed safety samples from patients treated with an ESA (n=19), of which 8 patient samples from the post-market setting were classified as amPRCA. All specimens from patients treated with an ESA were provided by Amgen Inc. (Thousand Oaks, Calif.). Patients were classified into two groups: amPRCA and non-PRCA. Patients positive at one or more time point for neutralizing antibodies were classified as amPRCA. Patients that had received and responded to ESA treatment, tested antibody positive in the immunoassay but negative throughout ESA treatment for neutralizing antibodies were classified as non-PRCA. All patients provided consent to Amgen, Inc. for serum sample collection and testing for anti-ESA antibodies.

ImmunoCAP® 100 Method

The anti-ESA IgG4 antibodies were measured using the ImmunoCAP® 100 (Phadia AB, Uppsala, Sweden). In this method, streptavidin conjugated ImmunoCAPs (Cat # R0121) were coated with 50 µL of 10 µg/mL biotinylated Epoetin alfa (Amgen, Thousand Oaks, Calif.). The addition of biotinylated Epoetin alfa (EPO) and subsequent incubations and washing steps were performed on the instrument by manual instrument programming instructions. The test serum samples were diluted 1:10 using sample diluent (Cat #10-9498-0), incubated for 1 hour, washed with Phadia washing solution (Cat #10-9422-01), and then β-galactosidase conjugated anti-human IgG4 specific conjugate (Cat #10-9465-02) was added to each ImmunoCAP®. The reaction was incubated for 1 hour, washed and then development solution (cat#10-9478-01) was added and incubated for 1 hour Finally, a stop solution (cat#10-9479-01) was added to each ImmunoCAP® and the chemilumenescence was read by the instrument and reported in response units. The human IgG4 concentration of the test samples were extrapolated from the calibrator curve using the Graph Pad Prism 5.0 software.

Human Antibody Calibrator

A panel of recombinant human anti-ESA antibodies were developed by Amgen (Thousand Oaks, Calif.) and used in the validation. The recombinant human antibodies included 8C10 IgG1 (8C10G1), 8C10 IgG2 (8C10G2), 8C10 IgG4 (8C10G4) and 11D12 monomeric IgM. The human anti-ESA antibody 8C10G4 was used as the calibrator to generate the standard curve and QC standards in the assay.

Validation of the ImmunoCAP® 100 Assay

Assay validation parameters followed published recommendations for anti-drug antibody immunoassays [Mire-Sluis A R, Barrett Y C, Devanarayan V, et al. Recommendations for the design and optimization of immunoassays used in the detection of host antibodies against biotechnology products. J Immunol Methods 2004; 289(1-2):1-16].

Assay Cut Point

A total of 60 normal human serum samples were tested in duplicate to generate the assay cut point (ACP). The ACP was established by calculating the upper bound of a one-sided 95% reference interval for the distribution of donor Response Units (Mean RU+1.645 standard deviation).

Sensitivity and Precision

The anti-ESA IgG4 antibody standard curve was analyzed over multiple days. The data from thirteen individual dose-response curves ranging from 100 to 0.005 µg/mL concentrations were analyzed using a 4-parameter logistic non-linear regression model in Graph Pad Prism v. 5.0, generating the mean dose-response curve. Intersection of the curve at the ACP value yielded assay sensitivity. The precision of each concentration on the curve was then calculated as a percent coefficient of variation (CV).

Lower Limit of Reliable Detection (LLRD)

Pilot LLRD experiments were performed by spiking human anti-ESA IgG4 antibody into 6 individual human serum samples at various concentrations to determine the recovery above the ACP. Based on the pilot experiment, a more rigorous spiking experiment was then performed with 30 individual serum samples to confirm 100% recovery above the ACP.

Specificity

A range of anti-ESA specific antibody isotypes can be present in a patient sample. To replicate what may be found in an antibody-positive patient, 5 µg/mL of anti-ESA antibody of each antibody 8C10G1, 8C10G2, and 11D12 IgM or a cocktail of the three antibodies were spiked into PNHS containing 0, 15, 50, and 200 ng/mL of specific human anti-ESA antibody 8C10G4.

Drug Tolerance

The ESA dose administered to patients can vary and high serum levels can interfere with the measurement of the anti-ESA IgG4 antibodies. Therefore, the method was evaluated to detect anti-ESA IgG4 antibody in the presence of soluble ESA drug. PNHS was spiked with 250 ng/mL and 15 ng/mL of human anti-ESA 8C10G4 antibody in the presence of varying concentrations of ESA.

Statistical Analysis

The Wilcoxon two-sample Exact Test was applied to compare the anti-IgG4 concentrations between amPRCA and non-PRCA. Since this is a non-parametric test, the p-value for this test was reported and the magnitude of the difference and the confidence interval of the difference were not reported.

Results

Validation Performance

Figure 5:
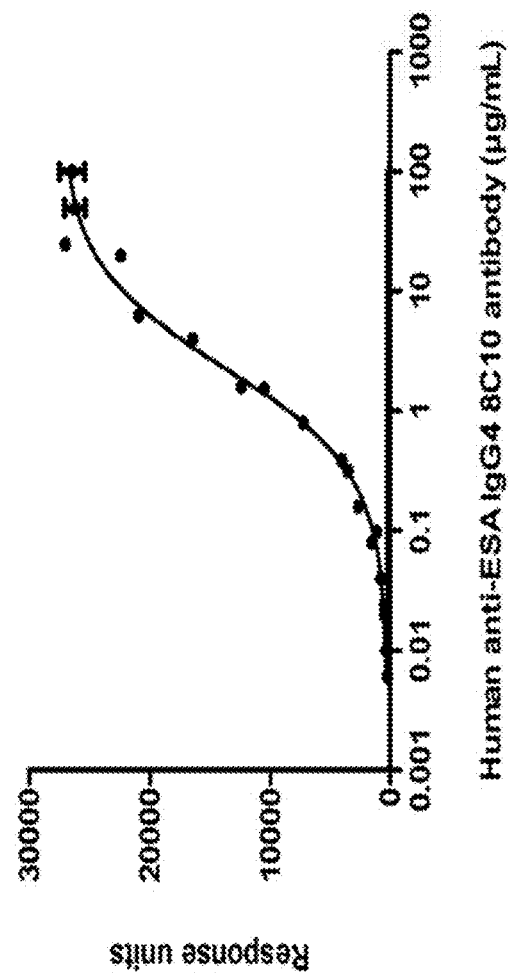
FIG. 5. This graph represents the signal (in response units) on the y-axis relative to the PNHS spiked with 0.0025 to 100 µg/mL of human anti-ESA antibody 8C10G4. A total of 13 curves were analyzed in duplicate. The solid thick line represents the ACP at 243.75 which intersections at 7 ng/mL of anti-EPO IgG4 antibody. The graph was constructed using a 4-parameter logistic non-linear regression model in Graph Pad Prism v. 5.0. The response unit per concentration is reported with the standard error mean (SEM).
Figure 6:
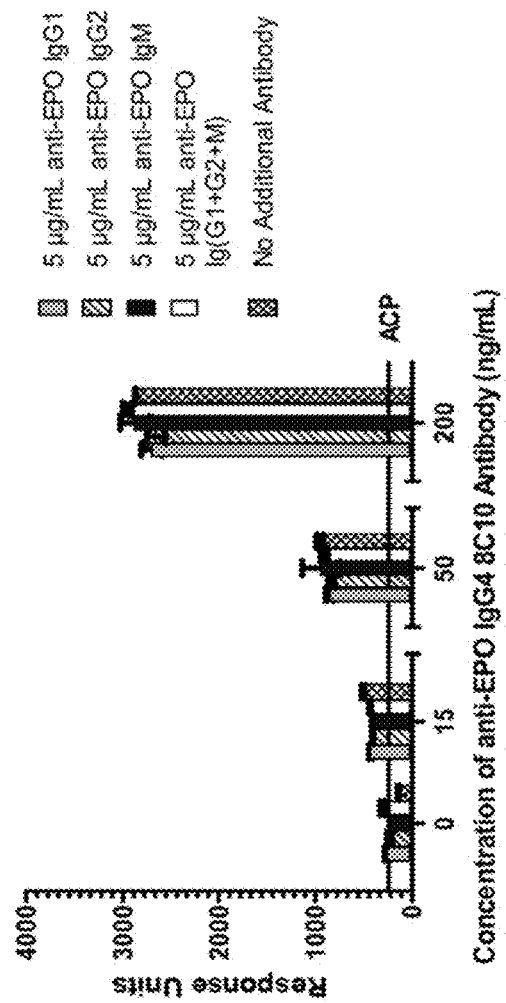
FIG. 6. The graphical representation of the measurement of 0, 15, 50 and 200 ng/mL of human antibody 8C10G4 in the presence of 5 µg/mL of anti-ESA antibodies IgG1, IgG2, and IgM as well as a cocktail containing 5 µg/mL each of IgG1, IgG2 and IgM.
Figure 7:
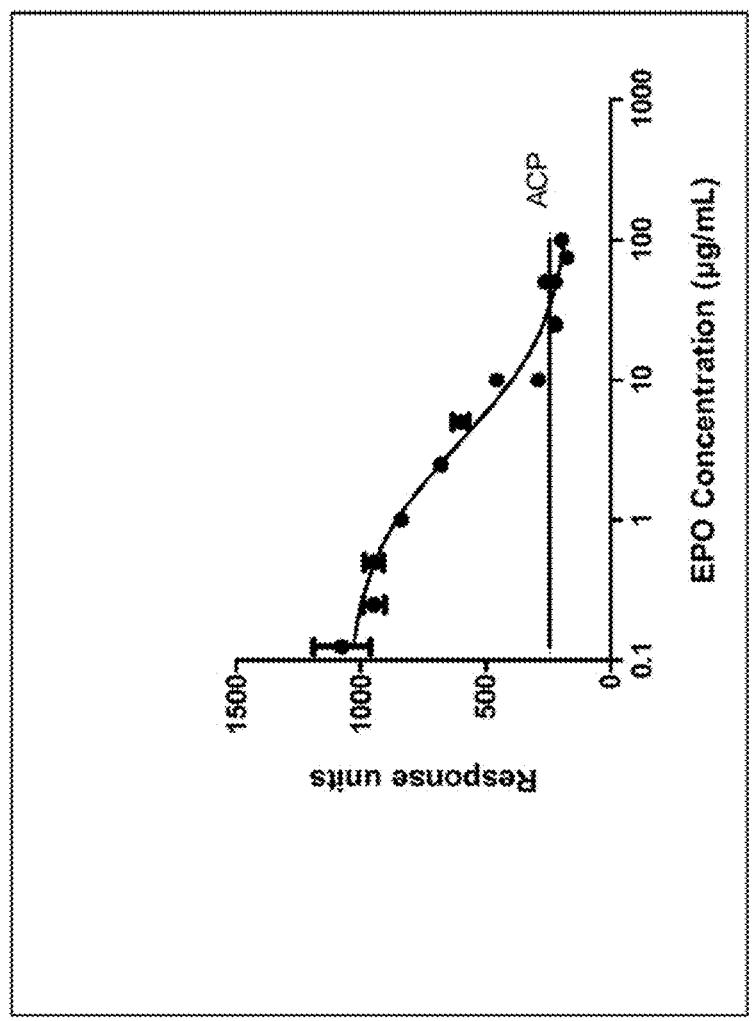
FIG. 7. Pooled Normal Human Serum samples containing 250 ng/mL of human anti-ESA antibody 8C10G4 spiked with 0 to 100 µg/mL of Epoetin alfa. The response unit readout is displayed on the Y-axis and the concentration of Epoetin alfa (in µg/mL) is displayed on a logarithmic scale on the X-axis. The solid line indicates the ACP (243.75).

During assay validation, there were three key parameters critical to assess the feasibility of this assay: adequate sensitivity, the ability to measure the specific anti-ESA IgG4 in the presence of other anti-ESA specific isotypes, and tolerance to soluble ESA. To determine these parameters, the ACP was first established. Based on 60 human samples, the mean ACP plus 1.645 standard deviations was calculated to be 243.75 response units. The human anti-ESA IgG4 antibody calibrator 8C10G4 was then spiked into PNHS from 100 to 0.005 µg/mL of anti-ESA IgG4 antibody and assayed in duplicate on 13 different days. A plot of the human 8C10G4 antibody concentration against response unit is shown in FIG. 5. At each antibody concentration on the curve, precision was less than 25% CV (data not shown). The assay sensitivity, based on the antibody concentration intersecting the ACP, was determined to be 7 ng/mL of 8C10G4. At a spiked concentration of 15 ng/mL of human antibody 8C10G4 in 30 individual serum samples, all 30 spiked samples recovered above the ACP, confirming that the assay can reliably detect 15 ng/mL of anti-ESA IgG4 antibodies (data not shown). Since the antibody characteristics observed in patients with amPRCA present with a mixed IgG subclass response, the measurement of ESA-specific IgG4 antibody in the presence of excess ESA-specific IgG1, IgG2 and IgM antibody was confirmed. The data presented in FIG. 6 shows that despite the presence of the excess of other anti-ESA specific antibodies, the assay is capable of detecting 15 ng/mL of anti-ESA IgG4 antibody, even in the presence of a 5 µg/mL of each of the ESA-specific IgG1, IgG2, and IgM mixed isotype. Therefore, the assay is highly specific and sensitive Finally, soluble ESA in the serum sample can interfere with antibody detection. As shown in FIG. 7, we have demonstrated that 250 ng/mL of human antibody 8C10G4 can be detected in the presence of 25 µg/mL of excess ESA. Validation experiments also demonstrated the reproducible detection of 15 ng/mL of human antibody 8C10G4 in the presence of 2 µg/mL of soluble drug (data not shown).

To evaluate the ImmunoCAP® 100 assay capability of detecting anti-ESA IgG4 antibody in the clinical patient population, a subset of serum samples previously tested and characterized in the SPRIA were analyzed using the ImmunoCAP® 100 assay. The results from both methods are reported in Table 1. Eight patient samples had confirmed amPRCA. Six of 6 patient samples (100%) classified as amPRCA had a confirmed anti-ESA IgG4 antibody in the SPRIA and also had measurable anti-ESA IgG4 antibody in the ImmunoCAP® 100 assays, with the lowest concentration measured at 89 ng/mL of anti-ESA IgG antibody. In addition, one amPRCA patient without a confirmed isotype by SPRIA had 59 ng/mL of anti-ESA IgG4 antibody by ImmunoCAP® 100 (sample 16); one amPRCA patient with a confirmed anti-ESA IgG1 antibody by SPRIA (sample 17) did not have measurable anti-ESA IgG4. In the non-PRCA patient population, all 17 patient samples tested anti-ESA IgG4 negative except one (sample 18) which scored IgG1 positive by SPRIA but had a low level anti-ESA IgG4 antibody (18 ng/mL) by the ImmunoCAP® 100 assay. Despite the low level of measurable IgG4 in this one sample from the non-PRCA patient samples, statistical analysis of the median anti-ESA IgG4 antibody concentration between the non-PRCA and amPRCA patient population resulted in a statistically significant (P-value <0.0001) difference (see FIG. 8).

Discussion

This experiment details the development of a highly sensitive and specific immunoassay for the measurement of anti-ESA IgG4 antibodies using the ImmunoCAP® technology. We have utilized this technology to develop a sensitive and specific immunoassay to measure the anti-ESA IgG4 antibody in patients administered an ESA.

The diagnosis of amPRCA, although rare, has been characterized by the development of high anti-ESA antibody concentration with neutralizing capacity and a mixed IgG subclass, including IgG4. Despite this knowledge, longitudinal sampling from the early onset up to months prior to amPRCA has not been well documented. In the post-market setting, samples are collected and sent for anti-ESA antibody testing after other causes of PRCA have been ruled out, resulting in a gap in our understanding of the time course between onset and full-blown amPRCA.

The analysis of patient samples that tested antibody-positive in the SPRIA from amPRCA and non-PRCA were of most interest. We have previously shown that there is a strong statistical correlation between the anti-ESA antibody concentration and patients with amPRCA [Barger T E, Kuck A J, Chirmule N, et al. Detection of anti-ESA antibodies in human samples from PRCA and non-PRCA patients: an immunoassay platform comparison. Nephrol Dial Transplant 2012; 27(2):688-693] and the presence of anti-ESA IgG4 and anti-ESA neutralizing antibody activity in amPRCA patients [Barger T, Wrona D, Goletz T, Mytych D T. A detailed examination of the antibody prevalence and characteristics of anti-ESA antibodies. Nephrol Dial Transplant (in press)].

Here, we have demonstrated a strong correlation between the anti-ESA IgG4 antibody concentration and patients with amPRCA. The data presented here demonstrates that using the ImmunoCAP® technology, we can measure the concentration of anti-ESA specific IgG4 antibodies in a serum sample. Utilizing a human anti-ESA IgG4 antibody 8C10G4 as a calibrator, the quantitation of the anti-ESA specific antibody in a serum sample can measure 15 ng/mL of anti-ESA IgG4 antibody. All samples that showed binding below the 15 ng/mL concentration are anti-ESA IgG4 negative. We believe that the high surface capacity of the streptavidin ImmunoCAP® coated with biotinylated Epoetin alfa provides low nanogram sensitivity to measure anti-ESA IgG4 antibody in the presence of a 200 molar excess of ESA-specific IgG1 and IgG2 antibodies. This large surface binding capacity also allows for the detection of 15 ng/mL of anti-ESA IgG4 antibody in the presence of 2 µg/mL of excess soluble ESA.

The ImmunoCAP® 100 assay proved more sensitive than the SPRIA, detecting more anti-ESA IgG4 antibody in both patient populations. In the amPRCA population (N=8), 6 patient samples with detectable IgG4 by SPRIA all had measurable anti-ESA IgG4 greater than or equal to 89 ng/mL. In addition, anti-ESA IgG4 antibody was measured in a patient sample (sample 16) with confirmed amPRCA but no confirmed isotype by SPRIA. Based on the low antibody concentration in the SPRIA assay, this was not unexpected due to the lack of sensitivity around the SPRIA isotype confirmation assay and the high specificity and sensitivity of the ImmunoCAP® assay. One additional patient sample (sample 17) with a confirmed amPRCA demonstrated high antibody concentration by SPRIA and a confirmed anti-ESA IgG1 antibody. The analysis for anti-ESA IgG4 antibody was negative. An investigation of the patient history revealed that this patient was treated with an ESA for the correction of anemia associated with ribavirin and pegylated interferon alfa 2B treatment for an HCV infection. The prevalence of amPRCA in this patient population has been reported recently in the literature [Miura Y, Kami M, Yotsuya R, et al. Pure red-cell aplasia associated with pegylated interferon-alpha-2b plus ribavirin. CORD Conference Proceedings 2008; 83(9):758-759]. There appears to be a predominance of anti-ESA IgG1 antibody and a lack of IgG4 observed in this patient population (personal communication). Therefore, the measurement of anti-ESA IgG4 in this patient population may be different than what has been observed in the nephrology setting.

All non-PRCA patient samples that were antibody-negative (N=8) and antibody-positive (N=17) by SPRIA (see Table 1) also scored negative for anti-ESA IgG4 antibody in the ImmunoCAP® 100 assay except one patient sample (sample 18). This sample was borderline positive for anti-ESA IgG4, just above the 15 ng/mL assay limit. It would have been interesting to repeat the analysis to confirm the reproducibility of the analysis but additional sample volume was not available. In spite of the predominant IgG1 detected by the SPRIA, this patient received an ESA for chronic kidney disease and did not exhibit a reduced response to the ESA treatment.

The long-term administration of an ESA can result in a rare but life-threatening condition called antibody-mediated pure red cell aplasia. With the utilization of the ImmunoCAP technology, we have shown that the anti-ESA IgG4 antibody concentration is associated with amPRCA. With the availability of a human anti-ESA IgG4 antibody as a calibrator, we have developed an immunoassay with wide dynamic range and assay sensitivity down to 15 ng/mL of anti-ESA specific IgG4 antibody in human serum. Since the total and drug-specific IgG4 antibody is a minor component of the total IgG concentration, achieving reproducible measurement of anti-ESA IgG4 in the presence of more prevalent anti-ESA specific IgG1 and IgG2 antibody as well as soluble ESA was required. Most importantly, the lack of anti-ESA IgG4 antibody in non-PRCA clinical patient population and the measurement of IgG4 greater than 89 ng/mL in the amPRCA population were encouraging.

Table 1

This table summarizes results from the SPRIA, ImmunoCAP® 100 anti-ESA IgG4 assays, and a cell based assay for neutralizing antibodies. All patient samples that had an anti-ESA concentration greater than the 250 ng/mL by SPRIA were further characterized for isotype (IgG1, IgG2, IgG3, IgG4, and IgM) as well as tested by a cell based bioassay to determine if neutralizing antibodies were present. All patient samples were tested in the ImmunoCAP anti-ESA IgG4 assay. All samples that that had less than 15 ng/mL of anti-ESA IgG4 were reported as "Negative". * Patient tested anti-ESA IgG4 antibody positive at a subsequent time point.

TABLE 1

| Sample ID | SPRIA Results | SPRIA Isotype | Anti-ESA Ab [ng/mL] | ImmunoCAP® Results | Anti-ESA IgG4 Ab [ng/mL] | Patient Classification based on Nab Assay |
|---|---|---|---|---|---|---|
| 1 | Positive | IgG1, IgG2, IgG3, IgG4 | >10,000 | Positive | 145 ng/mL | amPRCA |
| 2 | Negative | — | — | Negative | NA | Non-PRCA |
| 3 | Positive | IgG1, IgG2, IgG4 | 6030 | Positive | 89 ng/mL | amPRCA |
| 4 | Positive | IgG1, IgG2, IgG4 | 620 | Positive | 89 ng/mL | amPRCA |
| 5 | Positive | IgG1, IgG2, IgG3, IgG4 | >10,000 | Positive | 669 ng/mL | amPRCA |
| 6 | Negative | — | — | Negative | NA | Non-PRCA |
| 7 | Positive | IgG1 | 600 | Negative | NA | Non-PRCA |
| 8 | Positive | IgG1, (IgG4*) | 1730 | Positive | 95 ng/mL | amPRCA |
| 9 | Negative | — | — | Negative | NA | Non-PRCA |
| 10 | Negative | — | — | Negative | NA | Non-PRCA |
| 11 | Negative | — | — | Negative | NA | Non-PRCA |
| 12 | Negative | — | — | Negative | NA | Non-PRCA |
| 13 | Positive | Unable to determine | 340 | Negative | NA | Non-PRCA |
| 14 | Negative | — | — | Negative | NA | Non-PRCA |
| 15 | Negative | — | — | Negative | NA | Non-PRCA |
| 16 | Positive | Unable to determine | 520 | Positive | 59 ng/mL | amPRCA |
| 17 | Positive | IgG1 | 6660 | Negative | NA | amPRCA |
| 18 | Positive | IgG1 | 840 | Positive | 18 ng/mL | Non-PRCA |
| 19 | Positive | IgG1 | 3690 | Negative | NA | Non-PRCA |
| 20 | Positive | IgM | 920 | Negative | NA | Non-PRCA |
| 21 | Positive | IgG1 | 1210 | Negative | NA | Non-PRCA |
| 22 | Positive | IgM | 1.94 | Negative | NA | Non-PRCA |
| 23 | Positive | IgG3 | 700 | Negative | NA | Non-PRCA |
| 24 | Positive | IgG1 | 0.93 | Negative | NA | Non-PRCA |
| 25 | Positive | IgG1, IgG2, IgG3, IgG4 | >10.000 | Positive | 4978 ng/mL | amPRCA |

Antibody Sequences

8C10 LC
Full amino Acid sequence
MDMRVPAQLLGLLLLWLRGARCSYVLTQPPSVSVAPGQTARITCGGNNIG

SKSVHWYQQKPGQAPVLVVYDDSDRPSGIPERFSGSNSGNTATLTISWVE

AGDEADYYCQVWDSSGDHPVFGGGTKLTVLGQPKANPTVTLFPPSSEELQ

ANKATLVCLISDFYPGAVTVAWKADGSPVKAGVETTKPSKQSNNKYAASS

YLSLTPEQWKSHRSYSCQVTHEGSTVEKTVAPTECS*

DNA sequence
atggacatgagggtgcccgctcagctcctggggctcctgctgctgtggct gagaggtgcgcgctgttcctatgtgctgactcagccaccctcggtgtcag tggccccaggacagacggccaggattacctgtggggaaacaacattgga agtaaaagtgtgcactggtaccagcagaagccaggccaggcccctgtgct ggtcgtctatgatgatagcgaccggccctcagggatccctgagcgattct ctggctccaactctgggaacacggccaccctgaccatcagctgggtcgaa gccggggatgaggccgactattactgtcaggtgtgggatagtagtggtga tcatccggtattcggcggagggaccaagctgaccgtcctaggtcagccca aggccaaccccactgtcactctgttccgcccctcctctgaggagctccaa gccaacaaggccacactagtgtgtctgatcagtgacttctacccgggagc tgtgacagtggcctggaaggcagatggcagccccgtcaaggcgggagtgg agaccaccaaaccctccaaacagagcaacaacaagtacgcggccagcagc tacctgagcctgacgcccgagcagtggaagtcccacagaagctacagctg ccaggtcacgcatgaagggagcaccgtggagaagacagtggcccctacag aatgttcatga 8C10 HC IgG1
Full Amino Acid Sequence
MDMRVPAQLLGLLLLWLRGARCQVQLQQSGPGLVKPSQTLSLTCAISGDS

VSSNSAAWNWIRQSPSRGLEWLGRTYYRSKWYNDYEVSVKSRIIINPDTS

KNQFSLQLNSVTPEDTAVYYCAREEGYIEAHSVPYFDYWGQGTLVTVSSA

STKGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKKVEPK

SCDKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLTCL

VKGFYPSDIAVEWESNGQPENNYKTTPPVLDSDGSFFLYSKLTVDKSRWQ

QGNVFSCSVMHEALHNHYTQKSLSLSPGK

DNA Sequence
atggacatgagggtgcccgctcagctcctggggctcctgctgctgtggct gagaggtgcgcgctgtcaggtacagctgcagcagtcaggtccaggactgg tgaagccctcgcagaccctctcactcacctgtgccatctccggggacagt gtctctagcaacagtgctgcttggaactggatcaggcagtccccatcgag aggccttgagtggctgggaaggacatactacaggtccaagtggtataatg attatgaagtatctgtgaaaagtcgaataatcatcaacccagacacatcc aagaaccagttctccctgcagctgaactctgtgactcccgaggacacggc tgtgtattactgtgcaagggaggaggggtatatagaagcccactcggttc cttactttgactactggggccagggaaccctggtcaccgtctctagtgcc -continued tccaccaagggcccatcggtcttccccctggcaccctcctccaagagcac ctctgggggcacagcggccctgggctgcctggtcaaggactacttccccg aaccggtgacggtgtcgtggaactcaggcgccctgaccagcggcgtgcac accttcccggctgtcctacagtcctcaggactctactccctcagcagcgt ggtgaccgtgccctccagcagcttgggcacccagacctacatctgcaacg tgaatcacaagcccagcaacaccaaggtggacaagaaagttgagcccaaa tcttgtgacaaaactcacacatgcccaccgtgcccagcacctgaactcct gggggaccgtcagtcttcctcttccccccaaaacccaaggacaccctca tgatctcccggacccctgaggtcacatgcgtggtggtggacgtgagccac gaagaccctgaggtcaagttcaactggtacgtggacggcgtggaggtgca taatgccaagacaaagccgcgggaggagcagtacaacagcacgtaccgtg tggtcagcgtcctcaccgtcctgcaccaggactggctgaatggcaaggag tacaagtgcaaggtctccaacaaagccctcccagcccccatcgagaaaac catctccaaagccaaagggcagccccgagaaccacaggtgtacaccctgc ccccatcccgggaggagatgaccaagaaccaggtcagcctgacctgcctg gtcaaaggcttctatcccagcgacatcgccgtggagtgggagagcaatgg gcagccggagaacaactacaagaccacgcctcccgtgctggactccgacg gctccttcttcctctatagcaagctcaccgtggacaagagcaggtggcag caggggaacgtcttctcatgctccgtgatgcatgaggctctgcacaacca ctacacgcagaagagcctctccctgtctccgggtaaatga 8C10 HC IgG2
Full Amino Acid Sequence
MDMRVPAQLLGLLLLWLRGARCQVQLQQSGPGLVKPSQTLSLTCAISGDS

VSSNSAAWNWIRQSPSRGLEWLGRTYYRSKWYNDYEVSVKSRIIINPDTS

KNQFSLQLNSVTPEDTAVYYCAREEGYIEAHSVPYFDYWGQGTLVTVSSA

STKGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKKVEPK

SCDKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLTCL

VKGFYPSDIAVEWESNGQPENNYKTTPPVLDSDGSFFLYSKLTVDKSRWQ

QGNVFSCSVMHEALHNHYTQKSLSLSPGK

DNA Sequence
atggacatgagggtgcccgctcagctcctggggctcctgctgctgtggct gagaggtgcgcgctgtcaggtacagctgcagcagtcaggtccaggactgg tgaagccctcgcagaccctctcactcacctgtgccatctccggggacagt gtctctagcaacagtgctgcttggaactggatcaggcagtccccatcgag aggccttgagtggctgggaaggacatactacaggtcaagtggtataatg attatgaagtatctgtgaaaagtcgaataatcatcaacccagacacatcc aagaaccagttctccctgcagctgaactctgtgactcccgaggacacggc 8C10 LC Native leader, IgG4
Full Amino Acid Sequence
MAWITLLLLGLLSHCTDSVTSYVLTQPPSVSVAPGQTARITCGGNNIGSKS

VHWYQQKPGQAPVLVVYDDSDRPSGIPERFSGSNSGNTATLTISWVEAGD

EADYYCQVWDSSGDHPVFGGGTKLTVLGQPKAAPSVTLFPPSSEELQANK

ATLVCLISDFYPGAVTVAWKADSSPVKAGVETTTPSKQSNNKYAASSYLS

LTPEQWKSHRSYSCQVTHEGSTVEKTVAPTECS

DNA Sequence
atggcatggatcactctcctcctcggcctcctctctcactgcacagactc tgtgacctcctatgtgctgactcagccaccctcggtgtcagtggccccag gacagacggccaggattacctgtgggggaaacaacattggaagtaaaagt gtgcactggtaccagcagaagccaggccaggcccctgtgctggtcgtcta tgatgatagcgaccggccctcagggatccctgagcgattctctggctcca actctgggaacacggccaccctgaccatcagctgggtcgaagcggggat gaggccgactattactgtcaggtgtgggatagtagtggtgatcatccggt attcggcggagggaccaagctgaccgtcctaggtcagcccaaggctgccc cctcggtcactctgttccctccctctagcgaggagcttcaagccaacaag gccacactggtgtgtctcataagtgacttctacccgggagccgtgacagt ggcctggaaggcagatagcagccccgtcaaggcgggagtggagaccacca cacccctccaaacaaagcaacaacaagtacgcggccagcagctatctgagc 8C10 HC IgG4
Full Amino Acid Sequence
MSVSFLIFLPVLGLPWGVLSQVQLQQSGPGLVKPSQTLSLTCAISGDSVS
SNSAAWNWIRQSPSRGLEWLGRTYYRSKWYNDYEVSVKSRIIINPDTSKN
QFSLQLNSVTPEDTAVYYCAREEGYIEAHSVPYFDYWGQGTLVTVSSAST
KGPSVFPLAPCSRSTSESTAALGCLVKDYFPEPVTVSWNSGALTSGVHTF
PAVLQSSGLYSLSSVVTVPSSSLGTKTYTCNVDHKPSNTKVDKRVESKYG
PPCPSCPAPEFLGGPSVFLFPPKPKDTLMISRTPEVTCVVVDVSQEDPEV
QFNWYVDGVEVHNAKTKPREEQFNSTYRVVSVLTVLHQDWLNGKEYKCKV
SNKGLPSSIEKTISKAKGQPREPQVYTLPPSQEEMTKNQVSLTCLVKGFY
PSDIAVEWESNGQPENNYKTTPPVLDSDGSFFLYSRLTVDKSRWQEGNVF
SCSVMHEALHNHYTQKSLSLSLGK DNA Sequence
atgtctgtctccttcctcatcttcctgcccgtgctgggcctcccatgggg
tgtcctgtcacaggtacagctgcagcagtcaggtccaggactggtgaagc
cctcgcagaccctctcactcacctgtgccatctccggggacagtgtctct
agcaacagtgctgcttggaactggatcaggcagtcccccatcgagaggcct
tgagtggctgggaaggacatactacaggtccaagtggtataatgattatg
aagtatctgtgaaaagtcgaataatcatcaacccagacacatccaagaac
cagttctccctgcagctgaactctgtgactcccgaggacacggctgtgta
ttactgtgcaagggaggaggggtatatagaagcccactcggttccttact
ttgactactggggccagggaaccctggtcaccgtctcctcagcttccacc
aagggcccatccgtcttccccctggcgccctgctctagaagcacctccga
gagcacagccgccctgggctgcctggtcaaggactacttccccgaaccgg
tgacggtgtcgtggaactcaggcgccctgaccagcggcgtgcacaccttc
ccggctgtcctacagtcctcaggactctactccctcagcagcgtggtgac
cgtgccctccagcagcttgggcacgaagacctacacctgcaacgtagatc
acaagcccagcaacaccaaggtggacaagagagttggtgagaggccagca
cagggagggagggtgtctgctggaagccaggctcagccctcctgcctgga
cgcaccccggctgtgcagcccagcccagggcagcaaggcatgccccatc
tgtctcctcacccggaggcctctgaccacccactcatgctcagggagag
ggtcttctggattttccaccaggctccgggcagccacaggctggatgcc
cctaccccaggccctgcgcatacaggggcaggtgctgcgctcagacctgc
caagagccatatccggggaggacctgcccctgacctaagcccaccccaaa
ggccaaactctccactccctcagctcagacaccttctctcctcccagatc
tgagtaactcccaatcttctctctgcagagtccaaatatggtcccccatg
cccatcatgcccaggtaagccaacccaggcctcgccctccagctcaaggc
gggacaggtgccctagagtagcctgcatccagggacaggccccagccggg gtgctgacgcatccacctccatctcttcctcagcacctgagttcctgggg
ggaccatcagtcttcctgttccccccaaaacccaaggacactctcatgat
ctcccggacccctgaggtcacgtgcgtggtggtggacgtgagccaggaag
accccgaggtccagttcaactggtacgtggatggcgtggaggtgcataat
gccaagacaaagccgcgggaggagcagttcaacagcacgtaccgtgtggt
cagcgtcctcaccgtcctgcaccaggactggctgaacggcaaggagtaca
agtgcaaggtctccaacaaaggcctcccgtcctccatcgagaaaaccatc
tccaaagccaaaggtgggacccacggggtgcgagggccacacggacagag
gccagctcggcccaccctctgccctgggagtgaccgctgtgccaacctct
gtcctacagggcagccccgagagccacaggtgtacaccctgcccccatc
ccaggaggagatgaccaagaaccaggtcagcctgacctgcctggtcaaag
gcttctaccccagcgacatcgccgtggagtgggagagcaatgggcagccg
gagaacaactacaagaccacgcctcccgtgctggactccgacggctcctt
cttcctctacagcaggctaaccgtggacaagagcaggtggcaggaggga
atgtcttctcatgctccgtgatgcatgaggctctgcacaaccactacaca
cagaagagcctctccctgtctctgggtaaatga 8C10 LC IgG4 native leader and intronless G4
Full Amino Acid Sequence
MAWITLLLGLLSHCTDSVTSYVLTQPPSVSVAPGQTARITCGGNNIGSKS
VHWYQQKPGQAPVLVVYDDSDRPSGIPERFSGSNSGNTATLTISWVEAGD
EADYYCQVWDSSGDHPVFGGGTKLTVLGQPKAAPSVTLFPPSSEELQANK
ATLVCLISDFYPGAVTVAWKADSSPVKAGVETTTPSKQSNNKYAASSYLS
LTPEQWKSHRSYSCQVTHEGSTVEKTVAPTECS DNA Sequence
atggcatggatcactctcctcctcggcctcctctctcactgcacagactc
tgtgacctcctatgtgctgactcagccacccctcggtgtcagtggccccag
gacagacggccaggattacctgtgggggaaacaacattggaagtaaaagt
gtgcactggtaccagcagaagccaggccaggcccctgtgctggtcgtcta
tgatgatagcgaccggccctcagggatccctgagcgattctctggctcca
actctgggaacacggccaccctgaccatcagctgggtcgaagccggggat
gaggccgactattactgtcaggtgtgggatagtagtggtgatcatccggt
attcggcggagggaccaagctgaccgtcctaggtcagcccaaggctgccc
cctcggtcactctgttccctccctctagcgaggagcttcaagccaacaag
gccacactggtgtgtctcataagtgacttctaccgggagccgtgacagt
ggcctggaaggcagatagcagccccgtcaaggcgggagtggagaccacca
caccctccaaacaaagcaacaacaagtacgcggccagcagctatctgagc
ctgacgcctgagcagtggaagtcccacagaagctacagctgccaggtcac
gcatgaagggagcaccgtggagaagacagtggcccctacagaatgttcat
ag 8C10 HC IgG4 native leader and intronless G4
Full Amino Acid Sequence
MSVSFLIFLPVLGLPWGVLSQVQLQQSGPGLVKPSQTLSLTCAISGDSVS

```
SNSAAWNWIRQSPSRGLEWLGRTYYRSKWYNDYEVSVKSRIIINPDTSKN
QFSLQLNSVTPEDTAVYYCAREEGYIEAHSVPYFDYWGQGTLVTVSSAST
KGPSVFPLAPCSRETSESTAALGCLVKDYFPEPVTVSWNSGALTSGVHTF
PAVLQSSGLYSLSSVVTVPSSSLGTKTYTCNVDHKPSNTKVDKRVESKYG
PPCPSCPAPEFLGGPSVFLFPPKPKDTLMISRTPEVTCVVVDVSQEDPEV
QFNWYVDGVEVHNAKTKPREEQFNSTYRVVSVLTVLHQDWLNGKEYKCKV
SNKGLPSSIEKTISKAKGQPREPQVYTLPPSQEEMTKNQVSLTCLVKGFY
PSDIAVEWESNGQPENNYKTTPPVLDSDGSFFLYSRLTVDKSRWQEGNVF
SCSVMHEALHNHYTQKSLSLSLGK
```

DNA Sequence
```
atgtctgtctccttcctcatcttcctgcccgtgctgggcctcccatgggg
tgtcctgtcacaggtacagctgcagcagtcaggtccaggactggtgaagc
cctcgcagaccctctcactcacctgtgccatctccggggacagtgtctct
agcaacagtgctgcttggaactggatcaggcagtccccatcgagaggcct
tgagtggctgggaaggacatactacaggtccaagtggtataatgattatg
aagtatctgtgaaaagtcgaataatcatcaacccagacacatccaagaac
cagttctccctgcagctgaactctgtgactcccgaggacacggctgtgta
ttactgtgcaagggaggaggggtatatagaagcccactcggttccttact
ttgactactggggccagggaaccctggtcaccgtctctagtgcttccacc
aagggcccatccgtcttccccctggcgccctgctccaggagcacctccga
gagcacagccgccctgggctgcctggtcaaggactacttccccgaaccgg
tgacggtgtcgtggaactcaggcgccctgaccagcggcgtgcacaccttc
ccggctgtcctacagtcctcaggactctactccctcagcagcgtggtgac
cgtgccctccagcagcttgggcacgaagacctacacctgcaacgtagatc
acaagcccagcaacaccaaggtggacaagagagttgagtccaaatatggt
cccccatgcccatcatgcccagcacctgagttcctggggggaccatcagt
cttcctgttccccccaaaacccaaggacactctcatgatctcccggaccc
ctgaggtcacgtgcgtggtggtggacgtgagccaggaagaccccgaggtc
cagttcaactggtacgtggatggcgtggaggtgcataatgccaagacaaa
gccgcgggaggagcagttcaacagcacgtaccgtgtggtcagcgtcctca
ccgtcctgcaccaggactggctgaacggcaaggagtacaagtgcaaggtc
tccaacaaaggcctcccgtcctccatcgagaaaaccatctccaaagccaa
agggcagccccgagagccacaggtgtacaccctgcccccatcccaggagg
agatgaccaagaaccaggtcagcctgacctgcctggtcaaaggcttctac
cccagcgacatcgccgtggagtgggagagcaatgggcagccggagaacaa
ctacaagaccacgcctcccgtgctggactccgacggctccttcttcctct
acagcaggctaaccgtggacaagagcaggtggcaggaggggaatgtcttc
tcatgctccgtgatgcatgaggctctgcacaaccactacacacagaagag
cctctccctgtctctgggtaaatga
```

9F7

9F7 LC
Full Amino Acid Sequence
```
MDMRVPAQLLGLLLLWLRGARCEIVMTQSPATLSVSPGERATLSCRASQR
GNNNLAWYQQKPGQAPRLLIYGASTRATGIPARFSGSGSGTEFTLTISSL
QSEDFAVYYCQQYNIWPRSFGQGTKLEIKRTVAAPSVFIFPPSDEQLKSG
TASVVCLLNNFYPREAKVQWKVDNALQSGNSQESVTEQDSKDSTYSLSST
LTLSKADYEKHKVYACEVTHQGLSSPVTKSFNRGEC
```

DNA Sequence
```
atggacatgagggtgcccgctcagctcctggggctcctgctgctgtggct
gagaggtgcgcgctgtgaaatagtgatgacgcagtctccagccaccctgt
ctgtgtctccaggggaaagagccaccctctcctgcagggccagtcagagg
ggtaataacaacttagcctggtaccagcagaaacctggccaggctcccag
gctcctcatctatggtgcatccaccagggccactggtatcccagccaggt
tcagtggcagtgggtctgggacagagttcactctcaccatcagcagcctg
cagtctgaagattttgcagtttattactgtcagcagtataatatctggcc
tcgcagttttggccaggggaccaagctggagatcaaacgtacggtggctg
caccatctgtcttcatcttcccgccatctgatgagcagttgaaatctgga
actgcctctgttgtgtgcctgctgaataacttctatcccagagaggccaa
agtacagtggaaggtggataacgccctccaatcgggtaactcccaggaga
gtgtcacagagcaggacagcaaggacagcacctacagcctcagcagcacc
ctgacgctgagcaaagcagactacgagaaacacaaagtctacgcctgcga
agtcacccatcagggcctgagctcgcccgtcacaaagagcttcaacaggg
gagagtgttga
```

9F7 HC IgG2
Full Amino Acid Sequence
```
MDMRVPAQLLGLLLLWLRGARCEVQLLESGGGLVQPGGSLRLSCAASGFT
FSNYAMSWVRQAPGKGLEWVSAVSGSGGSTFYADSMKGRFTISRDNSKNT
LYLQMNSLRAEDTAVYFCAKEGLEILYYFDYWGQGTLVTVSSASTKGPSV
FPLAPCSRETSESTAALGCLVKDYFPEPVTVSWNSGALTSGVHTFPAVLQ
SSGLYSLSSVVTVPSSNFGTQTYTCNVDHKPSNTKVDKTVERKCCVECPP
CPAPPVAGPSVFLFPPKPKDTLMISRTPEVTCVVVDVSHEDPEVQFNWYV
DGVEVHNAKTKPREEQFNSTFRVVSVLTVVHQDWLNGKEYKCKVSNKGLP
APIEKTISKTKGQPREPQVYTLPPSREEMTKNQVSLTCLVKGFYPSDIAV
EWESNGQPENNYKTTPPMLDSDGSFFLYSKLTVDKSRWQQGNVFSCSVMH
EALHNHYTQKSLSLSPGK
```

DNA Sequence
```
atggacatgagggtgcccgctcagctcctggggctcctgctgctgtggct
gagaggtgcgcgctgtgaggtgcagctgttggagtctggggggaggcttg
gtacagcctggggggtccctgagactctcctgtgcagcctctggattcacc
tttagcaactatgccatgagctgggtccgccaggctccagggaaggggct
ggagtgggtctcagctgttagtggtagtggtggtagcacattctacgcag
```

-continued
```
actccatgaagggccggttcaccatctccagagacaattccaagaacacg
ctgtatctgcaaatgaacagcctgagagccgaggacacggccgtgtattt
ctgtgcgaaagaggggctggagattctgtactactttgactactggggcc
agggaaccctggtcaccgtctctagtgcctccaccaagggcccatcggtc
ttccccctggcgccctgctccaggagcacctccgagagcacagcggccct
gggctgcctggtcaaggactacttccccgaaccggtgacggtgtcgtgga
actcaggcgctctgaccagcggcgtgcacaccttcccagctgtcctacag
tcctcaggactctactccctcagcagcgtggtgaccgtgccctccagcaa
cttcggcacccagacctacacctgcaacgtagatcacaagcccagcaaca
ccaaggtggacaagacagttgagcgcaaatgttgtgtcgagtgcccaccg
tgcccagcaccacctgtggcaggaccgtcagtcttcctcttccccccaaa
acccaaggacaccctcatgatctcccggacccctgaggtcacgtgcgtgg
tggtggacgtgagccacgaagaccccgaggtccagttcaactggtacgtg
gacggcgtggaggtgcataatgccaagacaaagccacgggaggagcagtt
caacagcacgttccgtgtggtcagcgtcctcaccgttgtgcaccaggact
ggctgaacggcaaggagtacaagtgcaaggtctccaacaaaggcctccca
gcccccatcgagaaaaccatctccaaaaccaaagggcagccccgagaacc
acaggtgtacaccctgcccccatcccgggaggagatgaccaagaaccagg
tcagcctgacctgcctggtcaaaggcttctaccccagcgacatcgccgtg
gagtgggagagcaatgggcagccggagaacaactacaagaccacacctcc
catgctggactccgacggctccttcttcctctacagcaagctcaccgtgg
acaagagcaggtggcagcaggggaacgtcttctcatgctccgtgatgcat
gaggctctgcacaaccactacacgcagaagagcctctccctgtctccggg
taaatga
```

9F7 IgM
Full Amino Acid Sequence
MDMRVPAQLLGLLLLWLRGARCEVQLLESGGGLVQPGGSLRLSCAASGFT
FSNYAMSWVRQAPGKGLEWVSAVSGSGGSTFYADSMKGRFTISRDNSKNT
LYLQMNSLRAEDTAVYFCAKEGLEILYYFDYWGQGTLVTVSSGSASAPTL
PPLVSCENSPSDTSSVAVGCLAQDFLPDSITFSWKYKNNSDISSTRGFPS
VLRGGKYAATSQVLLPSKDVMQGTDEHVVCKVQHPNGNKEKNVPLPVIAE
LPPKVSVPVPPRDGFFGNPRKSKLICQATGFSPRQIQVSWLREGKQVGSG
VTTDQVQAEAKESGPTTYKVTSTLTIKESDWLSQSMFTCRVDHRGLTFQQ
NASSMCVPDQDTAIRVFAIPPSFASIFLTKSTKLTCLVTDLTTYDSVTIS
WTRQNGEAVKTHTNISESHPNATFSAVGEASICEDDWNSGERFTCTVTHT
DLPSPLKQTISRPKGVALHRPDVYLLPPAREQLNLRESATITCLVTGFSP
ADVFVQWMQRGQPLSPEKYVTSAPMPEPQAPGRYFAHSILTVSEEEWNTG
ETYTCVVAHEALPNRVTERTVDKSTGKPTLYNVSLVMSDTAGTCYASDYK
DDDDKHHHHHH Cleaved Amino Acid Sequence EVQLLESGGGLVQPGGSLRLSCAASGFTFSNYAMSWVRQAPGKGLEWVSA
VSGSGGSTFYADSMKGRFTISRDNSKNTLYLQMNSLRAEDTAVYFCAKEG
LEILYYFDYWGQGTLVTVSSGSASAPTLPPLVSCENSPSDTSSVAVGCLA
QDFLPDSITFSWKYKNNSDISSTRGFPSVLRGGKYAATSQVLLPSKDVMQ
GTDEHVVCKVQHPNGNKEKNVPLPVIAELPPKVSVPVPPRDGFFGNPRKS
KLICQATGFSPRQIQVSWLREGKQVGSGVTTDQVQAEAKESGPTTYKVTS
TLTIKESDWLSQSMFTCRVDHRGLTFQQNASSMCVPDQDTAIRVFAIPPS
FASIFLTKSTKLTCLVTDLTTYDSVTISWTRQNGEAVKTHTNISESHPNA
TFSAVGEASICEDDWNSGERFTCTVTHTDLPSPLKQTISRPKGVALHRPD
VYLLPPAREQLNLRESATITCLVTGFSPADVFVQWMQRGQPLSPEKYVTS
APMPEPQAPGRYFAHSILTVSEEEWNTGETYTCVVAHEALPNRVTERTVD
KSTGKPTLYNVSLVMSDTAGTCY DNA Sequence
```
atggacatgagggtgcccgctcagctcctgggctcctgctgctgtggct
gagaggtgcgcgctgtgaggtgcagctgttggagtctgggggaggcttgg
tacagcctggggggtccctgagactctcctgtgcagcctctggattcacc
tttagcaactatgccatgagctgggtccgccaggctccagggaaggggct
ggagtgggtctcagctgttagtggtagtggtggtagcacattctacgcag
actccatgaagggccggttcaacatctccagagacaattccaagaacacg
ctgtatctgcaaatgaacagcctgagagccgaggacacggccgtgtattt
ctgtgcgaaagaggggctggagattctgtactactttgactactggggcc
agggaaccctggtcaccgtctctagtgggagtgcatccgccccaacccct
tccccctcgtatcctgtgagaattcccgtcggatacgagcagcgtggc
cgttggctgcctcgcacaggacttccttcccgactccatcactttctcct
ggaaatacaagaacaactctgacatcagcagcacccggggcttcccatca
gtcctgagaggggcaagtacgcagccacctcacaggtgctgctgccttc
caaggacgtcatgcagggcacagacgaacacgtggtgtgcaaagtccagc
accccaacggcaacaaagaaaagaacgtgcctcttccagtgattgccgag
ctgcctcccaaagtgagcgtcttcgtcccaccccgcgacggcttcttcgg
caaccccgcaagtccaagctcatctgccaggccacgggtttcagtcccc
ggcagattcaggtgtcctggctgcgcgaggggaagcaggtggggtctggc
gtcaccacggaccaggtgcaggctgaggccaaagagtctgggcccacgac
ctacaaggtgaccagcacactgaccatcaaagagcgactggctcagcc
agagcatgttcacctgccgcgtggatcacaggggcctgaccttccagcag
aatgcgtcctccatgtgtgtccccgatcaagacacagccatccgggtctt
cgccatccccccatcctttgccagcatcttcctcaccaagtccaccaagt
tgacctgcctggtcacagacctgaccacctatgacagcgtgaccatctcc
tggacccgccagaatggcgaagctgtgaaaacccacaccaacatctccga
gagccacccaatgccacttcagcgccgtgggtgaggccagcatctgcg
aggatgactggaattccggggagaggttcacgtgcaccgtgacccacaca
```

-continued gacctgccctcgccactgaagcagaccatctcccggcccaagggggtggc cctgcacaggcccgatgtctacttgctgccaccagcccgggagcagctga acctgcgggagtcggccaccatcacgtgcctggtgacgggcttctctccc gcggacgtcttcgtgcagtggatgcagaggggcagcccttgtccccgga gaagtatgtgaccagcgcccaatgcctgagcccaggcccaggccggt acttcgccacagcatcctgaccgtgtccgaagaggaatggaacacgggg gagacctacacctgcgtggtggcccatgaggccctgcccaacagggtcac cgagaggaccgtggacaagtccaccggtaaacccaccctgtacaacgtgt ccctggtcatgtccgacacagctggcacctgctacgctagcgattataaa gatgatgatgataaacatcaccatcaccatcactga

11D12

11D12 LC
Full Amino Acid Sequence
MDMRVPAQLLGLLLLWLRGARCQPVLTQPPSASASLGASVTLTCTLSSGY

SNYKVDWYQQRPGKGPRFVMRVGTGGIVGSKGDGIPDRFSVLGSGLNRYL

TIKNIQEEDESDYHCGADHGSGSNFVWVFGGGTKLTVLGQPKANPTVTLF

PPSSEELQANKATLVCLISDFYPGAVTVAWKADGSPVKAGVETTKPSKQS

NNKYAASSYLSLTPEQWKSHRSYSCQVTHEGSTVEKTVAPTECS

DNA Sequence
atggacatgagggtgcccgctcagctcctggggctcctgctgctgtggct gagaggtgcgcgctgtcagcctgtgctgactcagccaccttctgcatcag cctccctgggagcctcggtcacactcacctgcaccctgagcagcggctac agtaattataaagtggactggtaccagcagagaccagggaagggcccccg gtttgtgatgcgagtgggcactggtgggattgtgggatccaaggggatg gcatccctgatcgcttctcagtcttgggctcaggcctgaatcggtacctg accatcaagaacatccaggaagaggatgagagtgactaccactgtggggc agaccatggcagtgggagcaacttcgtgtgggtgttcggcggagggacca agctgaccgtcctaggtcagcccaaggccaacccactgtcactctgttc ccgcccctcctctgaggagctccaagccaacaaggccacactagtgtgtct gatcagtgacttctacccgggagctgtgacagtggcctggaaggcagatg gcagccccgtcaaggcgggagtggagaccaccaaacctccaaacagagc aacaacaagtacgcggccagcagctacctgagcctgacgcccgagcagtg gaagtcccacagaagctacagctgccaggtcacgcatgaagggagcaccg tggagaagacagtggcccctacagaatgttcatga 1D12 HC IgG2
Full Amino Acid Sequence
MDMRVPAQLLGLLLLWLRGARCQVQLQQWGAGLLKPSETLSLTCAVYGGS

FSGYYWSWIRQPPGKGLEWIGEINHSGSTNYNPSLKSRVTISVDTSKNQF

SLKLSSVTAADTAVYYCARAKFYGWGNYPFDSWGQGTLVTVSSASTKGPS

VFPLAPCSRSTSESTAALGCLVKDYFPEPVTVSWNSGALTSGVHTFPAVL

QSSGLYSLSSVVTVPSSNFGTQTYTCNVDHKPSNTKVDKTVERKCCVECP

PCPAPPVAGPSVFLFPPKPKDTLMISRTPEVTCVVVDVSHEDPEVQFNWY

VDGVEVHNAKTKPREEQFNSTFRVVSVLTVVHQDWLNGKEYKCKVSNKGL

PAPIEKTISKTKGQPREPQVYTLPPSREEMTKNQVSLTCLVKGFYPSDIA

VEWESNGQPENNYKTTPPMLDSDGSFFLYSKLTVDKSRWQQGNVFSCSVM

HEALHNHYTQKSLSLSPGK

DNA Sequence
atggacatgagggtgcccgctcagctcctggggctcctgctgctgtggct gagaggtgcgcgctgtcaggtgcagctacagcagtggggcgcaggactgt tgaagccttcggagaccctgtccctcacctgcgctgtctatggtgggtcc ttcagtggttactactggagctggatccgccagcccccagggaagggct ggagtggattgggaaatcaatcatagtggaagcaccaactacaacccgt ccctcaagagtcgagtcaccatatcagtagacacgtccaagaaccagttc tccctgaagctgagctctgtgaccgccgcggacacggctgtgtattactg tgcgagagcaaagttctatggttgggggaattatccgtttgactcctggg gccaggaaccctggtcaccgtctctagtgcctccaccaagggcccatcg gtcttccccctggcgccctgctccaggagcacctccgagagcacagcggc cctgggctgcctggtcaaggactacttccccgaaccggtgacggtgtcgt ggaactcaggcgctctgaccagcggcgtgcacaccttcccagctgtccta cagtcctcaggactctactccctcagcagcgtggtgaccgtgccctccag caacttcggcacccagacctacacctgcaacgtagatcacaagcccagca acaccaaggtggacaagacagttgagcgcaaatgttgtgtcgagtgccca ccgtgcccagcaccacctgtggcaggaccgtcagtcttcctcttccccc caaaacccaaggacaccctcatgatctcccggacccctgaggtcacgtgcg tggtggtggacgtgagccacgaagaccccgaggtccagttcaactggtac gtggacggcgtggaggtgcataatgccaagacaaagccacgggaggagca gttcaacagcacgttccgtgtggtcagcgtcctcaccgttgtgcaccagg actggctgaacggcaaggagtacaagtgcaaggtctccaacaaaggcctc ccagcccccatcgagaaaaccatctccaaaaccaaagggcagccccgaga accacaggtgtacaccctgcccccatcccgggaggagatgaccaagaacc aggtcagcctgacctgcctggtcaaaggcttctaccccagcgacatcgcc gtggagtgggagagcaatgggcagccggagaacaactacaagaccacacc tcccatgctggactccgacggctccttcttcctctacagcaagctcaccg tggacaagagcaggtggcagcaggggaacgtcttctcatgctccgtgatg catgaggctctgcacaaccactacacgcagaagagcctctccctgtctcc gggtaaatga 11D12 IgM
Full Amino Acid Sequence
MDMRVPAQLLGLLLLWLRGARCQVQLQQWGAGLLKPSETLSLTCAVYGGS

FSGYYWSWIRQPPGKGLEWIGEINHSGSTNYNPSLKSRVTISVDTSKNQF

SLKLSSVTAADTAVYYCARAKFYGWGNYPFDSWGQGTLVTVSSGSASAPT

LFPLVSCENSPSDTSSVAVGCLAQDFLPDSITFSWKYKNNSDISSTRGFP

SVLRGGKYAATSQVLLPSKDVMQGTDEHVCKVQHPNGNKEKNVPLPVIA
ELPPKVSVFVPPRDGPFGNPRKSKLICQATGFSPRQIQVSWLREGKQVGS
GVTTDQVQAEAKESGPTTYKVTSTLTIKESDWLSQSMFTCRVDHRGLTFQ
QNASSMCVPDQDTAIRVFAIPPSPASIFLTKSTKLTCLVTDLTTYDSVTI
SWTRQNGEAVKTHTNISESHPNATFSAVGEASICEDDWNSGERFTCTVTH
TDLPSPLKQTISRPKGVALHRPDVYLLPPAREQLNLRESATITCLVTGFS
PADVFVQNMQRGQPLSPEKYVTSAPMPEPQAPGRYFAHSILTVSEEEWNT
GETYTCVVAHEALPNRVTERTVDKSTGKPTLYNVSLVMSDTAGTCYASDY
KDDDDKHHHHHH

Cleaved Amino Acid Sequence
QVQLQQWGAGLLKPSETLSLTCAVYGGSFSGYYWSWIRQPPGKGLEWIGE
INHSGSTNYNPSLKSRVTISVDTSKNQFSLKLSSVTAADTAVYYCARAKF
YGWGNYPFDSWGQGTLVTVSSGSASAPTLPPLVSCENSPSDTSSVAVGCL
AQDFLPDSITFSWKYKNNSDISSTRGFPSVLRGGKYAATSQVLLPSKDVM
QGTDEHVCKVQHPNGNKEKNVPLPVIAELPPKVSVFVPPRDGPFGNPRK
SKLICQATGFSPRQIQVSWLREGKQVGSGVTTDQVQAEAKESGPTTYKVT
STLTIKESDWLSQSMFTCRVDHRGLTFQQNASSMCVPDQDTAIRVFAIPP
SPASIFLTKSTKLTCLVTDLTTYDSVTISWTRQNGEAVKTHTNISESHPN
ATFSAVGEASICEDDWNSGERFTCTVTHTDLPSPLKQTISRPKGVALHRP
DVYLLPPAREQLNLRESATITCLVTGFSPADVFVQNMQRGQPLSPEKYVT
SAPMPEPQAPGRYFAHSILTVSEEEWNTGETYTCVVAHEALPNRVTERTV
DKSTGKPTLYNVSLVMSDTAGTCY DNA Sequence
atggacatgagggtgcccgctcagctcctggggctcctgctgctgtggct
gagaggtgcgcgctgtcaggtgcagctacagcagtggggcgcaggactgt
tgaagcttcggagaccctgtccctcacctgcgctgtctatggtgggtcc
ttcagtggttactactggagctggatccgccagcccccagggaaggggct
ggagtggattggggaaatcaatcatagtggaagcaccaactacaacccgt
ccctcaagagtcgagtcaccatatcagtagacacgtccaagaaccagttc
tccctgaagctgagctctgtgaccgccgcggacacggctgtgtattactg
tgcgagagcaaagttctatggttggggaattatccgtttgactcctggg
gccagggaaccctggtcaccgtctctagtgggagtgcatccgccccaacc
cttttccccctcgtatcctgtgagaattccccgtcggatacgagcagcgt
ggccgttggctgcctcgcacaggacttccttcccgactccatcactttct
cctggaaatacaagaacaactctgacatcagcagcacccggggcttccca
tcagtcctgagaggggcaagtacgcagccacctcacaggtgctgctgcc
ttccaaggacgtcatgcagggcacagacgaacacgtggtgtgcaaagtcc
agcaccccaacggcaacaaagaaaagaacgtgcctcttccagtgattgcc
gagctgcctcccaaagtgagcgtcttcgtcccaccccgcgacggcttct
cggcaaccccgcaagtccaagctcatctgccaggccacgggtttcagtc cccggcagattcaggtgtcctggctgcgcgaggggaagcaggtggggtct
ggcgtcaccacggaccaggtgcaggctgaggccaaagagtctgggcccac
gacctacaaggtgaccagcacactgaccatcaaagagagcgactggctca
gccagagcatgttcacctgccgcgtggatcacaggggcctgaccttccag
cagaatgcgtcctccatgtgtgtccccgatcaagacacagccatccgggt
cttcgccatcccccatccttgccagcatcttcctcaccaagtccacca
agttgacctgcctggtcacagacctgaccacctatgacagcgtgaccatc
tcctggacccgccagaatggcgaagctgtgaaaacccacaccaacatctc
cgagagccaccccaatgccactttcagcgccgtgggtgaggccagcatct
gcgaggatgactggaattccggggagaggttcacgtgcaccgtgacccac
acagacctgccctcgccactgaagcagaccatctcccggcccaagggggt
ggccctgcacaggcccgatgtctacttgctgccaccagcccgggagcagc
tgaacctgcgggagtcggccaccatcacgtgcctggtgacgggcttctct
cccgcggacgtcttcgtgcagtggatgcagagggggcagcccttgtcccc
ggagaagtatgtgaccagcgccccaatgcctgagcccaggccccaggcc
ggtacttcgcccacagcatcctgaccgtgtccgaagaggaatggaacacg
ggggagacctacacctgcgtggtggcccatgaggccctgcccaacagggt
caccgagaggaccgtggacaagtccaccggtaaacccaccctgtacaacg
tgtccctggtcatgtccgacacagctggcacctgctacgctagcgattat
aaagatgatgatgataaacatcaccatcaccatcactga 3A4
3A4 LC
Full Amino Acid Sequence
MDMRVPAQLLGLLLLWLRGARCDIQMTQSPSSLSASVGDRVTITCQASQD
ISNFLNWYQQKPGKAPKLLIYDASNLETGVPSRFSGSGSGTDFTFTISSL
QPEDVATYYCQQYDNFPLTFGGGTKVEIKRTVAAPSVFIFPPSDEQLKSG
TASVVCLLNNFYPREAKVQWKVDNALQSGNSQESVTEQDSKDSTYSLSST
LTLSKADYEKHKVYACEVTHQGLSSPVTKSFNRGEC DNA Sequence
atggacatgagggtgcccgctcagctcctggggctcctgctgctgtggct
gagaggtgcgcgctgtgacatccagatgacccagtctccatcctccctgt
ctgcatctgtaggagacagagtcaccatcacttgccaggcgagtcaggac
attagcaacttttgaattggtatcagcagaaaccagggaaagcccctaa
gctcctgatctacgatgcatccaatttggaaacaggggtcccatcaaggt
tcagtggaagtggatctgggacagattttactttcaccatcagcagcctg
cagcctgaagatgttgcaacatattactgtcaacagtatgataatttccc
gctcactttcggcggagggaccaaggtggagatcaaacgtacggtggctg
caccatctgtcttcatcttcccgccatctgatgagcagttgaaatctgga
actgcctctgttgtgtgcctgctgaataacttctatcccagagaggccaa
agtacagtggaaggtggataacgccctccaatcgggtaactcccaggaga
gtgtcacagagcaggacagcaaggacagcacctacagcctcagcagcacc -continued
ctgacgctgagcaaagcagactacgagaaacacaaagtctacgcctgcga agtcacccatcagggcctgagctcgcccgtcacaaagagcttcaacaggg gagagtgttg 3A4 HC IgG4
Full Amino Acid Sequence
MDMRVPAQLLGLLLLWLRGARCQVQLVQSGAEVKKPGASVKVSCKASGYT

FTTYGINWVRQAPGQGLEWMGWLSAYSGNTNYAQKLQGRVTMTTDTSTST

AYMELRSLRSDDTAVYYCARGVGASFYFDYWGQGTLVTVSSASTKGPSVF

PLAPCSRSTSESTAALGCLVKDYFPEPVTVSWNSGALTSGVHTFPAVLQS

SGLYSLSSVVTVPSSSLGTKTYTCNVDHKPSNTKVDKRVESKYGPPCPSC

PAPEFLGGPSVFLFPPKPKDTLMISRTPEVTCVVVDVSQEDPEVQFNWYV

DGVEVHNAKTKPREEQFNSTYRVVSVLTVLHQDWLNGKEYKCKVSNKGLP

SSIEKTISKAKGQPREPQVYTLPPSQEEMTKNQVSLTCLVKGFYPSDIAV

EWESNGQPENNYKTTPPVLDSDGSFFLYSRLTVDKSRWQEGNVFSCSVMH

EALHNHYTQKSLSLSLGK

DNA Sequence
atggacatgagggtgcccgctcagctcctggggctcctgctgctgtggct gagaggtgcgcgctgtcaggttcagctggtgcagtctggagctgaggtga agaagcctggggcctcagtgaaggtctcctgcaaggcttctggttacacc tttaccacctatggtatcaactgggtgcgacaggcccctggacaagggct tgagtggatgggatggctcagcgcttacagtggtaacacaaactatgcac agaaactccagggcagagtcaccatgaccacagacacatccacgagcaca gcctacatggagctgaggagcctgagatctgacgacacggccgtgtatta ctgtgcgagaggagtgggagcttcctttttactttgactactggggccagg gaaccctggtcaccgtctctagtgcttccaccaagggcccatccgtcttc cccctggcgccctgctccaggagcacctccgagagcacagccgccctggg ctgcctggtcaaggactacttccccgaaccggtgacggtgtcgtggaact caggcgccctgaccagcggcgtgcacaccttcccggctgtcctacagtcc tcaggactctactccctcagcagcgtggtgaccgtgccctccagcagctt gggcacgaagacctacacctgcaacgtagatcacaagcccagcaacacca aggtggacaagagagttgagtccaaatatggtcccccatgcccatcatgc ccagcacctgagttcctggggggaccatcagtcttcctgttccccccaaa acccaaggacactctcatgatctcccggacccctgaggtcacgtgcgtgg tggtggacgtgagccaggaagaccccgaggtccagttcaactggtacgtg gatggcgtggaggtgcataatgccaagacaaagccgcgggaggagcagtt caacagcacgtaccgtgtggtcagcgtcctcaccgtcctgcaccaggact ggctgaacggcaaggagtacaagtgcaaggtctccaacaaaggcctcccg tcctccatcgagaaaaccatctccaaagccaaagggcagccccgagagcc acaggtgtacaccctgcccccatcccaggaggagatgaccaagaaccagg tcagcctgacctgcctggtcaaaggcttctaccccagcgacatcgccgtg gagtgggagagcaatgggcagccggagaacaactacaagaccacgcctcc cgtgctggactccgacggctccttcttcctctacagcaggctaaccgtgg -continued
acaagagcaggtggcaggaggggaatgtcttctcatgctccgtgatgcat gaggctctgcacaaccactacacacagaagagcctctccctgtctctggg taaatga

3F5

3F5 LC
Full Amino Acid Sequence
MDMRVPAQLLGLLLLWLRGARCDIQMTQSPSSLSASVGDRVTITCQASQD

ISNYLNWFQQKPGKAPNLLIYDASNLETGVPSRFSGGGSGTDFTFTISSL

QPEDIATYYCQQYDDLPLTFGGGTKVEIKRTVAAPSVFIFPPSDEQLKSG

TASVVCLLNNFYPREAKVQWKVDNALQSGNSQESVTEQDSKDSTYSLSST

LTLSKADYEKHKVYACEVTHQGLSSPVTKSFNRGEC

DNA Sequence
atggacatgagggtgcccgctcagctcctggggctcctgctgctgtggct gagaggtgcgcgctgtgacatccagatgacccagtctccatcctccctgt ctgcatctgtaggagacagagtcaccatcacttgccaggcgagtcaggac attagcaactatttaaattggtttcagcagaaaccaggcaaagcccctaa tctcctgatctacgatgcatccaatttggaaacaggggtcccatcaaggt tcagtggaggtggatctgggacagattttactttcaccatcagcagcctg cagcctgaagatattgcaacatattactgtcaacagtatgatgatctccc gctcactttcggcggagggaccaaggtggagatcaaacgtacggtggctg caccatctgtcttcatcttcccgccatctgatgagcagttgaaatctgga actgcctctgttgtgtgcctgctgaataacttctatcccagagaggccaa agtacagtggaaggtggataacgccctccaatcgggtaactcccaggaga gtgtcacagagcaggacagcaaggacagcacctacagcctcagcagcacc ctgacgctgagcaaagcagactacgagaaacacaaagtctacgcctgcga agtcacccatcagggcctgagctcgcccgtcacaaagagcttcaacaggg gagagtgttga 3F5 HC IgG1
Full Amino Acid Sequence
MDMRVPAQLLGLLLLWLRGARCEVQLVESGGGLVQPGGSLRLSCAASGFT

FSSYGMNWVRQAPGKGLEWVSYISSSSSTIYYADSVKGRFTISRDNAKNS

LYLQMNSLRDEDTAVYYCARDRITSWYEEDYYYGMDVWGQGTTVTVSSA

STKGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKKVEPK

SCDKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLTCL

VKGFYPSDIAVEWESNGQPENNYKTTPPVLDSDGSFFLYSKLTVDKSRWQ

QGNVFSCSVMHEALHNHYTQKSLSLSPGK

DNA Sequence
atggacatgagggtgcccgctcagctcctggggctcctgctgctgtggct gagaggtgcgcgctgtgaggtgcagctggtggagtctgggggaggcttgg -continued tacagcctggggggtccctgagactctcctgtgcagcctctggattcacc ttcagtagctatggcatgaactgggtccgccaggctccagggaagggact ggagtgggtttcatacattagtagtagtagtagtaccatatactacgcag actctgtgaagggccgattcaccatctccagagacaatgccaagaactca ctgtatctgcaaatgaacagcctgagagacgaggacacggctgtgtatta ctgtgcgagagataggatcaccagctggtacgaggaggactactattact acggtatggacgtctggggccaagggaccacggtcaccgtctctagtgcc tccaccaagggcccatcggtcttccccctggcaccctcctccaagagcac ctctgggggcacagcggccctgggctgcctggtcaaggactacttcccg aaccggtgacggtgtcgtggaactcaggcgccctgaccagcggcgtgcac accttcccggctgtcctacagtcctcaggactctactccctcagcagcgt ggtgaccgtgccctccagcagcttgggcacccagacctacatctgcaacg tgaatcacaagcccagcaacaccaaggtggacaagaaagttgagcccaaa tcttgtgacaaaactcacacatgcccaccgtgcccagcacctgaactcct gggggaccgtcagtcttcctcttccccccaaaacccaaggacaccctca tgatctcccggacccctgaggtcacatgcgtggtggtggacgtgagccac gaagaccctgaggtcaagttcaactggtacgtggacggcgtggaggtgca -continued taatgccaagacaaagccgcgggaggagcagtacaacagcacgtaccgtg tggtcagcgtcctcaccgtcctgcaccaggactggctgaatggcaaggag tacaagtgcaaggtctccaacaaagccctcccagcccccatcgagaaaac catctccaaagccaaagggcagccccgagaaccacaggtgtacaccctgc ccccatcccgggaggagatgaccaagaaccaggtcagcctgacctgcctg gtcaaaggcttctatcccagcgacatcgccgtggagtgggagagcaatgg gcagccggagaacaactacaagaccacgcctcccgtgctggactccgacg gctccttcttcctctatagcaagctcaccgtggacaagagcaggtggcag caggggaacgtcttctcatgctccgtgatgcatgaggctctgcacaacca ctacacgcagaagagcctctccctgtctccgggtaaatga Each reference cited herein is hereby incorporated by reference in its entirety for all that it teaches and for all purposes.

The present invention is not to be limited in scope by the specific embodiments described herein, which are intended as single illustrations of individual aspects of the invention, and functionally equivalent methods and components are invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. An isolated antibody or fragment of an antibody, wherein the antibody or the fragment specifically binds to human erythropoietin and comprises:
   a. a variable heavy chain complementarity determining region 1 (VH CDR1) of SEQ ID NO: 48;
   b. a VH CDR2 of SEQ ID NO: 49;
   c. a VH CDR3 of SEQ ID NO: 50;
   d. a variable light chain complementarity determining region 1 (VL CDR1) of SEQ ID NO: 18;
   e. a VL CDR2 of SEQ ID NO: 19; and
   f. a VL CDR3 of SEQ ID NO: 20.

2. An isolated antibody or antibody fragment, wherein the antibody or the fragment specifically binds human erythropoietin and comprises: a heavy chain variable of SEQ ID NO: 69 and comprises a light chain variable domain of SEQ ID NO: 63.

3. The antibody of claims 1 or 2, wherein the antibody is a monoclonal antibody.

4. The antibody of claims 1 or 2, wherein the antibody is a chimeric antibody, a humanized antibody, or a fully human antibody.

5. A sterile composition comprising the isolated antibody or antibody fragment of any one of claims 1 or 2.

6. A kit for detecting antibody-mediated pure red cell aplasia (amPRCA) or predicting the risk or onset of amPRCA comprising the anti-human erythropoietin antibody of claims 1 or 2, and human erythropoietin.

* * * * *